United States Patent
Achkar et al.

(10) Patent No.: US 9,260,709 B2
(45) Date of Patent: Feb. 16, 2016

(54) VALENCENE SYNTHASE FROM CALLITROPSIS NOOTKATENSIS

(75) Inventors: Jihane Achkar, Zurich (CH); Theodorus Sonke, Guttecoven (NL); Martinus Julius Beekwilder, Renkum (NL); Hendrik Jan Bouwmeester, Wageningen (NL); Hendrik Jan Bosch, Wageningen (NL)

(73) Assignee: ISOBIONICS B.V., Geleen (NL)

( * ) Notice: Subject to any disclaimer, the term of this patent is extended or adjusted under 35 U.S.C. 154(b) by 698 days.

(21) Appl. No.: 13/516,545

(22) PCT Filed: Dec. 15, 2010

(86) PCT No.: PCT/NL2010/050848
§ 371 (c)(1),
(2), (4) Date: Dec. 21, 2012

(87) PCT Pub. No.: WO2011/074954
PCT Pub. Date: Jun. 23, 2011

(65) Prior Publication Data
US 2014/0075600 A1      Mar. 13, 2014

(30) Foreign Application Priority Data
Dec. 16, 2009   (EP) .................................... 09179499

(51) Int. Cl.
*C12N 9/88* (2006.01)
*C12P 7/26* (2006.01)
*C12P 7/40* (2006.01)
*C12P 5/00* (2006.01)

(52) U.S. Cl.
CPC . *C12N 9/88* (2013.01); *C12P 5/007* (2013.01); *C12P 7/26* (2013.01); *C12P 7/40* (2013.01)

(58) Field of Classification Search
None
See application file for complete search history.

(56) References Cited

U.S. PATENT DOCUMENTS 7,442,785 B2 *  10/2008  Chappell et al. ............. 536/23.6
2008/0318292 A1 * 12/2008  Keasling et al. ............. 435/167

OTHER PUBLICATIONS

UniProtKB Q675L0 (Nov. 3, 2009).*
Fraatz et el., 2009, Appl. Microbiol. Biotechnol. 83: 35-41.*
Sharon-Asa et al., 2003, Plant Journal 36: 664-674.*
Thornton et al., 2000, Nature Structural Biology, structural genomic supplement, Nov. 2000: 991-994.*
Guo et al., 2004, Proceedings of the National Academy of Sciences USA 101: 9205-9210.*
Keskin et al., 2004, Protein Science 13: 1043-1055.*
International Search Report for PCT/NL2010/050848, date of mailing Jul. 1, 2011.
Martin DM. Functional characterization of nine Norway Spruce TPS genes and evolution of gymnosperm terpene synthases of the TPS-d subfamily. *Plant Physiology*. vol. 135, No. 4, Aug. 2004, pp. 1908-1927.
Sharon-Asa, L., et al. Citrus fruit flavor and aroma biosynthesis: Isolation, functional characterization, and developmental regulation of Cstps1, a key gene in the production of the sesquiterpene aroma compound valencene. *Plant Journal*. vol. 36, No. 5, Dec. 1, 2003, pp. 664-674.
Furusawa M., et al. Highly efficient production of nootkatone, the grapefruit aroma from valencene, by biotransformation. *Chemical and Pharmaceutical Bulletin*. vol. 53, No. 11, Nov. 1, 2005, pp. 1513-1514.
Chappell, J. Valencene synthase—a biochemical magician and harbinger of transgenic aromas. *Trends in Plant Science*. vol. 9, No. 6, Jun. 1, 2004, pp. 266-269.
Database EMBL [Online] Picea abies longifolene synthase (TPS-Lon) mRNA, complete cds, retrieved from EBI accession No. EMBL:AY473625. Database accession No. AY473625 compound. Aug. 29, 2004.
Database UniProt [Online] SubName: Full=Alpha pinene synthase, XP002579009, retrieved from EBI accession No. UNIPROT:C3RSF5. Database accession No. AF441124 compound. Jun. 16, 2009.
Database EMBL [Online] Cryptomer japonica cDNA, clone. XP002579010, retrieved from EBI accession No. EMBL:BW994467. Database accession No. BW994467 compound. Apr. 1, 2006.
Database EMBL [Online] Citrus sinensis valencene synthase (tps1), complete cds, retrieved from EBI accession No. EMBL: AF441124. Database accession No. AF441124 compound. Nov. 1, 2003.

* cited by examiner

*Primary Examiner* — Amjad Abraham
*Assistant Examiner* — Bratislav Stankovic
(74) *Attorney, Agent, or Firm* — Nixon & Vanderhye P.C.

(57) ABSTRACT

The present invention relates to a valencene synthase, to a nucleic acid encoding such valencene synthase, to a host cell comprising said encoding nucleic acid sequence and to a method for preparing valencene, comprising converting farnesyl diphosphate to valencene in the presence of a valencene synthase according to the invention.

10 Claims, No Drawings

VALENCENE SYNTHASE FROM CALLITROPSIS NOOTKATENSIS

The invention is directed to a valencene synthase, to a nucleic acid encoding said valencene synthase, to an expression vector comprising said nucleic acid, to a host cell comprising said expression vector, to a method of preparing valencene, to a method of preparing nootkatone and to a method of preparing a valencene synthase.

Many organisms have the capacity to produce a wide array of terpenes and terpenoids. Terpenes are actually or conceptually built up from 2-methylbutane residues, usually referred to as units of isoprene, which has the molecular formula $C_5H_8$. One can consider the isoprene unit as one of nature's common building blocks. The basic molecular formulae of terpenes are multiples of that formula: $(C_5H_8)_n$, wherein n is the number of linked isoprene units. This is called the isoprene rule, as a result of which terpenes are also denoted as isoprenoids. The isoprene units may be linked together "head to tail" to form linear chains or they may be arranged to form rings. In their biosynthesis, terpenes are formed from the universal 5 carbon precursors isopentenyl diphosphate (IPP) and its isomer, dimethylallyl diphosphate (DMAPP). Accordingly, a terpene carbon skeleton generally comprises a multiple of 5 carbon atoms. Most common are the 5-, 10-, 15-, 20-, 30- and 40-carbon terpenes, which are referred to as hemi-, mono-, sesqui-, di-, tri- and tetraterpenes, respectively. Besides "head-to-tail" connections, tri- and tetraterpenes also contain one "tail-to-tail" connection in their centre. The terpenes may comprise further functional groups, like alcohols and their glycosides, ethers, aldehydes, ketones, carboxylic acids and esters. These functionalised terpenes are herein referred to as terpenoids. Like terpenes, terpenoids generally have a carbon skeleton having a multiple of 5 carbon atoms. It should be noted that the total number of carbons in a terpenoid does not need to be a multiple of 5, e.g. the functional group may be an ester group comprising an alkyl radical having any number of carbon atoms.

Apart from the definitions given above, it is important to note that the terms "terpene", "terpenoid" and "isoprenoid" are frequently used interchangeably in open as well as patent literature.

Valencene is a naturally occurring terpene, produced in specific plants, such as various citrus fruits. In these plants farnesyl diphosphate (FPP) is enzymatically converted into valencene in the presence of a valencene synthase.

Valencene is, e.g., industrially applicable as an aroma or flavour. Valencene can be obtained by distillation from citrus essential oils obtained from citrus fruits, but isolation from these oils is cumbersome because of the low valencene concentration in these fruits (0.2 to 0.6% by weight).

It has been proposed to prepare valencene microbiologically, making use of micro-organisms genetically modified by incorporation of a gene that is coding for a protein having valencene synthase activity. Thus produced valencene synthase can be used for the preparation of valencene from FPP, a conversion which might be executed as an isolated reaction (in vitro) or as part of a longer metabolic pathway eventually leading to the production of valencene from sugar (in vivo).

Several valencene synthases from citrus are known. For instance, in U.S. Pat. Nos. 7,273,735 and 7,442,785 the expression of valencene synthase from *Citrus×paradisi* in *E. coli* is described. Further, valencene synthase from *Vitis vinifera* has been described by Lücker et al. (Phytochemistry (2004) 65: 2649-2659). Although the expression of these valencene synthases in a host organism has been described, the actual enzymatic activity is only shown under in vitro conditions.

A number of papers also describe the activity of valencene synthases in vivo. Takahashi et al. (Biotechnol. Bioeng. (2007) 97: 17-181), for instance, report the expression of a *Citrus×paradisi* valencene synthase gene (accession number AF411120) in *Saccharomyces cerevisiae* strains that have been optimized for enhanced levels of the key intermediate FPP by amongst other things inactivating the ERG9 gene through a knockout mutation. Cultivation of the best strain in a defined minimal medium containing ergosterol to complement the ERG9 mutation for 216 h led to production of 20 mg/L valencene. Asadollahi et al. (Biotechnol. Bioeng. (2008) 99: 666-677) describe a rather similar valencene production system, which is based on the expression of a *Citrus×paradisi* valencene synthase gene (accession number CQ813508; 3 out of 548 amino acids difference compared to AF411120) in a *S. cerevisiae* strain in which the expression of the ERG9 gene was downregulated via replacement of the native ERG9 promoter with the regulatable METS promoter. Cultivation of this strain in a minimal medium applying a two-liquid phase fermentation with dodecane as the organic solvent resulted in the formation of 3 mg/L valencene in 60 h.

The currently known valencene synthases have a number of distinct drawbacks which are in particular undesirable when they are applied in an industrial valencene production process wherein valencene is prepared from FPP, either in an isolated reaction (in vitro), e.g. using an isolated valencene synthase or (permeabilized) whole cells, or otherwise, e.g. in a fermentative process being part of a longer metabolic pathway eventually leading to the production of valencene from sugar (in vivo). Internal research by the present inventors revealed, for instance, that overexpression of the valencene synthase from *Citrus×paradisi* (CQ813508) or from *Citrus sinensis* (AF441124) in different microorganisms (*E. coli, Rhodobacter sphaeroides, Saccharomyces cerevisiae*) in active form is troublesome, resulting in a severely impaired production rate of valencene. Similarly, Asadollahi et al. (Biotechnol. Bioeng. (2008) 99: 666-677) found that the low valencene synthesis in a recombinant *S. cerevisiae* strain was caused by poor heterologous expression of the *Citrus×paradisi* valencene synthase gene.

Moreover, the *C.×paradisi* valencene synthase, which is nearly identical to the enzyme form *C. sinensis*, has been found to catalyse the conversion of FPP not only into valencene but also into significant amounts of germacrene A (U.S. Pat. No. 7,442,785 B2), at neutral or mildly alkaline pH.

An incubation of this enzyme with FPP at pH 7.5, for instance, resulted in the formation of two compounds accounting for over 95% of the total reaction products formed, 30% of which was beta-elemene (a thermal rearrangement product of germacrene A) and 65% of which was valencene. The inventors further found that also under in vivo conditions, significant amounts of the germacrene A side product are formed by this enzyme; cultivation of a *Rhodobacter sphaeroides* strain optimised for isoprenoids production and carrying the *C.×paradisi* valencene synthase gene (accession number CQ813508) led to the formation of valencene and beta-elemene in 48% and 25% of the total amount of sesquiterpenes formed, respectively.

The valencene synthase from grapevine *Vitis vinifera* (accession number AAS66358) displays a similar lack of specificity. Expression in *E. coli* followed by an in vitro enzyme assay showed that this synthase converts FPP into (+)-valencene (49.5% of total product) and (−)-7-epi-alpha-selinene (35.5% of total product) along with five minor products (Lucker et al. Phytochemistry (2004) 65: 2649-2659).

Besides the above enzymes with biochemically proven valencene synthase activity, the GenBank nucleic acid sequence database contains yet another entry annotated as a valencene synthase, i.e. the *Perilla frutescens* var. *frutescens* valencene synthase gene (accession number AY917195). In literature, however, nothing has been reported on this specific putative valencene synthase, so a biochemical proof for its activity and specificity is lacking.

Thus, there is a need for an alternative valencene synthase which may be used in the preparation of valencene. In particular there is a need for an alternative valencene synthase that displays an improved expression, at least in selected host cells; an alternative valencene synthase that has a high enzymatic activity at least under specific conditions, such as at a neutral or alkaline pH and/or intracellularly in the cell wherein it has been produced; and/or an alternative valencene synthase that is highly specific, in particular that has improved specificity compared to valencene synthase from *Citrus×paradisi*, with respect to catalysing the conversion of FPP into valencene, at least under specific conditions, such as at about neutral or at alkaline pH and/or intracellularly in the cell wherein it has been produced.

It has been found that a specific polypeptide that was hitherto unknown has valencene synthase activity and that this polypeptide can be used as a catalyst that may serve as an alternative to known valencene synthases.

Accordingly, the present invention relates to a valencene synthase comprising an amino acid sequence as shown in SEQ ID NO: 2, SEQ ID NO: 4, or a functional homologue thereof, said functional homologue being a valencene synthase comprising an amino acid sequence which has a sequence identity of at least 40%, preferably of at least 50% with SEQ ID NO: 2 or SEQ ID NO: 4. Said homologue may in particular be a valencene synthase comprising an amino acid sequence which has a sequence identity of at least 55%, at least 60%, at least 70%, at least 75%, at least 80%, at least 85%, at least 90%, at least 95%, at least 98% or at least 99% with SEQ ID NO: 2 or SEQ ID NO: 4.

Further, the invention relates to an antibody having binding affinity to a valencene synthase according to the invention. An antibody according to the invention thus specifically binds to a valencene synthase according to the invention.

Further, the invention relates to a protein displaying immunological cross-reactivity with an antibody raised against a fragment of the amino acid sequence according to SEQ ID: NO. 2 or SEQ ID: NO. 4, in particular such a protein having valencene synthase activity.

The immunological cross reactivity may be assayed using an antibody raised against, or reactive with, at least one epitope of an isolated polypeptide according to the present invention having valencene synthase activity. The antibody, which may either be monoclonal or polyclonal, may be produced by methods known in the art, e.g. as described by Hudson et al., Practical Immunology, Third Edition (1989), Blackwell Scientific Publications. The immunochemical cross-reactivity may be determined using assays known in the art, an example of which is Western blotting, e.g. as described in Hudson et al., Practical Immunology, Third Edition (1989), Blackwell Scientific Publications.

The invention further relates to a nucleic acid, comprising a nucleic acid sequence encoding a valencene synthase according to the invention, or comprising a nucleic acid sequence complementary to said encoding sequence. In particular, the nucleic acid may be selected from nucleic acids comprising a nucleic acid sequence as shown in SEQ ID NO: 1, SEQ ID NO: 3, SEQ ID NO: 18, SEQ ID NO: 19 and other nucleic acid sequences encoding a valencene synthase according to the invention, said other sequences comprising a nucleic acid sequence having a sequence identity of at least 50%, in particular of at least 60%, at least 70%, at least 80%, at least 85%, at least 90%, at least 95%, at least 98% or at least 99% with the nucleic acid sequence shown in SEQ ID NO: 1, SEQ ID NO: 3, SEQ ID NO: 18 or SEQ ID NO: 19, respectively nucleic acids complementary thereto. Said other nucleic acid sequence encoding a valencene synthase according to the invention may herein after be referred to as a functional analogue.

The present invention also relates to a nucleic acid, comprising a nucleic acid sequence encoding a valencene synthase according to the invention, which hybridizes under low stringency conditions, preferably under medium stringency conditions, more preferably under high stringency conditions and most preferably under very high stringency conditions with the nucleic acid sequence shown in SEQ ID NO: 1, SEQ ID NO: 3, SEQ ID NO: 18 or SEQ ID NO: 19, respectively nucleic acids complementary thereto.

Hybridization experiments can be performed by a variety of methods, which are well available to the skilled man. General guidelines for choosing among these various methods can be found in e.g. Sambrook, J., and Russell, D. W. Molecular Cloning: A Laboratory Manual. 3d ed., Cold Spring Harbor Laboratory Press, Cold Spring Harbor, N.Y., (2001).

With stringency of the hybridization conditions is meant, the conditions under which the hybridization, consisting of the actual hybridization and wash steps, are performed. Wash steps are used to wash off the nucleic acids, which do not hybridize with the target nucleic acid immobilized on for example a nitrocellulose filter. The stringency of the hybridization conditions can for example be changed by changing the salt concentration of the wash solution and/or by changing the temperature under which the wash step is performed (wash temperature). Stringency of the hybridization increases by lowering the salt concentration in the wash solution or by raising the wash temperature. For purpose of this application, low, medium, high and very high stringency conditions are in particular the following conditions and equivalents thereof: the hybridization is performed in an aqueous solution comprising 6×SSC (20×SSC stock solution is 3.0 M NaCl and 0.3 M trisodium citrate in water), 5×Denhardt's reagent (100× Denhardt's reagent is 2% (w/v) BSA Fraction V, 20% (w/v) Ficoll 400 and 2% (w/v) polyvinylpyrrollidone in water), 0.5% SDS and 100 µg/mL denaturated, fragmented salmon sperm DNA, at about 45° C. for about 12 hours. After removal of non-bonded nucleic acid probe by two consecutive 5 minutes wash steps in 2×SSC, 0.1% SDS at room temperature, execution of two consecutive 5 minutes wash steps in 0.2× SSC, 0.1% SDS at room temperature is an example of low stringency, of two consecutive 15 minutes wash steps in 0.2× SSC, 0.1% SDS at 42° C. an example of medium stringency, of two consecutive 15 minutes wash steps in 0.1×SSC, 0.1% SDS at 55° C. an example of high stringency, and two consecutive 30 minutes wash steps in 0.1×SSC, 0.1% SDS at 68° C. an example of very high stringency.

A valencene synthase or nucleic acid according to the invention may be a natural compound or fragment of a compound isolated from its natural source (e.g. *Chamaecyparis nootkatensis*), be a chemically or enzymatically synthesised compound or fragment of a compound or a compound or fragment of a compound produced in a recombinant cell, in which recombinant cell it may be present or from which cell it may have been isolated.

The invention further relates to an expression vector comprising a nucleic acid according to the invention.

The invention further relates to a host cell, comprising an expression vector according to the invention.

The invention further relates to a method for preparing valencene, comprising converting FPP to valencene in the presence of a valencene synthase according to the invention. Four different geometric isomers of FPP can exist, i.e. 2E,6E-FPP, 2Z,6E-FPP, 2E,6Z-FPP, and 2Z,6Z-FPP. Good results have been obtained with 2E,6E-FPP, although in principle any other isomer of FPP may be a suitable substrate for an enzyme according to the invention.

The invention further relates to a method for preparing nootkatone, wherein valencene prepared in a method according to the invention is converted into nootkatone.

The invention is further directed to a method for producing a valencene synthase according to the invention, comprising culturing a host cell according to the invention under conditions conducive to the production of the valencene synthase and recovering the valencene synthase from the host cell.

Of a valencene synthase according to the invention it has been found that it is more specific towards valencene synthesis than a valencene synthase from citrus, in particular at or around neutral pH in an in vitro assay or in a method wherein valencene is synthesised intracellularly in a host cell genetically modified to produce a valencene synthase according to the invention and a citrus valencene synthase, respectively. Initial results show that under identical conditions, the amount of major side product (germacrene A) formed with the novel enzyme of the invention is significantly lower, namely a molar ratio valencene:germacrene A of 4:1 compared to 2:1 with the citrus valencene synthase.

In accordance with the invention it has been found possible to bring the valencene synthase to expression with good yield in distinct organisms. For instance, the valencene synthase has been found to be expressed well in *E. coli* and in *Saccharomyces cerevisiae* (baker's yeast). Also it has been found that in a method according to the invention wherein a valencene synthase according to the invention is expressed in an isoprenoid producing host organism (*Rhodobacter sphaeroides*) the valencene production is higher than in a comparative method wherein a citrus valencene synthase is expressed.

Thus, in an advantageous embodiment, the present invention provides a valencene synthase with improved specificity towards the catalysis of valencene synthesis and an improved production rate, when used in a method for preparing valencene, in particular compared to valencene synthase from citrus or another valencene synthase according to the prior art, cited herein.

Without being bound by theory, it is thought that a high specificity towards the catalysis of valencene synthesis at neutral or mildly alkaline pH is in particular considered desirable for methods wherein the valencene is prepared intracellularly, because various host cells are thought to have a neutral or slightly alkaline intracellular pH, such as a pH of 7.0-8.5 (for intracellular pH values of bacteria, see for instance: Booth, Microbiological Reviews (1985) 49: 359-378). When, for instance, *E. coli* cells were exposed to pH values ranging from 5.5 to 8.0, the intracellular pH was between 7.1 and 7.9 (Olsen et al., Appl. Environ. Microbiol. (2002) 68: 4145-4147). This may explain an improved specificity towards the synthesis of valencene of a valencene synthase according to the invention, also intracellularly.

The term "or" as used herein is defined as "and/or" unless specified otherwise.

The term "a" or "an" as used herein is defined as "at least one" unless specified otherwise.

When referring to a noun (e.g. a compound, an additive, etc.) in the singular, the plural is meant to be included.

The terms farnesyl diphosphate and farnesylpyrophosphate (both abbreviated as FPP) as interchangeably used herein refer to the compound 3,7,11-trimethyl-2,6,10-dodecatrien-1-yl pyrophosphate and include all known isomers of this compound.

The term "recombinant" in relation to a recombinant cell, vector, nucleic acid or the like as used herein, refers to a cell, vector, nucleic acid or the like, containing nucleic acid not naturally occurring in that cell, vector, nucleic acid or the like and/or not naturally occurring at that same location. Generally, said nucleic acid has been introduced into that strain (cell) using recombinant DNA techniques.

The term "heterologous" when used with respect to a nucleic acid (DNA or RNA) or protein refers to a nucleic acid or protein that does not occur naturally as part of the organism, cell, genome or DNA or RNA sequence in which it is present, or that is found in a cell or location or locations in the genome or DNA or RNA sequence that differ from that in which it is found in nature. Heterologous nucleic acids or proteins are not endogenous to the cell into which they are introduced, but have been obtained from another cell or synthetically or recombinantly produced. Generally, though not necessarily, such nucleic acids encode proteins that are not normally produced by the cell in which the DNA is expressed.

A gene that is endogenous to a particular host cell but has been modified from its natural form, through, for example, the use of DNA shuffling, is also called heterologous. The term "heterologous" also includes non-naturally occurring multiple copies of a naturally occurring DNA sequence. Thus, the term "heterologous" may refer to a DNA segment that is foreign or heterologous to the cell, or homologous to the cell but in a position and/or a number within the host cell nucleic acid in which the segment is not ordinarily found. Exogenous DNA segments are expressed to yield exogenous polypeptides. A "homologous" DNA sequence is a DNA sequence that is naturally associated with a host cell into which it is introduced.

Any nucleic acid or protein that one of skill in the art would recognize as heterologous or foreign to the cell in which it is expressed is herein encompassed by the term heterologous nucleic acid or protein.

The term "mutated" or "mutation" as used herein regarding proteins or polypeptides means that at least one amino acid in the wild-type or naturally occurring protein or polypeptide sequence has been replaced with a different amino acid, or deleted from, or inserted into the sequence via mutagenesis of nucleic acids encoding these amino acids. Mutagenesis is a well-known method in the art, and includes, for example, site-directed mutagenesis by means of PCR or via oligonucleotide-mediated mutagenesis as described in Sambrook, J., and Russell, D. W. Molecular Cloning: A Laboratory Manual. 3d ed., Cold Spring Harbor Laboratory Press, Cold Spring Harbor, N.Y., (2001). The term "mutated" or "mutation" as used herein regarding genes means that at least one nucleotide in the nucleotide sequence of that gene or a regulatory sequence thereof, has been replaced with a different nucleotide, or has been deleted from or inserted into the sequence via mutagenesis.

The terms "open reading frame" and "ORF" refer to the amino acid sequence encoded between translation initiation and termination codons of a coding sequence. The terms "initiation codon" and "termination codon" refer to a unit of three adjacent nucleotides ('codon') in a coding sequence that specifies initiation and chain termination, respectively, of protein synthesis (mRNA translation).

The term "gene" is used broadly to refer to any segment of nucleic acid associated with a biological function. Thus, genes include coding sequences and/or the regulatory sequences required for their expression. For example, gene refers to a nucleic acid fragment that expresses mRNA or functional RNA, or encodes a specific protein, and which includes regulatory sequences. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

The term "chimeric gene" refers to any gene that contains 1) DNA sequences, including regulatory and coding sequences, that are not found together in nature, or 2) sequences encoding parts of proteins not naturally adjoined, or 3) parts of promoters that are not naturally adjoined. Accordingly, a chimeric gene may comprise regulatory sequences and coding sequences that are derived from different sources, or comprise regulatory sequences and coding sequences derived from the same source, but arranged in a manner different from that found in nature.

The term "transgenic" for a transgenic cell or organism as used herein, refers to an organism or cell (which cell may be an organism per se or a cell of a multi-cellular organism from which it has been isolated) containing a nucleic acid not naturally occurring in that organism or cell and which nucleic acid has been introduced into that organism or cell (i.e. has been introduced in the organism or cell itself or in an ancestor of the organism or an ancestral organism of an organism of which the cell has been isolated) using recombinant DNA techniques.

A "transgene" refers to a gene that has been introduced into the genome by transformation and preferably is stably maintained. Transgenes may include, for example, genes that are either heterologous or homologous to the genes of a particular plant to be transformed. Additionally, transgenes may comprise native genes inserted into a non-native organism, or chimeric genes. The term "endogenous gene" refers to a native gene in its natural location in the genome of an organism. A "foreign" gene refers to a gene not normally found in the host organism but that is introduced by gene transfer.

"Transformation" and "transforming", as used herein, refers to the introduction of a heterologous nucleotide sequence into a host cell, irrespective of the method used for the insertion, for example, direct uptake, transduction, conjugation, f-mating or electroporation. The exogenous polynucleotide may be maintained as a non-integrated vector, for example, a plasmid, or alternatively, may be integrated into the host cell genome.

"Coding sequence" refers to a DNA or RNA sequence that codes for a specific amino acid sequence and excludes the non-coding sequences. It may constitute an "uninterrupted coding sequence", i.e. lacking an intron, such as in a cDNA or it may include one or more introns bound by appropriate splice junctions. An "intron" is a sequence of RNA which is contained in the primary transcript but which is removed through cleavage and re-ligation of the RNA within the cell to create the mature mRNA that can be translated into a protein.

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences which may be a combination of synthetic and natural sequences. As is noted above, the term "suitable regulatory sequences" is not limited to promoters.

Examples of regulatory sequences include promoters (such as transcriptional promoters, constitutive promoters, inducible promoters), operators, or enhancers, mRNA ribosomal binding sites, and appropriate sequences which control transcription and translation initiation and termination. Nucleic acid sequences are "operably linked" when the regulatory sequence functionally relates to the cDNA sequence of the invention.

Each of the regulatory sequences may independently be selected from heterologous and homologous regulatory sequences.

"Promoter" refers to a nucleotide sequence, usually upstream (5') to its coding sequence, which controls the expression of said coding sequence by providing the recognition for RNA polymerase and other factors required for proper transcription. "Promoter" includes a minimal promoter that is a short DNA sequence comprised of a TATA box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors which control the effectiveness of transcription initiation in response to physiological or developmental conditions.

The term "nucleic acid" as used herein, includes reference to a deoxyribonucleotide or ribonucleotide polymer, i.e. a polynucleotide, in either single-or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are "polynucleotides" as the term is used herein. It will be appreciated that a great variety of modifications have been made to DNA and RNA that serve many useful purposes known to those of skill in the art. The term "polynucleotide" as it is employed herein embraces such chemically, enzymatically or metabolically modified forms of polynucleotides, as well as the chemical forms of DNA and RNA characteristic of viruses and cells, including among other things, simple and complex cells.

Every nucleic acid sequence herein that encodes a polypeptide also, by reference to the genetic code, describes every possible silent variation of the nucleic acid. The term "conservatively modified variants" applies to both amino acid and nucleic acid sequences. With respect to particular nucleic acid sequences, the term "conservatively modified variants" refers to those nucleic acids which encode identical or conservatively modified variants of the amino acid sequences due to the degeneracy of the genetic code. The term "degeneracy of the genetic code" refers to the fact that a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulphation, gamma-carboxylation of glutamic acid residues, hydroxylation and ADP-ribosylation.

Within the context of the present application, oligomers (such as oligonucleotides, oligopeptides) are considered a species of the group of polymers. Oligomers have a relatively low number of monomeric units, in general 2-100, in particular 6-100.

"Expression cassette" as used herein means a DNA sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one which is naturally occurring but has been obtained in a recombinant form useful for heterologous expression. The expression of the nucleotide sequence in the expression cassette may be under the control of a constitutive promoter or of an inducible promoter which initiates transcription only when the host cell is exposed to some particular external stimulus. In the case of a multicellular organism, the promoter can also be specific to a particular tissue or organ or stage of development.

The term "vector" as used herein refers to a construction comprised of genetic material designed to direct transformation of a targeted cell. A vector contains multiple genetic elements positionally and sequentially oriented, i.e., operatively linked with other necessary elements such that the nucleic acid in a nucleic acid cassette can be transcribed and when necessary, translated in the transformed cells.

In particular, the vector may be selected from the group of viral vectors, (bacterio)phages, cosmids or plasmids. The vector may also be a yeast artificial chromosome (YAC), a bacterial artificial chromosome (BAC) or *Agrobacterium* binary vector. The vector may be in double or single stranded linear or circular form which may or may not be self transmissible or mobilizable, and which can transform prokaryotic or eukaryotic host either by integration into the cellular genome or exist extrachromosomally (e.g. autonomous replicating plasmid with an origin of replication). Specifically included are shuttle vectors by which is meant a DNA vehicle capable, naturally or by design, of replication in two different host organisms, which may be selected from actinomycetes and related species, bacteria and eukaryotic (e.g. higher plant, mammalian, yeast or fungal cells). Preferably the nucleic acid in the vector is under the control of, and operably linked to, an appropriate promoter or other regulatory elements for transcription in a host cell such as a microbial, e.g. bacterial, or plant cell. The vector may be a bi-functional expression vector which functions in multiple hosts. In the case of genomic DNA, this may contain its own promoter or other regulatory elements and in the case of cDNA this may be under the control of an appropriate promoter or other regulatory elements for expression in the host cell.

Vectors containing a polynucleic acid according to the invention can be prepared based on methodology known in the art per se. For instance use can be made of a cDNA sequence encoding the polypeptide according to the invention operably linked to suitable regulatory elements, such as transcriptional or translational regulatory nucleic acid sequences.

The term "vector" as used herein, includes reference to a vector for standard cloning work ("cloning vector") as well as to more specialized type of vectors, like an (autosomal) expression vector and a cloning vector used for integration into the chromosome of the host cell ("integration vector").

"Cloning vectors" typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector.

The term "expression vector" refers to a DNA molecule, linear or circular, that comprises a segment encoding a polypeptide of interest under the control of (i.e. operably linked to) additional nucleic acid segments that provide for its transcription. Such additional segments may include promoter and terminator sequences, and may optionally include one or more origins of replication, one or more selectable markers, an enhancer, a polyadenylation signal, and the like. Expression vectors are generally derived from plasmid or viral DNA, or may contain elements of both. In particular an expression vector comprises a nucleotide sequence that comprises in the 5' to 3' direction and operably linked: (a) a transcription and translation initiation region that are recognized by the host organism, (b) a coding sequence for a polypeptide of interest, and (c) a transcription and translation termination region that are recognized by the host organism. "Plasmid" refers to autonomously replicating extrachromosomal DNA which is not integrated into a microorganism's genome and is usually circular in nature.

An "integration vector" refers to a DNA molecule, linear or circular, that can be incorporated into a microorganism's genome and provides for stable inheritance of a gene encoding a polypeptide of interest. The integration vector generally comprises one or more segments comprising a gene sequence encoding a polypeptide of interest under the control of (i.e., operably linked to) additional nucleic acid segments that provide for its transcription. Such additional segments may include promoter and terminator sequences, and one or more segments that drive the incorporation of the gene of interest into the genome of the target cell, usually by the process of homologous recombination. Typically, the integration vector will be one which can be transferred into the target cell, but which has a replicon which is nonfunctional in that organism. Integration of the segment comprising the gene of interest may be selected if an appropriate marker is included within that segment.

As used herein, the term "operably linked" or "operatively linked" refers to a juxtaposition wherein the components so described are in a relationship permitting them to function in their intended manner. A control sequence "operably linked" to another control sequence and/or to a coding sequence is ligated in such a way that transcription and/or expression of the coding sequence is achieved under conditions compatible with the control sequence. Generally, operably linked means that the nucleic acid sequences being linked are contiguous and, where necessary to join two protein coding regions, contiguous and in the same reading frame.

The term "valencene synthase" is used herein for polypeptides having catalytic activity in the formation of valencene from farnesyl diphosphate, and for other moieties comprising such a polypeptide. Examples of such other moieties include complexes of said polypeptide with one or more other polypeptides, other complexes of said polypeptides (e.g. metalloprotein complexes), macromolecular compounds comprising said polypeptide and another organic moiety, said polypeptide bound to a support material, etc. The valencene synthase can be provided in its natural environment, i.e. within a cell in which it has been produced, or in the medium into which it has been excreted by the cell producing it. It can also be provided separate from the source that has produced the polypeptide and can be manipulated by attachment to a carrier, labeled with a labeling moiety, and the like.

The term "functional homologue" of a sequence, or in short "homologue", as used herein, refers to a polypeptide comprising said specific sequence with the proviso that one or more amino acids are substituted, deleted, added, and/or inserted, and which polypeptide has (qualitatively) the same enzymatic functionality for substrate conversion in case the term 'functional homologue' is used for an enzyme, i.e. a homologue of the sequence with SEQ ID NO: 2 or SEQ ID NO: 4 having catalytic activity in the formation of valencene from farnesyl diphosphate. In the examples a test is described that is suitable to verify whether a polypeptide or a moiety comprising a polypeptide is a valencene synthase ("Valencene synthase activity test"). Moreover; the skilled artisan recognises that equivalent nucleotide sequences encompassed by this invention can also be defined by their ability to hybridize, under low, moderate and/or stringent conditions, with the nucleotide sequences that are within the literal scope of the instant claims.

A preferred homologue to SEQ ID NO: 2 or SEQ ID NO: 4 according to the invention has a specificity towards catalysis of valencene formation, expressed as the molar ratio valencene to germacrene A (a known side-product, formed in known valencene synthase catalysed reactions) of at least 3:1, in particular of at least 4:1, when determined at pH 7, using the valencene synthase activity test described herein below in the Examples (using a purified polypeptide). Said ratio may be infinite (1:0; i.e. no detectable amount of germacrene A formed), or up to 100:1, or up to 10:1 or up to 5:1.

Sequence identity or similarity is defined herein as a relationship between two or more polypeptide sequences or two or more nucleic acid sequences, as determined by comparing those sequences. Usually, sequence identities or similarities are compared over the whole length of the sequences, but may however also be compared only for a part of the sequences aligning with each other. In the art, "identity" or "similarity" also means the degree of sequence relatedness between polypeptide sequences or nucleic acid sequences, as the case may be, as determined by the match between such sequences. Sequence identity as used herein is the value as determined by the EMBOSS Pairwise Alignment Algoritm "Needle", for instance at the server of the European Bioinformatics Institute. (HyperText Transfer Protocol://worldwideweb.ebi-.ac.uk/Tools/emboss/align/). For alignment of amino acid sequences the default parameters are: Matrix =Blosum62; Open Gap Penalty =10.0; Gap Extension Penalty =0.5. For alignment of nucleic acid sequences the default parameters are: Matrix =DNAfull; Open Gap Penalty =10.0; Gap Extension Penalty =0.5.

Discrepancies between a valencene synthase according to SEQ ID NO: 2 or SEQ ID NO: 4 or a nucleic acid according to SEQ ID NO: 1 or SEQ ID NO: 3 on hand and a functional homologue of said valencene synthase may in particular be the result of modifications performed, e.g. to improve a property of the valencene synthase or polynucleic acid (e.g. improved expression) by a biological technique known to the skilled person in the art, such as e.g. molecular evolution or rational design or by using a mutagenesis technique known in the art (random mutagenesis, site-directed mutagenesis, directed evolution, gene recombination, etc.). The valencene synthase's or the nucleic acid's sequence may be altered compared to the sequences of SEQ ID NO: 2 or SEQ ID NO: 4 and SEQ ID NO: 1 or SEQ ID NO: 3, respectively, as a result of one or more natural occurring variations. Examples of such natural modifications/variations are differences in glycosylation (more broadly defined as "post-translational modifications"), differences due to alternative splicing, and single-nucleic acid polymorphisms (SNPs). The nucleic acid may be modified such that it encodes a polypeptide that differs by at least one amino acid from the polypeptide of SEQ ID NO: 2 or SEQ ID NO: 4, so that it encodes a polypeptide comprising one or more amino acid substitutions, deletions and/or insertions compared to SEQ ID NO: 2 or SEQ ID NO: 4, which polypeptide still has valencene synthase activity. Further, use may be made of codon optimisation or codon pair optimisation, e.g. based on a method as described in WO 2008/000632 or as offered by commercial DNA synthesizing companies like DNA2.0, Geneart, and GenScript. Examples of codon optimised sequences include SEQ ID NO: 18 and SEQ ID NO: 19.

One or more sequences encoding appropriate signal peptides that are not naturally associated with the polypeptides of the invention can be incorporated into (expression) vectors. For example, a DNA sequence for a signal peptide leader can be fused in-frame to a nucleic acid sequence of the invention so that the polypeptide of the invention is initially translated as a fusion protein comprising the signal peptide. Depending on the nature of the signal peptide, the expressed polypeptide will be targeted differently. A secretory signal peptide that is functional in the intended host cells, for instance, enhances extracellular secretion of the expressed polypeptide. Other signal peptides direct the expressed polypeptides to certain organelles, like the chloroplasts, mitochondria and peroxisomes. The signal peptide can be cleaved from the polypeptide upon transportation to the intended organelle or from the cell. It is possible to provide a fusion of an additional peptide sequence at the amino or carboxyl terminal end of a polypeptide according to SEQ ID NO: 2 or SEQ ID NO: 4 or homologue thereof.

As mentioned above the invention further relates to a host cell comprising a vector according to the invention. By "host cell" is meant a cell which contains a vector and supports the replication and/or expression of the vector.

The nucleic acid of the invention is heterologous to the host cell. The host cell may be a prokaryotic cell, a eukaryotic cell or a cell from a member of the Archaea. The host cell may be from any organism, in particular any non-human organism. In particular the host cell may be selected from bacterial cells, fungal cells, archaea, protists, plant cells (including algae), cells originating from an animal (in particular isolated from said animal). The host cell may form part of a multicellular organism, other than human or the organism from which the enzyme naturally originates (such as *Chamaecyparis nootkatensis* in case of the valencene synthase of SEQ ID NO: 4). In a specific embodiment, host cells of the invention are in a culture of cells originating from a multicellular organism, yet isolated there from.

In general, the host cell is an organism comprising genes for expressing the enzymes for catalysing the reaction steps of the mevalonate pathway or another metabolic pathway (such as the deoxyxylulose-5-phosphate (DXP) pathway) enabling the production of the C5 prenyl diphosphates isopentenyl diphosphate (IPP) and dimethylallyl diphosphate (DMAPP), which are the universal isoprenoid building blocks. As far as known, unless specific genes have been knocked-out, all known organisms comprise such a pathway. Eukaryotes generally are naturally capable of preparing IPP via the mevalonate pathway. This IPP is then isomerized into DMAPP by the action of the enzyme isopentenyl diphosphate isomerase (Idi). The DXP pathway, which is furnishing IPP and DMAPP in a 5:1 ratio, is common to prokaryotes, although several prokaryotes are naturally capable of preparing IPP via the mevalonate pathway. These pathways are known in the art, and have been described, e.g., by Withers & Keasling in Appl. Microbiol. Biotechnol. (2007) 73: 980-990, of which the contents with respect to the description of these pathways, and in particular FIG. 1 and the enzymes mentioned in said publication that play a role in one or both of said pathways, are enclosed by reference. The genes of these pathways may each independently be homologous or heterologous to the cell.

The host cells further will, either endogenically or from heterologous sources, comprise one or more genes for expressing enzymes with prenyl transferase activity catalysing the head-to-tail condensation of the C5 prenyl diphosphates producing longer prenyl diphosphates. The universal sesquiterpene precursor farnesyl diphosphate (FPP), for instance, is formed by the action of these enzymes through the successive head-to-tail addition of 2 molecules of IPP to 1 molecule of DMAPP.

In an embodiment, the host cell is a bacterium. The bacterium may be gram-positive or gram-negative. Gram-positive bacteria may be selected from the genera of *Bacillus* and *Lactobacillus*, in particular from the species of *Bacillus subtilis* and *Lactobacillus casei*.

In a preferred embodiment, the bacterium is selected from the group of gram-negative bacteria, in particular from the group of *Rhodobacter*, *Paracoccus* and *Escherichia*, more in particular from the group of *Rhodobacter capsulatus*, *Rhodobacter sphaeroides*, *Paracoccus carotinifaciens*, *Paracoccus zeaxanthinifaciens* and *Escherichia coli*. *Rhodobacter sphaeroides* is an example of an organism naturally containing all genes needed for expressing enzymes catalysing the various reaction steps in the DXP pathway, enabling the intracellular production of IPP and DMAPP.

In an embodiment, the host cell is a fungal cell, in particular a fungal cell selected from the group of *Aspergillus*, *Blakeslea*, *Penicillium*, *Phaffia* (*Xanthophyllomyces*), *Pichia*, *Saccharomyces* and *Yarrowia*, more in particular from the group of *Aspergillus nidulans*, *Aspergillus niger*, *Aspergillus oryzae*, *Blakeslea trispora*, *Penicillium chrysogenum*, *Phaffia rhodozyma* (*Xanthophyllomyces dendrorhous*), *Pichia pastoris*, *Saccharomyces cerevisiae* and *Yarrowia lipolytica*.

It is also possible to express the nucleic acids of the invention in cells derived from higher eukaryotic organisms, such as plant cells and animal cells, such as insect cell, or cells from mouse, rat or human. Said cells can be maintained in a cell or tissue culture and be used for in vitro production of valencene synthase.

A multicellular organism comprising host cells according to the invention may in particular be selected from the group of multicellular plants and mushrooms (*Basidiomycetes*).

Thus, in a specific embodiment, the invention relates to a transgenic plant or plant cell or tissue culture comprising transgenic plant cells, said plant or culture comprising plant host cells according to the invention. The transgenic plant or culture of transgenic plant cells may in particular be selected from *Nicotiana* spp., *Solanum* spp., *Cichorum intybus*, *Lactuca sativa*, *Mentha* spp., *Artemisia annua*, tuber forming plants, such as *Helianthus tuberosus*, cassava and *Beta vulgaris*, oil crops, such as *Brassica* spp., *Elaeis* spp. (oil palm tree), *Helianthus annuus*, *Glycine max* and *Arachis hypogaea*, liquid culture plants, such as duckweed *Lemna* spp., tobacco BY2 cells and *Physcomitrella patens*, trees, such as pine tree and poplar, respectively a cell culture or a tissue culture of any of said plants. In a specific embodiment, the tissue culture is a hairy root culture.

In a further specific embodiment the invention relates to a transgenic mushroom or culture comprising transgenic mushroom cells. The transgenic mushroom or culture comprising transgenic host cells, may in particular be selected from the group of *Schizophyllum*, *Agaricus* and *Pleurotus*, more in particular from *Schizophyllum commune*, the common mushroom (*Agaricus bisporus*), the oyster mushroom (*Pleurotus ostreotus* and *Pleurotus sapidus*), respectively a culture comprising cells of any of said mushrooms. One additional advantage for using mushrooms to express the valencene synthase is that at least some mushrooms are able to convert valencene into nootkatone (Fraatz, M. A. et al., J. Mol. Catal. B: Enzym. (2009) 61: 202-207).

Next to the production of valencene per se, expression of valencene synthase according to the invention and production of valencene in plants or mushrooms also provides resistance in these organisms. First of all, valencene is known to act as an insect repellent and is active against insects such as mosquitoes, cockroaches, ticks, fleas, termites and *Drosophila*. Further, valencene has been shown to make plants resistant to pathogens, such as the fungus *Phytophthora*, especially *P. ramorum* (Sudden oak death agent) (Manter, D. K. et al., Forest Pathology (2006) 36: 297-308).

A host cell according to the invention may be produced based on standard genetic and molecular biology techniques that are generally known in the art, e.g. as described in Sambrook, J., and Russell, D. W. "Molecular Cloning: A Laboratory Manual" 3d ed., Cold Spring Harbor Laboratory Press, Cold Spring Harbor, N.Y., (2001); and F. M. Ausubel et al, eds., "Current protocols in molecular biology", John Wiley and Sons, Inc., New York (1987), and later supplements thereto.

Methods to transform *Basidiomycetes* are known from, for example, Alves et al. (App). Environ. Microbiol. (2004) 70: 6379-6384), Godio et al. (Curr. Genet. (2004) 46: 287-294), Schuurs et al. (Genetics (1997) 147: 589-596), and WO 06/096050. To achieve expression of a suitable valencene synthase gene in basidiomycetes, its complete open reading frame is typically cloned into an expression vector suitable for transformation of basidiomycetes. The expression vector preferably also comprises nucleic acid sequences that regulate transcription initiation and termination. It is also preferred to incorporate at least one selectable marker gene to allow for selection of transformants. Expression of a valencene synthase can be achieved using a basidiomycete promoter, e.g. a constitutive promoter or an inducible promoter. An example of a strong constitutive promoter is the glyceraldehyde-3-phosphate dehydrogenase (gpdA) promoter. This promoter is preferred for constitutive expression when recombinant DNA material is expressed in a basidiomycete host. Other examples are the phosphoglycerate kinase (pgk) promoter, the pyruvate kinase (pki) promoter, TPI, the triose phosphate isomerase (tpi) promoter, the APC synthetase subunit g (oliC) promoter, the sc3 promoter and the acetamidase (amdS) promoter of a basidiomycete (WO 96/41882).

If needed, the primary nucleotide sequence of the valencene synthase gene can be adapted to the codon usage of the basidiomycete host. Further, expression can be directed especially to the (monokaryotic) mycelium or to the (dikaryotic) fruiting bodies. In the latter case, the Fbh1 promoter of Pleurotis is especially useful (Penas, M. M. et al., Mycologia (2004) 96: 75-82).

Methodologies for the construction of plant transformation constructs are described in the art. Overexpression can be achieved by insertion of one or more than one extra copy of the selected gene. It is not unknown for plants or their progeny, originally transformed with one or more than one extra copy of a nucleotide sequence to exhibit overexpression.

Obtaining sufficient levels of transgenic expression in the appropriate plant tissues is an important aspect in the production of genetically engineered crops. Expression of heterologous DNA sequences in a plant host is dependent upon the presence of an operably linked promoter that is functional within the plant host. Choice of the promoter sequence will determine when and where within the organism the heterologous DNA sequence is expressed. Although many promoters from dicotyledons have been shown to be operational in monocotyledons and vice versa, ideally dicotyledonous promoters are selected for expression in dicotyledons, and monocotyledonous promoters for expression in monocotyledons. However, there is no restriction to the provenance of selected promoters; it is sufficient that they are operational in driving the expression of the nucleotide sequences in the desired cell or tissue. In some cases, expression in multiple tissues is desirable, and constitutive promoters such as the 35S promoter series may be used in this respect. However, in some of the embodiments of the present invention it is preferred that the expression in transgenic plants is leaf-specific, more preferably, the expression of the gene occurs in the leaf plastids. The promoter of the isoprene synthase gene from *Populus alba* (PaIspS) (Sasaki et al., FEBS Letters (2005) 579: 2514-2518) appears to drive plastid-specific expression. Hence, this promoter is a very suitable promoter for use in an expression vector of the present invention.

Other suitable leaf-specific promoters are the rbcS (Rubisco) promoter (e.g. from coffee, see WO 02/092822); from *Brassica*, see U.S. Pat. No. 7,115,733; from soybean, see Dhanker, O., et al., Nature Biotechnol. (2002) 20: 1140-1145), the cy-FBPase promoter (see U.S. Pat. No. 6,229,067), the promoter sequence of the light-harvesting chlorophyll a/b binding protein from oil-palm (see US 2006/0288409), the STP3 promoter from *Arabidopsis thaliana* (see, Buttner, M. et al., Plant cell & Environ. (2001) 23: 175-184), the promoter of the bean PAL2 gene (see Sablowski, R. W. et al., Proc. Natl. Acad. Sci. USA (1995) 92: 6901-6905), enhancer sequences of the potato ST-LS1 promoter (see Stockhaus, J. et al., Proc. Natl. Acad. Sci. USA (1985) 84: 7943-7947), the wheat CAB1 promoter (see Gotor, C. et al., Plant J. (1993) 3: 509-518), the stomata-specific promoter from the potato ADP-glucose-phosphorylase gene (see U.S. Pat. No. 5,538,879), the LPSE1 element from the P(D540) gene of rice (see CN 2007/10051443), and the stomata specific promoter, pGC/(At1g22690) from *Arabidopsis thaliana* (see Yang, Y. et al., Plant Methods (2008) 4: 6).

Plant species may, for instance, be transformed by the DNA-mediated transformation of plant cell protoplasts and subsequent regeneration of the plant from the transformed protoplasts in accordance with procedures well known in the art.

Further examples of methods of transforming plant cells include microinjection (Crossway et al., Mol. Gen. Genet. (1986) 202: 179-185), electroporation (Riggs, C. D. and Bates, G. W., Proc. Natl. Acad. Sci. USA (1986), 83: 5602-5606), *Agrobacterium*-mediated transformation (Hinchee et al., Bio/Technol. (1988) 6: 915-922), direct gene transfer (Paszkowski, J. et al., EMBO J. (1984) 3: 2717-2722), and ballistic particle acceleration using devices available from Agracetus, Inc., Madison, Wis. and BioRad, Hercules, Calif. (see, for example, Sanford et al., U.S. Pat. No. 4,945,050 and European Patent Application EP 0 332 581).

It is also possible to employ the protoplast transformation method for maize (European Patent Application EP 0 292 435, U.S. Pat. No. 5,350,689).

It is particularly preferred to use the binary type vectors of Ti and Ri plasmids of *Agrobacterium* spp. Ti-derived vectors transform a wide variety of higher plants, including monocotyledonous and dicotyledonous plants, such as soybean, cotton, rape, tobacco, and rice (Pacciotti et al., Bio/technol. (1985) 3: 241; Byrne M. C. et al., Plant Cell Tissue and Organ Culture (1987) 8: 3-15; Sukhapinda, K. et al., Plant Mol. Biol. (1987) 8: 209-217; Hiei, Y. et al., The Plant J. (1994) 6: 271-282). The use of T-DNA to transform plant cells has received extensive study and is amply described (e.g. EP-A 120 516). For introduction into plants, the chimeric genes of the invention can be inserted into binary vectors as described in the examples.

Other transformation methods are available to those skilled in the art, such as direct uptake of foreign DNA constructs (see EP-A 295 959), techniques of electroporation (Fromm, M. E. et al., Nature (1986), 319: 791-793) or high velocity ballistic bombardment with metal particles coated with the nucleic acid constructs (e.g. U.S. Pat. No. 4,945,050). Once transformed, the cells can be regenerated by those skilled in the art. Of particular relevance are the methods to transform foreign genes into commercially important crops, such as rapeseed (De Block, M. et al., Plant Physiol. (1989) 91: 694-701), sunflower (Everett, N. P. et al., Bio/Technology (1987) 5: 1201-1204), soybean (EP-A 301 749), rice (Hiei, Y. et al., The Plant J. (1994) 6: 271-282), and corn (Fromm et al., 1990, Bio/Technology 8: 833-839).

Those skilled in the art will appreciate that the choice of method might depend on the type of plant, i.e., monocotyledonous or dicotyledonous.

In another embodiment, the vector as described herein may be directly transformed into the plastid genome. Plastid transformation technology is extensively described in, e.g., U.S.

Pat. Nos. 5,451,513; 5,545,817; 5,545,818 and WO 95/16783. The basic technique for chloroplast transformation involves introducing regions of cloned plastid DNA flanking a selectable marker together with the gene of interest into a suitable target tissue, e.g., using biolistics or protoplast transformation (e.g. calcium chloride or PEG mediated transformation).

Agrobacterium tumefaciens cells containing a vector according to the present invention, wherein the vector comprises a Ti plasmid, are useful in methods of making transformed plants. Plant cells are infected with an *Agrobacterium tumefaciens* as described above to produce a transformed plant cell, and then a plant is regenerated from the transformed plant cell. Numerous *Agrobacterium* vector systems useful in carrying out the present invention are known. These typically carry at least one T-DNA border sequence and include vectors such as pBIN19 (Bevan, Nucl. Acids Res. (1984) 12: 8711-8720).

Methods using either a form of direct gene transfer or *Agrobacterium*-mediated transfer usually, but not necessarily, are undertaken with a selectable marker which may provide resistance to an antibiotic (e.g. kanamycin, hygromycin or methotrexate) or a herbicide (e.g. phosphinothricin). The choice of selectable marker for plant transformation is not, however, critical to the invention.

General methods of culturing plant tissues are provided for example by Maki, K. Y. et al., Plant Physiol. (1993) 15: 473-497; and by Phillips, R. I. et al. In: Sprague G F, Dudley J W, eds. *Corn and corn improvement.* 3rd edn. Madison (1988) 345-387.

After transformation the transgenic plant cells are placed in an appropriate selective medium for selection of transgenic cells which are then grown to callus. Shoots are grown from callus and plantlets generated from the shoot by growing in rooting medium. The particular marker used will allow for selection of transformed cells as compared to cells lacking the DNA which has been introduced.

To confirm the presence of the transgenes in transgenic cells and plants, a variety of assays may be performed. Such assays include, for example, "molecular biological" assays well known to those of skill in the art, such as Southern and Northern blotting, in situ hybridization and nucleic acid-based amplification methods such as PCR or RT-PCR and "biochemical" assays, such as detecting the presence of a protein product, e.g., by immunological means (ELISAs and Western blots) or by enzymatic function. The presence of enzymatically active valencene synthase may be established by chemical analysis of the volatile products (valencene) of the plant.

A valencene synthase according to the invention may be used for the industrial production of valencene, which valencene may be used per se as a flavour or aroma, e.g. in a food product, or as a fragrance, e.g. in a household product, or as an intermediate for the production of another isoprenoid, e.g. nootkatone.

A method for producing valencene according to the invention comprises preparing valencene in the presence of valencene synthase. In principle such a method can be based on any technique for employing an enzyme in the preparation of a compound of interest.

The method can be a method wherein FPP or any of its precursors (such as farnesol, IPP, isopentenyl phosphate, 3-methylbut-3-en-1-ol and even mevalonate) is fed as a substrate to cells comprising the valencene synthase. Alternatively the method can also be a method wherein use is made of a living organism that comprises an enzyme system capable of forming FPP from a suitable carbon source, thus establishing a full fermentative route to valencene. It should be noted that the term "fermentative" is used herein in a broad sense for processes wherein use is made of a culture of an organism to synthesise a compound from a suitable feedstock (e.g. a carbohydrate, an amino acid source, a fatty acid source). Thus, fermentative processes as meant herein are not limited to anaerobic conditions, and extended to processes under aerobic conditions. Suitable feedstocks are generally known for specific species of (micro-)organisms.

Also, use may be made of the valencene synthase isolated from the cell wherein it has been produced, e.g. in a reaction system wherein the substrate (FPP) and the valencene synthase are contacted under suitable conditions (pH, solvent, temperature), which conditions may be based on the prior art referred to herein and the present disclosure, optionally in combination with some routine testing. The valencene synthase may e.g. be solubilised in an aqueous medium wherein also the FPP is present or the valencene synthase may be immobilised on a support material in a manner known in the art and then contacted with a liquid comprising the FPP. Since the enzyme has a high activity and/or selectivity towards the catalysis from FPP to valencene, the present invention is also advantageous for such an in vitro method, not only under acidic conditions, but also in case the pH is about neutral or alkaline. Suitable conditions may be based on known methodology for known valencene synthases, e.g. referred to in the literature referred to herein, the information disclosed herein, common general knowledge and optionally some routine experimentation.

In a particularly advantageous method of the invention, valencene is fermentatively prepared, i.e. by cultivating cells expressing valencene synthase in a culture medium. The actual reaction catalysed by the valencene synthase may take place intracellularly or—if the valencene synthase is excreted into the culture medium—extracellularly in the culture medium.

The cells used for in a method for preparing valencene according to the invention may in particular be host cells according to the invention. If desired, these host cells may be engineered to supply the FPP to the valencene synthase in increased amounts. This can for instance be done by enhancing the flux of carbon towards FPP, which in itself can be realized in different ways. In host cells with an endogenous DXP pathway (like *E. coli* and *R. sphaeroides*) deregulation of the expression of these pathway's enzymes can have a clear positive effect on isoprenoids formation. Overexpression of dxs encoding 1-deoxy-D-xylulose-5-phosphate synthase (DXP-synthases), the first enzyme of the DXP pathway and thus one of the main targets for metabolic engineering, has resulted in increased biosynthesis of several isoprenoids (e.g., Matthews and Wurtzel, Appl. Microbiol. Biotechnol. (2000) 53: 396-400; Huang et al., Bioorg. Med. Chem. (2001) 9: 2237-2242; Harker and Bramley, FEBS Lett (1999) 448: 115-119; Jones et al. Metab. Eng. (2000) 2: 328-338; and Yuan et al. Metab. Eng. (2006) 8: 79-90). Also overexpression of dxr coding for DXP isomeroreductase (also known as, 1-deoxy-D-xylulose-5-phosphate reductoisomerase), the enzyme catalyzing the second and committed step in the DXP pathway, can lead to increased isoprenoid production (Albrecht et al., Biotechnol. Lett. (1999) 21: 791-795), which effect can be further increased by co-overexpressing dxs at the same time (Kim & Keasling, Biotechnol Bioeng (2001) 72: 408-415). A positive effect on isoprenoid biosynthesis was further obtained by overexpression of isopentenyl diphosphate isomerase (IPP isomerase, Idi), the enzyme that catalyzes the interconversion of IPP to dimethylallyl diphosphate, DMAPP (e.g., Kajiwara et al. Biochem. J. (1997) 324: 421-426);

Misawa and Shimada, J. Biotech. (1998) 59: 169-181; and Yuan et al. Metab. Eng. (2006) 8: 79-90) and the enzymes MEP cytidylyltransferase (also known as 4-diphosphocytidyl-2-C-methyl-D-erythritol synthase, IspD) and 2C-methyl-D-erythritol 2,4-cyclodiphosphate synthase (IspF), that are transcribed as one operon ispDF in *E. coli* (Yuan et al. Metab. Eng. (2006) 8: 79-90).

An alternative and more efficient approach to engineer strains with an endogenous DXP pathway for high-level production of isoprenoids is the introduction of a heterologous mevalonate pathway. Coexpression in *E. coli* of the *Saccharomyces cerevisiae* mevalonate pathway with a synthetic amorpha-4,11-diene synthase gene resulted in the formation of the sesquiterpene amorphadiene in titres of more than 110 mg/L when the recombinant *E. coli* strain was cultivated in an LB+ glycerol medium (Martin et al. Nat. Biotechnol. (2003) 21: 796-802). This *E. coli* strain was subsequently improved by the introduction of extra copies of the gene tHMG1 encoding the C-terminal catalytic domain of the yeast enzyme 3-hydroxy-3-methyl-glutaryl-coenzyme A (HMG-CoA) reductase. By increasing the formation and thus the activity of this enzyme, the intracellular level of the toxic mevalonate pathway intermediate HMG-CoA was reduced thereby overcoming growth inhibition and leading to an increased production of mevalonate (Pitera et al. Metab. Eng. (2007) 9: 193-207). Further improvement of the flux through the heterologous mevalonate pathway was obtained by codon optimization of the first three genes of this pathway in combination with replacement of the wild-type lac promoter with the two-fold stronger lac UV5 promoter (Anthony et al. Met. Eng. (2009) 11: 13-19). The production of amorphadiene could be even more increased by replacing the yeast genes for HMG-CoA synthase and HMG-CoA reductase with the equivalent genes from the gram positive bacterium *Staphylococcus aureus*. In combination with an optimized fermentation protocol, cultivation of this novel engineered *E. coli* strain yielded an amorphadiene titre of 27.4 g/L (Tsuruta et al. PloS ONE (2009) 4(2): e4489. doi:10.1371/journal.pone.0004489). Similarly, an *E. coli* strain engineered with the mevalonate pathway from *Streptococcus pneumoniae* in combination with the *Agrobacterium tumefaciens* decaprenyl diphosphate synthase (ddsA) gene produced coenzyme $Q_{10}$ ($CoQ_{10}$) in more than 2400 µg/g cell dry weight (Zahiri et al. Met. Eng. (2006) 8: 406-416. Increased production of $CoQ_{10}$ was also obtained by engineering a *Rhodobacter sphaeroides* strain with the mevalonate pathway from *Paracoccus zeaxanthinifaciens* in its native (WO 2005/005650) and a mutated from (WO 2006/018211).

Also host cells with an endogenous MEV pathway (like *S. cerevisiae*) have been the subject of multiple engineering studies to obtain isoprenoid hyper producing strains. Introduction into *S. cerevisiae* of the heterologous *E. coli* derived DXP pathway in combination with the gene encoding the Citrus valencene synthase resulted in a strain accumulating approximately 10-fold more valencene compared to the strain expressing only the valencene synthase (WO 2007/093962). Most improvements in the industrially-important yeasts *Candida utilis* and *S. cerevisiae*, however, have centred on the engineering of the homologous MEV pathway. Especially overexpression of the enzyme HMG-CoA reductase, which is believed to be the main regulatory enzyme in the DXP pathway, in its full-length or truncated version, has appeared to be an efficient method to increase production of isoprenoids. This stimulating effect of overexpression of the N-terminal truncated HMG-CoA reductase has, for instance, been observed in case of lycopene production in *C. utilis* (Shimada et al. Appl. Env. Microbiol. (1998) 64: 2676-2680) and epi-cedrol production in *S. cerevisiae* (Jackson et al. Org. Lett. (2003) 5: 1629-1632). In the last case the production of this sesquiterpene could be further enhanced by introduction of upc2-1, an allele that elicitates an increase in the metabolic flux to sterol biosynthesis. Another method to increase the flux through the MEV pathway is the employment of a mevalonate kinase variant that is less sensitive for feedback inhibition by FPP and other isoprenoid precursors. WO 2006/063752, for instance, shows that *Paracoccus zeaxanthinifaciens* R114, a bacterium with an endogenous MEV pathway, after introduction of the *S. cerevisiae* mevalonate kinase mutant N66K/I152M and the ddsA gene from *P. zeaxanthinifaciens* ATCC 21588 produces significantly more coenzyme $Q_{10}$ than the corresponding *P. zeaxanthinifaciens* strain expressing the wild type *S. cerevisiae* mevalonate kinase. Similar positive results on $CoQ_{10}$ production with *P. zeaxanthinifaciens* R114 have also been obtained with the feedback resistant variant K93E of the *P. zeaxanthinifaciens* mevalonate kinase (WO 2004/111214).

A second approach to increased amounts of FPP is based on reducing or elimination of enzymatic side activities on FPP. In yeast the gene ERG9 encodes the enzyme farnesyl diphosphate farnesyl transferase (squalene synthase), which catalyzes the condensation of two farnesyl diphosphate moieties to form squalene. Because this is the first step after FPP in the sterol biosynthesis and thus regulates the flux of isoprene units into the sterol pathway, ERG9 is a frequent target in yeast metabolic engineering for increased sesquiterpene and carotenoids production. Disruption of ERG9 in combination with overexpression of the tHMG-CoA reductase in the yeast *C. utilis* led to increased production of lycopene (Shimada et al. Appl. Env. Microbiol. (1998) 64: 2676-2680). A similar combination of overexpression of tHMG-CoA reductase and downregulation of ERG9 using a methionine repressible promoter increased the production of the sesquiterpene amorphadiene in yeast with approx. 10-fold as compared to the yeast strain only expressing the amorphadiene synthase gene (Ro et al. Nature (2006) 440: 940-943; Lenihan et al. Biotechnol. Prog. (2008) 24: 1026-1032). Since ergosterol is vital for yeast growth and yeast cells cannot assimilate externally fed ergosterol during aerobic growth, downregulation/knockout of ERG9 is frequently combined with mutations that equip the yeast strain with efficient aerobic uptake of ergosterol from the culture medium. Examples are the sue allele (Takahishi et al. Biotechnol. Bioeng. (2007) 97: 170-181) and the upc2-1 allele (Jackson et al. Org. Lett. (2003) 5: 1629-1632). Takahashi et al (Biotechnol. Bioeng. (2007) 97: 170-181) also investigated the effect of limiting the endogenous phosphatase activity by knocking out the phosphatase gene dpp1 in yeast. Although this knockout clearly limited the dephosphorylation of FPP reflected by much less farnesol accumulation, it did not improve sesquiterpene production beyond that of the combined erg9/sue mutations under the growth conditions applied.

Reaction conditions for fermentatively preparing valencene may be chosen depending upon known conditions for the species of host cell used (e.g. *Rhodobacter capsulatus, Rhodobacter sphaeroides, Paracoccus* zeaxanthinifaciens, *Escherichia coli, Aspergillus nidulans, Aspergillus niger, Aspergillus oryzae, Saccharomyces cerevisiae, Penicillium chrysogenum, Phaffia rhodozyma* and *Pichia pastoris*), the information disclosed herein, common general knowledge and optionally some routine experimentation.

In principle, the pH of the reaction medium (culture medium) used in a method according to the invention may be chosen within wide limits, as long as the valencene synthase (in the host cell) is active and displays a wanted specificity under the pH conditions. In case the method includes the use of cells, for expressing the valencene synthase, the pH is selected such that the cells are capable of performing its intended function or functions. The pH may in particular be chosen within the range of four pH units below neutral pH and two pH units above neutral pH, i.e. between pH 3 and pH 9 in case of an essentially aqueous system at 25° C. Good results have e.g. been achieved in an aqueous reaction medium having a pH in the range of 6.8 to 7.5.

A system is considered aqueous if water is the only solvent or the predominant solvent (>50 wt. %, in particular >90 wt. %, based on total liquids), wherein e.g. a minor amount of alcohol or another solvent (<50 wt. %, in particular <10 wt. %, based on total liquids) may be dissolved (e.g. as a carbon source, in case of a full fermentative approach) in such a concentration that micro-organisms which are present remain active.

In particular in case a yeast and/or a fungus is used, acidic conditions may be preferred, in particular the pH may be in the range of pH 3 to pH 8, based on an essentially aqueous system at 25° C. If desired, the pH may be adjusted using an acid and/or a base or buffered with a suitable combination of an acid and a base.

Anaerobic conditions are herein defined as conditions without any oxygen or in which substantially no oxygen is consumed by the cultured cells, in particular a micro-organism, and usually corresponds to an oxygen consumption of less than 5 mmol/l·h, preferably to an oxygen consumption of less than 2.5 mmol/l·h, or more preferably less than 1 mmol/l·h. Aerobic conditions are conditions in which a sufficient level of oxygen for unrestricted growth is dissolved in the medium, able to support a rate of oxygen consumption of at least 10 mmol/l·h, more preferably more than 20 mmol/l·h, even more preferably more than 50 mmol/l·h, and most preferably more than 100 mmol/l·h.

Oxygen-limited conditions are defined as conditions in which the oxygen consumption is limited by the oxygen transfer from the gas to the liquid. The lower limit for oxygen-limited conditions is determined by the upper limit for anaerobic conditions, i.e. usually at least 1 mmol/l·h, and in particular at least 2.5 mmol/l·h, or at least 5 mmol/l·h. The upper limit for oxygen-limited conditions is determined by the lower limit for aerobic conditions, i.e. less than 100 mmol/l·h, less than 50 mmol/l·h, less than 20 mmol/l·h, or less than to 10 mmol/l·h.

Whether conditions are aerobic, anaerobic or oxygen-limited is dependent on the conditions under which the method is carried out, in particular by the amount and composition of ingoing gas flow, the actual mixing/mass transfer properties of the equipment used, the type of micro-organism used and the micro-organism density.

In principle, the temperature used is not critical, as long as the valencene synthase (in the cells), shows substantial activity. Generally, the temperature may be at least 0° C., in particular at least 15° C., more in particular at least 20° C. A desired maximum temperature depends upon the valencene synthase and the cells, in case of a method wherein use is made of cells for expressing the valencene synthase. The temperature is 70° or less, preferably 50° C. or less, more preferably 40° C. or less, in particular 35° C. or less.

In case of a fermentative process, the incubation conditions can be chosen within wide limits as long as the cells show sufficient activity and/or growth. This includes aerobic, oxygen-limited and anaerobic conditions.

In particular if the catalytic reaction whereby valencene is formed, is carried out outside a host cell, a reaction medium comprising an organic solvent may be used in a high concentration (e.g. more than 50%, or more than 90 wt. %, based on total liquids), in case the valencene synthase that is used retains sufficient activity and specificity in such a medium.

If desired, valencene produced in a method according to the invention, or a further compound into which valencene has been converted after its preparation (such as nootkatone), is recovered from the reaction medium, wherein it has been made. A suitable method is liquid-liquid extraction with an extracting liquid that is non-miscible with the reaction medium.

In particular suitable (for extraction from an aqueous reaction medium) is extraction with a liquid organic solvent, such as a liquid hydrocarbon. From initial results it is apparent that this method is also suitable to extract the valencene (or further product) from a reaction medium comprising cells according to the invention used for its production, without needing to lyse the cells for recovery of the valencene (or further product). In particular, the organic solvent may be selected from liquid alkanes, liquid long-chain alcohols (alcohols having at least 12 carbon atoms), and liquid esters of long-chain fatty acids (acids having at least 12 carbon atoms). Suitable liquid alkanes in particular include C6-C16 alkanes, such as hexane, octane, decane, dodecane, isododecane and hexadecane. Suitable long-chain aliphatic alcohol in particular include C12-C18 aliphatic alcohols, like oleyl alcohol and palmitoleyl alcohol. Suitable esters of long-chain fatty acids in particular include esters of C1-C4 alcohols of C12-C18 fatty acids, like isopropyl myristate, and ethyl oleate.

In an advantageous embodiment, valencene (or a further product) is produced in a reactor comprising a first liquid phase (the reaction phase), said first liquid phase containing cells according to the invention in which cells the valencene (or a further product) is produced, and a second liquid phase (organic phase that remains essentially phase-separated with the first phase when contacted), said second liquid phase being the extracting phase, for which the formed product has a higher affinity. This method is advantageous in that it allows in situ product recovery. Also, it contributes to preventing or at least reducing potential toxic effects of valencene (or a further product) to the cells, because due to the presence of the second phase, the valencene (or a further product) concentration in the reaction phase may be kept relatively low throughout the process. Finally, there are strong indications that the extracting phase contributes to extracting the valencene (or further product) out of the reaction phase.

In a preferred method of the invention the extracting phase forms a layer on top of the reaction phase or is mixed with the reaction phase to form a dispersion of the reaction phase in the extracting phase or a dispersion of the extracting phase in the reaction phase. Thus, the extracting phase not only extracts product from the reaction phase, but also helps to reduce or completely avoid losses of the formed product from the reactor through the off-gas, that may occur if valencene is produced in the (aqueous) reaction phase or excreted into the (aqueous) reaction phase. Valencene is poorly soluble in water and therefore easily volatilizes from water. It is contemplated that valencene solvated in the organic phase (as a layer or dispersion) is at least substantially prevented from volatilization.

Suitable liquids for use as extracting phase combine a lower density than the reaction phase with a good biocompatibility (no interference with the viability of living cells), low volatility, and near absolute immiscibility with the aqueous reaction phase. Examples of suitable liquids for this application are liquid alkanes like decane, dodecane, isododecane, tetradecane, and hexadecane or long-chain aliphatic alcohols like oleyl alcohol, and palmitoleyl alcohol, or esters of long-chain fatty acids like isopropyl myristate, and ethyl oleate (see e.g. Asadollahi et al. (Biotechnol. Bioeng. (2008) 99: 666-677), Newman et al. (Biotechnol. Bioeng. (2006) 95: 684-691) and WO 2009/042070).

The valencene produced in accordance with the invention may be used as such, e.g. for use as a flavour or fragrance, or as an insect repellent, or may be used as a starting material for another compound, in particular another flavour or fragrance. In particular, valencene may be converted into nootkatone. The conversion of valencene into nootkatone may be carried out intracellularly, or extracellularly. If this preparation is carried out inside a cell, the nootkatone is usually isolated from the host cell after its production.

Suitable manners of converting valencene to nootkatone are known in the art, e.g. as described in Fraatz et al. Appl. Microbiol. Biotechnol (2009) 83: 35-41, of which the contents are incorporated by reference, or the references cited therein.

In general, suitable methods to prepare nootkatone from valence may be divided in: i. purely chemical methods, ii. biocatalytic methods (e.g. those using laccases in combination with a mediator), iii. bioconversion (i.e. methods applying whole living cells), and iv. full fermentation. In methods i-iii externally fed valencene is converted, whereas in method iv the valencene is produced in situ.

In a specific embodiment, the conversion comprises a regiospecific hydroxylation of valencene at the 2-position to alpha- and/or beta-nootkatol, followed by oxidation thereof forming nootkatone.

In a further embodiment, valencene is converted into the hydroperoxide of valencene, which is thereafter converted in nootkatone. U.S. Pat. No. 5,847,226 describes the chemical conversion of (+)-valencene into nootkatone in an oxygen-containing atmosphere in the presence of a hydroperoxyde of an unsaturated fatty acid. This fatty acid hydroperoxide is generated in situ by, e.g., autooxidation, photooxidation or enzymatic oxidation using a lipoxyygenase, after which this hydroperoxide catalyzes the autooxidation of valencene.

(+)-Valencene can be converted in high yields into nootkatone by different species of the green alga *Chlorella* or the fungus *Botryosphaeria* (Furusawa et al. Chem. Pharm. Bull. (2005) 53: 1513-1514, and JP 2003-070492).

EP-A 1 083 233 describes the preparation of nootkatone applying cell-free (biocatalytic) systems based on laccase catalyzed conversion of valencene into valencene hydroperoxide, which is subsequently degraded to form nootkatone. Optionally, a mediator and/or a solvent at a concentration that maintains laccase activity may be included.

WO 2006/079020 describes amongst other things a novel plant derived cytochrome P450 enzyme, the Premnaspirodiene oxygenase (HPO) from *Hyoscyamus muticus* which catalyzes the mono-hydroxylation of (+)-valencene to mainly beta-nootkatol. Nootkatone formation was only observed at very high concentrations of nootkatol (>30 µM) but only at a very low reaction rate (Takahashi et al. J. Biol. Chem. (2007) 282: 31744-31754). In the same paper, Takahashi et al. report on an HPO mutant with a 5-fold improvement in its catalytic efficiency for nootkatol biosynthesis without significantly changing the overall reaction product profiles. This nootkatol might be further oxidized to nootkatone by co-expression of an alcohol dehydrogenase enzyme in the same host cell.

Besides plant derived cytochrome P450 enzymes, also the bacterial cytochrome 450 monooxygenases P450cam and P450BM-3 and mutants thereof have been reported to oxidize (+)-valencene (Sowden et al. Org. Biomol. Chem. (2005) 3: 57-64). Whereas wild type P450cam did not catalyze this oxidation reaction, mutants showed relatively high regioselectivity for the desired C2 position in (+)-valencene, (+)-trans-nootkatol and (+)-nootkatone constituting >85% of the products formed. The activity of these mutants was still rather low. The P450BM-3 mutants, on the other hand, displayed a higher activity but were unselective because of the multiple binding orientations of (+)-valencene in the active site. Recently, much more selective BM-3 mutants have been reported, the best of which has a C2-regioselectivity of 95% (Seifert et al. ChemBioChem (2009) 10: 853-861).

It is contemplated that one or more genes encoding an enzyme or plurality of enzymes for catalysing the conversion of valencene into nootkatone may be incorporated in a host cell according to the invention. Such enzymes may in for instance be selected from the enzymes of *Chlorella* or *Botryosphaeria*, or Premnaspirodiene oxidase from *Hyoscyamus muticus*, or the P450cam or P450BM-3 mutants referred to herein above.

As indicated above, the invention relates to an antibody having binding affinity to a valencene synthase according to the invention. The term "antibody" includes reference to antigen binding forms of antibodies (e.g., Fab, F (ab) 2). The term "antibody" frequently refers to a polypeptide substantially encoded by an immunoglobulin gene or immunoglobulin genes, or fragments thereof which specifically bind and recognize an analyte (antigen). However, while various antibody fragments can be defined in terms of the digestion of an intact antibody, one of skill will appreciate that such fragments may be synthesized de novo either chemically or by utilizing recombinant DNA methodology. Thus, the term antibody, as used herein, also includes antibody fragments such as single chain Fv, chimeric antibodies (i.e., comprising constant and variable regions from different species), humanized antibodies (i.e., comprising a complementarity determining region (CDR) from a non-human source) and heteroconjugate antibodies (e.g., bispecific antibodies).

The antibodies or fragments thereof can be produced by any method known in the art for the synthesis of antibodies, in particular, by chemical synthesis or preferably, by recombinant expression techniques.

Polyclonal antibodies to valencene synthase can be produced by various procedures well known in the art. For example, a heterologous valencene synthase can be administered to various host animals including, but not limited to, rabbits, mice, rats, etc. to induce the production of sera containing polyclonal antibodies specific for valencene synthase. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual*, (Cold Spring Harbor Laboratory Press, 2nd ed. 1988); Hammerling, et al., in: *Monoclonal Antibodies and T-Cell Hybridomas* 563-681 (Elsevier, N.Y., 1981). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. Briefly, mice can be immunized with valencene synthase and once an immune response is detected, e.g., antibodies specific for the valencene synthase are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

In certain embodiments, a method of generating monoclonal antibodies comprises culturing a hybridoma cell secreting an antibody of the invention wherein, preferably, the hybridoma is generated by fusing splenocytes isolated from a mouse immunized with valencene synthase with myeloma cells and then screening the hybridomas resulting from the fusion for hybridoma clones that secrete an antibody able to bind valencene synthase. An antibody according to the invention may for instance be used in a method for isolating a valencene synthase produced in accordance with the invention, e.g. by using the antibody immobilised on a chromatographic support material.

Further, the present disclosure is directed to a method for preparing a terpenoid or a terpene, the method comprising converting a polyprenyl diphosphate substrate into the terpenoid or terpene in the presence of an enzyme, the enzyme comprising a first segment comprising a tag-peptide and a second segment comprising a polypeptide having enzymatic activity for converting a polyprenyl diphosphate into that terpene or terpenoid. An enzyme comprising said first and said second segment may herein be referred to as a 'tagged enzyme'.

In particular, the terpene that is prepared may be valencene, in which case the tagged enzyme has valencene synthase activity, or amorphadiene, in which case the tagged enzyme has amorphadiene synthase activity. For valencene preparation in particular use can be made of a method, an amino acid sequence, a nucleic acid sequence or a host cell as described herein.

Further, the terpene or terpenoid may amongst others be selected from the group of nootkatone and artemisinic acid. Artemisinic acid can be prepared by oxygenation/oxidation of amorphadiene in a manner known per se.

The tag-peptide is preferably selected from the group of nitrogen utilization proteins (NusA), thioredoxins (Trx), maltose-binding proteins (MBP), a peptide having the sequence: EEASVTSTEETLTPAQEAARTRAAN-KARKEAELAAATAEQ (the so called SET-tag, SEQ ID NO: 34), and functional homologues thereof. As used herein a functional homologue of a tag peptide is a tag peptide having at least about the same effect on the solubility of the tagged enzyme, compared to the non-tagged enzyme. Typically the homologue differs in that one or more amino acids have been inserted, substituted, deleted from or extended to the peptide of which it is a homologue. The homologue may in particular comprise one or more substitutions of a hydrophilic amino acid for another hydrophilic amino acid or of a hydrophobic amino acid for another. The homologue may in particular have a sequence identity of at least 40%, more in particular of at least 50%, preferably of at least 55%, more preferably of at least 60%, at least 70%, at least 75%, at least 80%, at least 85%, at least 90%, at least 95%, at least 98% or at least 99% with the sequence of a NusA, Trx, MBP or SET.

SEQ ID NO 25 and 24 show a valencene synthase provided with a SET-tag respectively a nucleic acid sequence encoding said valencene synthase.

Particularly suitable is maltose binding protein from *Escherichia coli*, or a functional homologue thereof.

The use of a tagged enzyme according to the invention is in particular advantageous in that it may contribute to an increased production, especially increased cellular production of a terpenoid or a terpene, such as valencene or amorphadiene.

For improved solubility of the tagged enzyme (compared to the enzyme without the tag), the first segment of the enzyme is preferably bound at its C-terminus to the N-terminus of the second segment. Alternatively, the first segment of the tagged enzyme is bound at its N-terminus to the C-terminus of the second segment.

Further, the present disclosure is directed to a nucleic acid comprising a nucleotide sequence encoding a polypeptide, the polypeptide comprising a first segment comprising a tag-peptide, preferably an MBP, a NusA, a Trx, a SET-tag) or a functional homologue of any of these, and a second segment comprising a terpenoid synthase or terpene synthase, preferably a valencene synthase or an amorphadiene synthase. The second segment may for instance comprise an amino acid sequence as shown in SEQ ID NO: 2, SEQ ID NO: 4, SEQ ID NO: 9, SEQ ID NO: 27 or a functional homologue of any of these sequences with SEQ ID NO: 2, SEQ ID NO: 4, SEQ ID NO: 9 or SEQ ID NO: 27.

Further, the present disclosure is directed to a host cell comprising said nucleic acid encoding said tagged terpenoid synthase or tagged terpene synthase. Specific nucleic acids according to the invention encoding a tagged enzyme are shown in SEQ ID NO: 10, SEQ ID NO: 12, SEQ ID NO: 14, SEQ ID NO: 16, SEQ ID NO: 20, SEQ ID NO: 22, SEQ ID NO: 24 and SEQ ID NO: 28. The host cell may in particular comprise a gene comprising any of these sequences or a functional analogue thereof.

SEQ ID NO: 28 shows a nucleotide sequence encoding an amorphadiene synthase with an N-terminal MBP-tag (MBP-AaaS).

Further, the present disclosure is directed to an enzyme, comprising a first segment comprising a tag-peptide and a second segment comprising a polypeptide having enzymatic activity for converting a polyprenyl diphosphate into a terpene, in particular a valencene synthase or an amorphadiene synthase, the tag-peptide preferably being selected from the group of MBP, NusA, Trx or SET). Specific enzymes comprising a tagged enzyme according to the invention are shown in SEQ ID NO: 11, SEQ ID NO: 13, SEQ ID NO: 15, SEQ ID NO: 17, SEQ ID NO 21, SEQ ID NO: 23, SEQ ID NO: 25 and SEQ ID NO: 29 (MBP-AaaS).

The invention will now be illustrated by the following examples.

EXAMPLES

General Part

Valencene Synthase Activity Test

For verifying whether a polypeptide has valencene synthase activity the following test can be used.

In a glass tube, make a mix of 800 µL of MOPSO buffer (15 mM MOPSO (3-[N-morpholino]-2-hydroxypropane sulphonic acid) pH=7.0, 1 mM $MgCl_2$, 0.1% Tween 20, 1 mM ascorbic acid, 1 mM dithiothreitol), 175 µL of purified polypeptide solution (as a rule of thumb providing about 100 ng of the polypeptide) and 5 μL of farnesyl diphosphate (10 mM, Sigma FPP dry-evaporated and dissolved in 0.2 M ammonium carbamate and 50% ethanol). Carefully overlay the mix with 500₄ of pentane, and incubate at 30° C. with mild agitation for 2 hours. Subsequently, collect the pentane. Then, subject the remaining water-phase to extraction with 1 mL ethylacetate. Combine the ethylacetate and the pentane phases and centrifuge the combination at 1,200×g. Dry over a sodium sulphate column and analyse a sample of the dried product by GC-MS. Suitably for the GC-MS analysis an Agilent Technologies system, comprising a 7980A GC system, a 597C inert MSD detector (70 eV), a 7683 auto-sampler and injector and a Phenomenex Zebron ZB-5 ms column of 30 m length×0.25 mm internal diameter and 0.25 μM stationary phase, with a Guardian precolumn (5 m) may be used. In this system, inject 1 μL of the sample, under the following conditions: injection port at 250° C., splitless injection, the ZB5 column maintained at 45° C. for 2 minutes after which a gradient of 10° C. per minute is started, until 300° C. Sesquiterpene peaks are detected at 204 m/z. Compounds can be identified by their retention index and by their mass spectrum in combination with comparison of the mass spectrum to libraries (NIST or in-house developed). In this system, valencene is detected at (about) 14.125 minutes. If valencene is detected, the polypeptide is a valencene synthase.

Bacteria and Culture Conditions

*Rhodobacter sphaeroides* strain Rs265-9c was obtained from *Rhodobacter sphaeroides* strain ATCC 35053 [purchased from the American Type Culture Collection (ATCC-Manassas, VA, USA-worldwideweb atcc.org); number 35053; *Rhodobacter sphaeroides*(van Niel) Imhoff et al., isolated from a sewage settling pond in Indiana and deposited as *Rhodopseudomonas sphaeroides* van Niel] after two rounds of mutagenesis and was used as the base host for construction of recombinant strains having improved production of valencene. All *R. sphaeroides* strains were grown at 30° C. in medium RS102 unless otherwise stated. The composition and preparation of medium RS102 is summarized in Table 1.

*E. coli* strains were grown at 37° C. in LB medium (Becton Dickinson, Sparks, Md., USA). For maintenance of plasmids in recombinant *E. coli* and *R. sphaeroides* strains, ampicillin (100 mg/L), chloramphenicol (30 mg/L) and/or kanamycin (25-50 mg/L, depending on the plasmid) were added to the culture medium. Liquid cultures were routinely grown aerobically in a rotary shaker at 220 rpm (see below). When solid media were required, agar (1.5% final concentration) was added.

TABLE 1

Composition and preparation of medium RS102

| Component | Amount per litre distilled water |
|---|---|
| 1. Yeast extract | 20 g |
| 2. NaCl | 0.5 g |
| 3. MgSO₄•7H₂O | 0.5 g |
| 4. D-glucose monohydrate | 33 g |
| 5. Microelements solution | 2 mL |
| 6. CaFe solution | 2 mL |

Components 1-4 are mixed together, the final volume is adjusted to 1 litre. The pH is adjusted to 7.4 with 0.5M NaOH. The resulting base medium is then sterilized by filtration through a 0.22 micron membrane; 2 mL each of sterile microelements solution and sterile CaFe solution (see below) are added to give the final medium RS102. For solid medium, the 1 litre base medium mentioned above plus 15 g agar are first mixed together and autoclaved. After the medium is cooled to about 60° C., the sterile microelements and CaFe solutions (2 mL of each) are added and the molten medium is dispensed into sterile Petri plates.

TABLE 1-continued

Composition and preparation of medium RS102

| Component | Amount perlitre distilled water |
|---|---|
| Microelements solution | |
| (NH₄)₂Fe(SO₄)₂•6H₂O | 80 g |
| ZnSO₄•7H₂O | 6 g |
| MnSO₄•H₂O | 2 g |
| NiSO₄•6H₂O | 0.2 g |
| Vitamin C | 2 g |

Sterilize by filtration through a 0.22 micron membrane, store at 4° C.

| CaFe solution | |
|---|---|
| CaCl₂•2H₂O | 75 g |
| FeCl₃•6H₂O | 5 g |
| HCl (37%) | 3.75 ml |

Sterilize by filtration through a 0.22 micron membrane, store at 4° C.

Example 1

Construction of *E. coli* Expression Vectors

*Chamaecyparis nootkatensis* pendula was purchased from "Plantentuin Esveld" in Boskoop (NL). RNA was extracted from woody tissue from branches. 15 mL extraction buffer (2% hexadecyltrimethylammonium bromide, 2% polyvinylpyrrolidinone K 30, 100 mM Tris-HCl (pH 8.0), 25 mM EDTA, 2.0 M NaCl, 0.5 g/L spermidine and 2% β-mercaptoethanol (added just before use)) was warmed to 65° C. in a water bath, after which 2 g ground tissue was added and mixed completely by inverting the tube. The mixture was extracted two times with an equal volume of chloroform: isoamyl alcohol (24:1). ¼ volume of 10 M LiCl was added to the aqueous upper layer and mixed. The RNA was precipitated overnight at 4° C. and harvested by centrifugation at 10,000×g for 20 min. The pellet was dissolved in 500 μL of SSTE (1.0 M NaCl, 0.5% SDS, 10 mM Tris-HCl (pH 8.0), 1 mM EDTA (pH 8.0)), and extracted once with an equal volume of chloroform:isoamyl alcohol. Two volumes of ethanol were added to the aqueous upper layer, incubated for at least 2 hours at −20° C., centrifuged at 13,000×g, after which the supernatant was removed. The pellet was air dried, and resuspended in water. This procedure resulted in the isolation of approx. 60 μg of total RNA per 2 g of ground tissue.

Starting from 133 μg of total RNA from *Chamaecyparis nootkatensis* wood, 2.7 μg of PolyA+ RNA was isolated using the mRNA Purification Kit (GE Healthcare Life Sciences, Diegem, Belgium) according to the manufacturer's instructions. This polyA+ RNA was used to generate 3'RACE cDNA, using the SMART RACE cDNA Amplification Kit (Clontech, Mountain View, Calif., USA), according to the Kit's descriptions.

The full length open reading frame encoding the valencene synthase from *Chamaecyparis nootkatensis* according to the invention (herein below also referred to as "valC") was then amplified from the *C. nootkatensis* cDNA library using Phusion "proofreading polymerase" (Finnzymes, Espoo, Finland) and the following primers:

[SEQ ID NO: 5]
5'-atataggatccGGCTGAAATGTTTAATGGAAATTCCAGC-3'
(BamHI recognition site underlined),
and -continued

[SEQ ID NO: 6]
5'-atatactgcagCTCTGGATCTATGGAATGATTGGTTCCAC-3'

(PstI restriction site underlined).

The amplified fragment and vector pACYCDuet-1 (Novagen, Merck4Biosciences, Nottingham, UK) were digested with the restriction enzymes BamHI and PstI, followed by purification of the required DNA fragments, their subsequent ligation and finally transformation into *E. coli* XL1-Blue (Stratagene, La Jolla, Calif., USA) using standard procedures. Recombinant bacteria were selected on LB plates containing 30 μg/mL chloramphenicol. After overnight growth of recombinant colonies in liquid culture (3 mL LB broth with 30 μg/mL chloramphenicol, 250 rpm, 37° C.), plasmid DNA was isolated using the Qiaprep Spin Miniprep kit (Qiagen, Hilden, Germany). Isolated plasmid material was tested by restriction analysis using the enzymes BamHI and PstI. Finally, the insert of a correct vector, which was named pAC-65-3, was checked by DETT sequencing with vector primers. This cloning strategy led to the expression of ValC with an N-terminal Hiss-tag.

For expression of the *Citrus×paradisi* valencene synthase (ValF, accession number CAG29905), the full length open reading frame was prepared by custom DNA synthesis by a third party company. To improve its heterologous expression in *Rhodobacter sphaeroides*, this synthetic gene sequence was optimized in terms of codon usage (SEQ ID NO: 7). Furthermore, the synthetic gene comprised an NdeI restriction site at its 5'-end, which also provided the ATG start codon, and a BamHI restriction site at its 3'-end downstream of a stop codon. After digestion of this synthetic gene and vector pET-16b (Novagen) with restriction enzymes NdeI and BamHI, the correct fragments were purified and ligated, followed by transformation of *E. coli* TOP 10 (Invitrogen, Breda, The Netherlands) using standard protocols. Recombinant bacteria were selected on LB plates containing 100 μg/mL ampicillin. After overnight growth of recombinant colonies in 5 mL LB broth with 100 μg/mL ampicillin, 250 rpm, 37° C., plasmid DNA was isolated using the Qiaprep Spin Miniprep kit (Qiagen). Finally, a correct recombinant plasmid was selected by testing for the presence of the desired insert fragment by restriction analysis using the enzymes NdeI and BamHI. This plasmid was named pET-16b-ValF.

Due to this cloning strategy, also the expressed ValF enzyme contains an N-terminal Hiss-tag.

Example 2

In Vitro Comparison of *C. nootkatensis* (Invention) Valencene Synthase and Citrus Valencene Synthase (Reference)

The control plasmid pACYCDuet-1, the pAC-65-3 construct (comprising a nucleic acid sequence encoding a valencene synthase according to the invention) and the pET-16b-ValF construct were transformed to *E. coli* BL21 AI (Invitrogen). For expression, a 1 mL overnight culture of the recombinant *E. coli* strains was prepared (LB medium with appropriate antibiotic; 30 ug chloramphenicol/mL in case of pAC-65-3 and pACYCDuet-1; 100 ug ampicillin/mL in case of pET-16b-ValF). 500 μL of that culture was transferred to 50 mL of LB medium with the appropriate antibiotic in a 250 mL Erlenmeyer flask, and incubated at 37° C., 250 rpm until the optical density at 600 nm ($OD_{600}$ or A600) was 0.4 to 0.6. Subsequently, 0.02% arabinose was added and cultures were incubated overnight at 18° C. and 250 rpm. The next day, cells were harvested by centrifugation (10 min 8,000×g), medium was removed, and cells were resuspended in 1 mL Resuspension buffer (50 mM Tris-HCl pH=8.0, 300 mM NaCl, 1.4 mM 2-mercaptoethanol; 4° C.). Cells were disrupted by sonication (on ice, 5 times 10 seconds with 10 seconds break, MSE Soniprep 150, amplitude 14 μm). Insoluble particles were subsequently removed by centrifugation (10 min 13,000×g, 4° C.) yielding the cell free extract.

Soluble protein was further purified by LMAC (immobilized metal affinity chromatography) on Ni-NTA spin columns (Qiagen). Cell free extract (600 μL) was loaded on these columns, which had been pre-rinsed with Resuspension buffer, and the columns were centrifuged at 700×g for 2 min, after which the flow-through was discarded. Subsequently the columns were washed two times with 600 μL Resuspension buffer (flow-through discarded) followed by transfer of the columns to a fresh tube. 100 μL of Imidazole Elution buffer (Resuspension buffer with 175 mM imidazole) was loaded onto the column, left for 2 minutes and collected by centrifugation. This elution procedure was repeated once. For every construct, in total 200 μL eluate was transferred to a Slide-A-Lyzer Mini Dialysis Unit (10,000 MWCO; Pierce, Rockford, Ill., USA), and dialyzed for 3 hours to 1 L Storage buffer (50 mM Tris-HCl pH=7.5, 12.5% glycerol, 1.4 mM 2-mercaptoethanol) at 4° C. After dialysis, the purified enzyme preparations were immediately used in enzyme assays, which were essentially executed as the Valencene synthase activity test described above. In this case, however, all peaks in the chromatograms were detected applying the total ion count mode. Compounds were identified by their retention index and by their mass spectrum in combination with comparison of the mass spectrum to libraries (NIST and in-house). To quantify the produced compounds, the peak surface area for each relevant peak was measured from the total ion count chromatograms.

The results of these in-vitro tests are given in Table 2.

TABLE 2

Terpenoid compounds detected in the in-vitro enzyme assays with valencene synthase purified from *E. coli* BL21 AI cells containing pAC-65-3 (thus expressing ValC), pET-16b-ValF (thus expressing ValF) or pACYCDuet-1 (negative blank).

|  | Rf (min) | pAC-65-3 (invention) area | pET-16b-ValF (reference) area | pACYCDuet-1 (blank) area |
|---|---|---|---|---|
| β-elemene/ germacrene A | 12.75 | 495079 (22%) | 509223 (42%) | nd |
| sesquiterpene I (chamigrene) | 14.028 | 168400 (8%) | 118789 (10%) | nd |

TABLE 2-continued

Terpenoid compounds detected in the in-vitro enzyme assays with valencene synthase purified from E. coli BL21 AI cells containing pAC-65-3 (thus expressing ValC), pET-16b-ValF (thus expressing ValF) or pACYCDuet-1 (negative blank).

| | Rf (min) | pAC-65-3 (invention) area | pET-16b-ValF (reference) area | pACYCDuet-1 (blank) area |
|---|---|---|---|---|
| valencene | 14.126 | 2228164 (100%) | 1207259 (100%) | nd |
| sesquiterpene III (selinene) | 14.103 | 164722 (7%) | nd | nd |
| sesquiterpene IV (panasinsen) | 14.479 | 69696 (3%) | 115944 (10%) | nd |
| sesquiterpene alcohol I (germacrene-D-ol) | 15.155 | 203027 (9%) | nd | nd |
| sesquiterpene alcohol II (eudesmadienol) | 16.225 | 63561 (3%) | 275093 (23%) | nd |
| farnesol | 16.79 | 530588 (24%) | 809363 (67%) | 798326 |

Rf: retention time;
area: peak surface area in GC-MS chromatogram;
percentage indicates the percentage of the area relative to the area of the valencene;
nd: not detected.
Compound names between brackets indicate tentative identification.

The valencene area of the preparation expressing ValC corresponds to 2.7 ug/mL (as calculated by comparison to a valencene standard), while the valencene area for the ValF preparation corresponds to 1.5 ug/mL. Thus, the preparation according to the invention produced 1.8 times more valencene than the ValF preparation. To verify whether this was due to the amounts of valencene synthase in both preparations or to a difference in specific activity of both valencene synthases, total protein content of both enzyme preparations was compared based on the absorption at 280 nm (A280) of a 10-fold dilution in Resuspension buffer. For the preparation comprising the ValC, A280 was 0.12; in case of ValF, A280 was 0.14; and in case of the blank, A280 was 0.18. The purified proteins were also analysed by electrophoresis on a 12.5% poly-acryl amide gel with SDS, together with a protein marker (Fermentas, PAGE Ruler pre-stained protein ladder). After Coomassie Brilliant Blue staining, in each lane a number of protein bands could be observed. Bands of various mobility were observed in the blank sample as well as in the other two samples. Between 55 kilodalton and 72 kilodalton, bands that were specific for ValC and ValF were observed (not present in the blank sample). These bands probably reflect the produced sesquiterpene synthases. In the ValC sample, the specific band contained about 5% of the total protein, whereas in the ValF sample, the specific band contained about 20% of the total protein, as estimated by visual inspection. This indicated that the concentration of sesquiterpene synthase in the ValF preparation was considerably higher, possibly more than twofold higher, than in the ValC preparation. Despite the lower quantity of enzyme, the preparation comprising ValC produced considerably more valencene (see above). Thus, this example shows that a valencene synthase according to the invention has a considerably higher specific enzymatic activity with respect to valencene synthesis than a known valencene synthase from citrus.

Besides valencene also other sesquiterpenes were formed by the two valencene synthases. The relative amount (as compared to the area of valencene) of germacrene-A (observed as beta-elemene due to thermal rearrangement in the injection port of the GC-MS), the major by-product formed with both synthases, appeared to be 22% with the preparation expressing ValC whereas this was 42% with the ValF containing preparation. Also the total relative amount of the sesquiterpene alcohols I and II with the preparation expressing ValC is approximately twofold lower than with the preparation expressing ValF, being 12% and 23%, respectively. Because the total relative amount of the other three sesquiterpenes formed (I, III and IV) are similar with both terpene synthases (ValC: 18%; ValF: 20%), this example also shows that a valencene according to the invention is significantly more specific with respect to formation of valencene compared to other terpenoids.

Example 3

Construction of R. sphaeroides Strains Producing Valencene or Amorphadiene

Cloning of Citrus×paradisi Valencene Synthase and Corresponding N-Terminal Fusions Construction of plasmids pBBR-K-PcrtE-valF-op, pBBR-K-PcrtE-valFpoR, pBBR-K-PcrtE-mbp-valFpoR, pBBR-K-PcrtE-nusA-valFpoR, pBBR-K-PcrtE-set-valFpoR, and pBBR-K-PcrtE-trx-valFpoR The following nucleotide fragments were prepared by custom synthesis by DNA 2.0 Inc. (Menlo Park, Calif., USA): valF (SEQ ID NO: 7) coding for valencene synthase ValF from Citrus×paradisi (Accession number: CAG29905), valFpoR (SEQ ID NO: 8) coding for valencene synthase ValF from Citrus×paradisi with a two-amino acid C-terminal extension (referred to as ValFpoR) (SEQ ID NO: 9), mbp-valFpoR (SEQ ID NO: 10) coding for a fusion of maltose-binding protein (MBP) from Escherichia coli at its C-terminus to the N-terminus of valencene synthase ValFpoR (SEQ ID NO: 11), nusA-valFpoR (SEQ ID NO: 12) coding for a fusion of nitrogen utilization protein (NusA) from Escherichia coli at its C-terminus to the N-terminus of valencene synthase ValFpoR (SEQ ID NO: 13), set-valFpoR (SEQ ID NO: 24) coding for a fusion of solubility enhancing tag (SET) at its C-terminus to the N-terminus of valencene synthase ValFpoR (SEQ ID NO: 25), and trx-valFpoR (SEQ ID NO: 14) coding for a fusion of thioredoxin (Trx) from Escherichia coli at its C-terminus to the N-terminus of valencene synthase ValFpoR (SEQ ID NO: 15). All synthetic gene sequences were optimized in terms of codon usage for improved heterologous protein expression in Rhodobacter sphaeroides, and comprised an NdeI restriction site at their 5'-end, which also provided the ATG start codon, and a BamHI restriction site at their 3'-end downstream of stop codons. Also an AseI restriction site, which provides NdeI-compatible cohesive ends upon digestion, was introduced in the linkage region between the 3'-end of the genes encoding the fusion proteins MBP, NusA, SET, and Trx, and the 5'-end of the gene coding for ValFpoR. Synthetic nucleotides valF, valFpoR, mbp-valFpoR, nusA-valFpoR, set-valFpoR, and trx-valFpoR were digested with NdeI and BamHI and the resulting DNA fragments were ligated to NdeI/BamHI-digested plasmid vector pBBR-K-PcrtE, yielding plasmids pBBR-K-PcrtE-valF-op, pBBR-K-PcrtE-valFpoR, pBBR-K-PcrtE-mbp-valFpoR, pBBR-K-PcrtE-nusA-valFpoR, pBBR-K-PcrtE-set-valFpoR, and pBBR-K-PcrtE-trx-valFpoR. In all these plasmids the kanamycin resistance gene and the valencene synthase-encoding gene are transcribed in opposite directions. The construction of plasmid vector pBBR-K-PcrtE is described in detail in Example 6 (page 91, lines 12-27) of WO 02/099095.
Construction of Plasmids pBBR-K-PcrtE-valF, pBBR-K-PcrtE-valFpoR-rev, pBBR-K-PcrtE-mbp-valFpoR-rev, pBBR-K-PcrtE-nusA-valFpoR-rev, pBBR-K-PcrtE-set-valFpoR-rev, and pBBR-K-PcrtE-trx-valFpoR-rev Gene inserts carrying the translationally fused or native valencene synthase genes were excised from parent plasmids pBBR-K-PcrtE-valF-op, pBBR-K-PcrtE-valFpoR, pBBR-K-PcrtE-mbp-valFpoR, pBBR-K-PcrtE-nusA-valFpoR, pBBR-K-PcrtE-set-valFpoR, and pBBR-K-PcrtE-trx-valFpoR as MlyI/PshAI-blunt ended fragments with respective lengths of 2.4 kilobases, 2.4 kilobases, 3.5 kilobases, 3.9 kilobases, 2.5 kilobases, and 2.7 kilobases. Plasmid vector pBBR-K-PcrtE was digested with EcoRI and BamHI, the resulting 5'-overhangs were blunted using DNA polymerase I, large (Klenow) fragment, the larger 4.2 kilobases DNA fragment was gel-purified and ligated to each of the above nucleotide fragments encoding PcrtE-valF, PcrtE-valFpoR, PcrtE-mbp-valFpoR, PcrtE-nusA-valFpoR, PcrtE-set-valFpoR, and PcrtE-trx-valFpoR. The orientation of the insert was checked and the plasmids which carried the valencene synthase-encoding gene in the same orientation as the kanamycin resistance gene were designated pBBR-K-PcrtE-valF, pBBR-K-PcrtE-valFpoR-rev, pBBR-K-PcrtE-mbp-valFpoR-rev, pBBR-K-PcrtE-nusA-valFpoR-rev, pBBR-K-PcrtE-set-valFpoR-rev, and pBBR-K-PcrtE-trx-valFpoR-rev.
Construction of Plasmid pBBR-K-PcrtE-mbp-valF-op Plasmid pBBR-K-PcrtE-valF was digested with NdeI and BamHI and the smaller 1.7 kilobase DNA fragment encoding ValF was ligated to the larger of the two fragments generated upon AseI/BamHI-digestion of plasmid vector pBBR-K-PcrtE-mbp-valFpoR, resulting in pBBR-K-PcrtE-mbp-valF-op, in which the Citrus valencene synthase ValF is expressed as a translational fusion to the C-terminus of maltose-binding protein (MBP) from *Escherichia coli*. In this newly constructed plasmid, the kanamycin resistance gene and the valencene synthase-encoding gene are transcribed in the opposite orientation.
Construction of Plasmid pBBR-K-PcrtE-mbp-valF Plasmid pBBR-K-PcrtE-valF was digested with NdeI and BamHI and the smaller 1.7 kilobase DNA fragment encoding ValF was ligated to the larger of the two fragments generated upon AseI/BamHI-digestion of plasmid vector pBBR-K-PcrtE-mbp-valFpoR-rev, resulting in plasmid pBBR-K-PcrtE-mbp-valF containing the mbp-valF gene (SEQ ID NO: 16) encoding the Citrus valencene synthase ValF translationally fused to the C-terminus of maltose-binding protein (MBP) from *Escherichia coli* (SEQ ID NO: 17). In this newly constructed plasmid, the kanamycin resistance gene and the valencene synthase-encoding gene are transcribed in the same orientation.
Cloning of Mevalonate (mev) Operon from *Paracoccus zeaxanthinifaciens*
Construction of Plasmids pBBR-K-mev-op-4-89-PcrtE-valF-op, pBBR-K-mev-op-4-89-PcrtE-valFpoR, pBBR-K-mev-op-4-89-PcrtE-mbp-valF-op, pBBR-K-mev-op-4-89-PcrtE-mbp-valFpoR, pBBR-K-mev-op-4-89-PcrtE-nusA-valFpoR, pBBR-K-mev-on-4-89-PcrtE-set-valFpoR, and pBBR-K-mev-op-4-89-PcrtE-trx-valFpoR Plasmid pBBR-K-mev-op-4-89-PcrtE-ddsA$_{wt}$ was used as the source of the mutated mevalonate operon from *Paracoccus zeaxanthinifaciens*. The construction of plasmid pBBR-K-mev-op-4-89-PcrtE-ddsA$_{wt}$ is described in detail in Example 3 (page 15, lines 4-31) of WO 06/018211.

The mev operon insert was excised from parent plasmid pBBR-K-mev-op-4-89-PcrtE-ddsA$_{wt}$ as an RsrII/XbaI-fragment, the XbaI-generated 5'-overhang was blunted using DNA polymerase I large (Klenow) fragment prior to treatment with RsrII. The resulting 7.0-kilobase nucleotide fragment was ligated to the RsrII/MlyI-digested plasmid vectors pBBR-K-PcrtE-valF-op, pBBR-K-PcrtE-valFpoR, pBBR-K-PcrtE-mbp-valF-op, pBBR-K-PcrtE-mbp-valFpoR, pBBR-K-PcrtE-nusA-valFpoR, pBBR-K-PcrtE-set-valFpoR, and pBBR-K-PcrtE-trx-valFpoR, yielding plasmids pBBR-K-mev-op-4-89-PcrtE-valF-op, pBBR-K-mev-op-4-89-PcrtE-valFpoR, pBBR-K-mev-op-4-89-PcrtE-mbp-valF-op, pBBR-K-mev-op-4-89-PcrtE-mbp-valFpoR, pBBR-K-mev-op-4-89-PcrtE-nusA-valFpoR, pBBR-K-mev-op-4-89-PcrtE-set-valFpoR, and pBBR-K-mev-op-4-89-PcrtE-trx-valFpoR, respectively. In those newly constructed plasmids, the mev operon insert and the valencene synthase-encoding, gene are transcribed in opposite orientations.
Construction of Plasmids pBBR-K-mev-op-4-89-PcrtE-valF, pBBR-K-mev-op-4-89-PcrtE-valFpoR-rev, pBBR-K-mev-op-4-89-PcrtE-mbp-valF, pBBR-K-mev-op-4-89-PcrtE-mbp-valFpoR-rev, pBBR-K-mev-op-4-89-PcrtE-nusA-valFpoR-rev, pBBR-K-mev-op-4-89-PcrtE-set-valFpoR-rev, and pBBR-K-mev-op-4-89-PcrtE-trx-valFpoR-rev The mev operon insert was excised from parent plasmid pBBR-K-mev-op-4-89-PcrtE-ddsA$_{wt}$ as an RsrII/BlpI-fragment and the resulting 7.3-kilobase nucleotide fragment was ligated to the RsrII/BlpI-digested plasmid vectors pBBR-K-PcrtE-valF, pBBR-K-PcrtE-valFpoR-rev, pBBR-K-PcrtE-mbp-valF, pBBR-K-PcrtE-mbp-valFpoR-rev, pBBR-K-PcrtE-nusA-valFpoR-rev, pBBR-K-PcrtE-set-valFpoR-rev, and pBBR-K-PcrtE-trx-valFpoR-rev, yielding plasmids pBBR-K-mev-op-4-89-PcrtE-valF, pBBR-K-mev-op-4-89-PcrtE-valFpoR-rev, pBBR-K-mev-op-4-89-PcrtE-mbp-valF, pBBR-K-mev-op-4-89-PcrtE-mbp-valFpoR-rev, pBBR-K-mev-op-4-89-PcrtE-nusA-valFpoR-rev, pBBR-K-mev-op-4-89-PcrtE-set-valFpoR-rev, and pBBR-K-mev-op-4-89-PcrtE-trx-valFpoR-rev, respectively. In those newly constructed plasmids, the kanamycin resistance gene, the mev operon insert, and the valencene synthase-encoding gene are transcribed in the same orientation.
Cloning of *Chamaecyparis nootkatensis* Valencene Synthase and Corresponding N-Terminal Fusions
Construction of Plasmids pBBR-K-PcrtE-valC-opt, pBBR-K-PcrtE-valC-opt-short, pBBR-K-PcrtE-mbp-valC-opt, and pBBR-K-PcrtE-mbp-valC-opt-short Two nucleic acid fragments encoding the valencene synthase from *Chamaecyparis nootkatensis* (ValC) were prepared by custom synthesis by DNA 2.0 Inc. Both synthetic gene sequences were optimized in terms of codon usage for improved heterologous protein expression in *Rhodobacter* sphaeroides, and comprised an NdeI restriction site at their 5'-end, which also provided the ATG start codon, and a BamHI restriction site at their 3'-end downstream of stop codons. The first nucleic acid fragment contained an ORF corresponding to the full-length valC gene (valC-opt) (SEQ ID NO: 18) coding for the full-length version of valencene synthase ValC from *C. nootkatensis* (SEQ ID NO: 4). The second nucleic acid fragment contained an ORF corresponding to a truncated version of the valC gene (valC-opt-short) (SEQ ID NO: 19) coding for a shorter variant of the *C. nootkatensis* valencene synthase that lacked 16 amino acids from its N-terminus, ValC-short (SEQ ID NO: 2).

The synthetic nucleic acid fragments containing valC-opt and valC-opt-short were digested with NdeI and BamHI. The resulting DNA fragments were ligated to the larger of the two fragments generated upon NdeI/BamHI-digestion of plasmid vector pBBR-K-PcrtE-valFpoR-rev, resulting in pBBR-K-PcrtE-valC-opt and pBBR-K-PcrtE-valC-opt-short, respectively. In these two newly constructed plasmids, the kanamycin resistance gene and the valencene synthase-encoding gene are transcribed in the same orientation.

The synthetic nucleic acid fragments containing valC-opt and valC-opt-short were again digested with NdeI and BamHI. Subsequently, the resulting DNA fragments were ligated to the larger of the two fragments generated upon AseI/BamHI-digestion of plasmid vector pBBR-K-PcrtE-mbp-valFpoR-rev, resulting in pBBR-K-PcrtE-mbp-valC-opt containing the mbp-valC-opt gene (SEQ ID NO: 20) and pBBR-K-PcrtE-mbp-valC-opt-short containing the mbp-valC-opt-short gene (SEQ ID NO: 22), respectively. In plasmid pBBR-K-PcrtE-mbp-valC-opt the full-length version of ValC is expressed as translational fusion at the C-terminus of the maltose-binding protein (MBP) from *Escherichia coli* (SEQ ID NO: 21), whereas in plasmid pBBR-K-PcrtE-mbp-valC-opt-short the truncated version of ValC is expressed as translational fusion at the C-terminus of the maltose-binding protein (MBP) from *Escherichia coli* (SEQ ID NO: 23). In these two newly constructed plasmids, the kanamycin resistance gene and the valencene synthase-encoding gene are transcribed in the same orientation.

Cloning of Mevalonate (mev) Operon from *Paracoccus zeaxanthinifaciens* into Plasmids Encoding Valencene Synthase from *Chamaecyparis nootkatensis*

Construction of Plasmids pBBR-K-mev-op-4-89-PcrtE-mbp-valC-opt and pBBR-K-mev-op-4-89-PcrtE-mbp-valC-opt-short The mev operon insert was excised from parent plasmid pBBR-K-mev-op-4-89-PcrtE-ddsA$_{wt}$ as an RsrII/BlpI-fragment and the resulting 7.3-kilobase nucleotide fragment was ligated to RsrII/BlpI-digested plasmid vectors pBBR-K-PcrtE-mbp-valC-opt and pBBR-K-PcrtE-mbp-valC-opt-short, resulting in plasmids pBBR-K-mev-op-4-89-PcrtE-mbp-valC-opt and pBBR-K-mev-op-4-89-PcrtE-mbp-valC-opt-short, respectively. In these newly constructed plasmids, the kanamycin resistance gene, the mev operon insert, and the valencene synthase-encoding gene are transcribed in the same orientation.

Cloning of *Artemisia annua* Amorphadiene Synthase and Corresponding N-Terminal Fusion Construction of Plasmids pBBR-K-PcrtE-aaas and pBBR-K-PcrtE-mbp-aaas A synthetic nucleic acid fragment carrying a gene (aaas) (SEQ ID NO: 26) encoding the amorphadiene synthase Aaas from *Artemisia annua* (SEQ ID NO: 27) was prepared by custom synthesis by DNA 2.0 Inc. The synthetic gene sequence was optimized in terms of codon usage for improved heterologous protein expression in *Rhodobacter sphaeroides* and comprised an NdeI restriction site at its 5'-end, which also provided the ATG start codon, and a BamHI restriction site at its 3'-end downstream of stop codons.

The synthetic nucleic acid fragment containing aaas was digested with NdeI and BamHI. The resulting DNA fragment was ligated to the larger of the two fragments generated upon NdeI/BamHI-digestion of plasmid vector pBBR-K-PcrtE-valFpoR-rev, resulting in pBBR-K-PcrtE-aaas. In this newly constructed plasmid, the kanamycin resistance gene and the amorphadiene synthase-encoding gene are transcribed in the same orientation.

The synthetic nucleic acid fragment containing aaas was again digested with NdeI and BamHI. Subsequently, the resulting DNA fragment was ligated to the larger of the two fragments generated upon AseI/BamHI-digestion of plasmid vector pBBR-K-PcrtE-mbp-valFpoR-rev, resulting in pBBR-K-PcrtE-mbp-aaas containing the mbp-aaas gene (SEQ ID NO: 28). In plasmid pBBR-K-PcrtE-mbp-aaas; Aaas is expressed as translational fusion at the C-terminus of the maltose-binding protein (MBP) from *Escherichia coli* (SEQ ID NO: 29). In this newly constructed plasmid, the kanamycin resistance gene and the amorphadiene synthase-encoding gene are transcribed in the same orientation.

Transformation of *Rhodobacter sphaeroides*

Transformation of *E. coli* S17-1 with plasmids and subsequent transfer of plasmids from S17-1 to *R. sphaeroides* Rs265-9c by conjugation were performed using standard procedures (Nishimura et al., Nucl. Acids Res. (1990) 18, 6169; Parke, Gene (1990) 93, 135-137). *R. sphaeroides* Rs265-9c recipient strain was grown in RÄ-medium. The composition and preparation of medium RÄ is summarized in Table 3. In parallel, *E. coli* S17-1 donor strain that carries the plasmid to be transferred was grown in LB-broth containing the appropriate antibiotic. For the conjugation, 450 µL culture aliquots of the *R. sphaeroides* Rs265-9c recipient strain and of the *E. coli* S17-1 donor strain were mixed together, and then pelleted by centrifugation. The supernatant was discarded. Cells were washed twice with fresh RÄ-medium to remove the antibiotics, and then resuspended in 0.05 mL fresh RÄ-medium and spotted onto a PY-plate. The composition and preparation of medium PY is summarized in Table 4. After 4-5 h incubation at 30° C. the cells were harvested with an inoculating loop and resuspended in 0.3 mL of RÄ-medium. Dilutions of this suspension were spread onto RÄ-plates containing the appropriate antibiotic and incubated at 30° C. for 2-3 days. Colonies were picked from the plates, streaked onto RS102-plates containing the appropriate antibiotic, and incubated at 30° C. for 2-3 days to obtain single colonies. One single colony from each clone (putatively transformed cells of *R. sphaeroides* Rs265-9c) was again grown in liquid RS102 medium containing the appropriate antibiotic and the presence of the expected plasmid was confirmed by PCR using appropriate primers. The final transformants were preserved by adding glycerol to the culture (15% v/v) and freezing at −80° C.

TABLE 3

| Composition and preparation of medium RÄ | |
|---|---|
| Component | Amount per litre distilled water |
| Medium RÄ | |
| 1. Malic acid | 3 g |
| 2. MgSO$_4$•7H$_2$O | 0.2 g |
| 3. (NH$_4$)$_2$SO$_4$ | 1.2 g |

TABLE 3-continued

Composition and preparation of medium RÄ

| Component | Amount perlitre distilled water |
|---|---|
| 4. $CaCl_2 \cdot 2H_2O$ | 0.07 g |
| 5. Microelements solution | 1.5 mL |
| 6. Vitamins solution | 8 mL |
| 7. Phosphate buffer solution | 20 mL |

Components 1-5 are mixed together, the final volume is adjusted to 1 litre, and the pH is adjusted to 6.9 with 0.5M NaOH. The resulting base medium is then sterilized by filtration through a 0.22 micron membrane; 8 mL of sterile vitamins solution and 20 mL of sterile phosphate buffer solution (see below) are added to give the final medium RA. For solid medium, the 1 litre base medium mentioned above plus 20 g agar are first mixed together and autoclaved. After the medium is cooled down to about 60° C., the sterile vitamins and phosphate buffer solutions are added and the molten medium is dispensed into sterile Petri plates.

Microelements solution

| | |
|---|---|
| Fe(II) citrate | 500 mg |
| $MnCl_2 \cdot 4H_2O$ | 20 mg |
| $ZnCl_2$ | 5 mg |
| LiCl | 5 mg |
| KBr | 2.5 mg |
| KI | 2.5 mg |
| $CuSO_4 \cdot 5H_2O$ | 0.23 mg |
| $Na_2MoO_4$ | 0.851 mg |
| $CoCl_2 \cdot 6H_2O$ | 5 mg |
| $SnCl_2 \cdot 2H_2O$ | 0.5 mg |
| $BaCl_2 \cdot 2H_2O$ | 0.59 mg |
| $AlCl_3$ | 1 mg |
| $H_3BO_4$ | 10 mg |
| EDTA | 20 mg |

Sterilize by filtration through a 0.22 micron membrane, store at 4° C.

Vitamins solution

| | |
|---|---|
| Niacin | 200 mg |
| Thiamin-HCl | 400 mg |
| Nicotinamide | 200 mg |
| Biotin | 8 mg |

Sterilize by filtration through a 0.22 micron membrane, store at 4° C.

Phosphate buffer solution

| | |
|---|---|
| $KH_2PO_4$ | 600 mg |
| $K_2HPO_4$ | 900 mg |

Sterilize by filtration through a 0.22 micron membrane, store at 4° C.

TABLE 4

Composition and preparation of medium PY plates
Medium PY

| Component | Amount per litre distilled water |
|---|---|
| 1. Bacto peptone | 10 g |
| 2. Yeast extract | 0.5 g |
| 3. $CaCl_2$ (0.4 M) | 5 mL |
| 4. $MgCl_2$ (0.4 M) | 5 mL |
| 5. $FeSO_4$ (0.5%) | 2.4 mL |
| 6. Agar | 20 g |
| 7. $H_2O$ | 990 mL |

Components 1-7 are mixed together, the pH is adjusted to 7.0 with 0.5 M NaOH, and the mixture is autoclaved. After the medium is cooled down to about 60° C., the molten medium is dispensed into sterile Petri plates.

Example 4

Cultivation of Rhodobacter sphaeroides Strains Under Standard Shake-Flask Conditions and Evaluation of Valencene Production Preparation of Frozen Cell Stocks Frozen cell stocks of R. sphaeroides strains were prepared by introducing a loop-full of frozen cells into 2 mL RS102 medium containing 50 mg/L kanamycin (if applicable for plasmid maintenance). The preculture was grown at 30° C. with agitation at 220 rpm for 24 h. A 250 μL aliquot of preculture was transferred to 25 mL of RS102 medium containing 50 mg/L kanamycin to initiate (t=0) growth. The 25 mL main culture was grown in a 250-mL baffled Erlenmeyer flasks at 30° C. with agitation at 220 rpm for about 24 h. Bacterial cell cultures were mixed with sterile anhydrous glycerol and sterile water so as to reach a final glycerol content of 25% and a final optical density at 660 nanometers ($OD_{660}$) of 12. The resulting cell suspension was aseptically distributed in 1.2 mL-aliquots into 2 mL-cryovials then frozen at −80° C. until used.

Shake-flask Procedure

Inoculants of R. sphaeroides strains were started by introducing 250 μL of a thawed and homogenized frozen cell stock into 25 mL of RS102 medium containing 50 mg/L of kanamycin (if applicable for plasmid maintenance). Precultures were grown in 250-mL baffled Erlenmeyer flasks for 24-28 h at 30° C. with agitation at 220 rpm. A suitable aliquot of preculture was transferred to 22.5 mL of RS102 medium containing 50 mg/L of kanamycin (if applicable for plasmid maintenance) to initiate (t=0) shake-flask experiments with an initial optical density at 660 nm ($OD_{660}$) of 0.16. Main cultures were grown in 250-mL baffled Erlenmeyer flasks at 30° C. with agitation at 220 rpm. After 8 h cultivation, 2.5 mL of n-dodecane were added to the bacterial culture. Shake-flask cultivation continued at 30° C. with agitation at 220 rpm for 72 h from inoculation. Each seed culture served to inoculate two duplicate shake-flasks with a final volume of 25 mL whole broth, composed of culture medium and n-dodecane for in situ product recovery. Samples (0.5 mL) of biphasic culture broth were removed at 24 h intervals and analyzed for growth ($OD_{660}$), pH, and glucose in supernatant. At the end of the experiments (t=72 h), the biphasic culture broth was analyzed for presence of valencene (see analytical methods below). At the end of the experiments, 10 μL of culture broth were aseptically plated on general cultivation count agar plates (Becton Dickinson GmbH, Heidelberg, Germany) and incubated at 37° C. for 24 h to test for contamination.

Analytical Methods

Sample Preparation for Analysis of Isoprenoid Content in Organic Phase

In a typical procedure, 10 mL whole broth samples were transferred to a disposable sterile 15 mL polypropylene conical tube. The organic and aqueous phases were separated upon ultracentrifugation for 30 min. The organic phase was transferred to amber chromatography vials for analysis by gas chromatography (see below). Product yields were determined based on calibration curves established upon analysis of three standard solutions of authentic valencene dissolved in analytical grade n-dodecane.

Sample Preparation for Analysis of Isoprenoid Content in Whole Broth

In a typical procedure, 400 μL whole broth samples were transferred to a disposable sterile 15 mL polypropylene conical tube, treated with 4 mL acetone, vigorously shaken on an IKA Vibrax orbital shaker at 1,500 rpm for 20 minutes, then incubated in a bench top ultrasonic bath for 30 min at ambient temperature. Finally samples were centrifuged at maximum speed and the supernatant transferred to amber chromatography vials for analysis by gas chromatography (see below). Product yields were determined based on calibration curves established using a standard solution of authentic valencene prepared as follows: 5 mL of authentic valencene were added into a 100 mL volumetric flask and dissolved with analytical grade n-dodecane. Aliquots of valencene standard solution (20, 40 and 80 μl) were transferred to disposable sterile 15 mL polypropylene conical tubes, treated with deionized sterile water (380, 360, and 320 µL respectively) and 4 mL acetone. Each mixture was homogenized vigorously on a vortex shaker then transferred to amber chromatography vials for analysis by gas chromatography, wherefrom a calibration curve was derived.

Gas Chromatography

Gas chromatography was performed on a Hewlett-Packard GC 6890 instrument equipped with a Restek Rtx-5 capillary column (30.0 m×0.32 mm×0.25 µm). The injector and FID detector temperatures were set to 300° C. and 250° C., respectively. Gas flow through the column was set at 2.7 mL/min. The oven initial temperature was held at 70° C. for 2 min, increased to 180° C. at a rate of 10° C./min, further increased to 300° C. at a rate of 40° C./min, then cooled down to 60° C. and held at that temperature for 3 min until the next injection. Injected sample volume was 1 µL with a 4:1 split-ratio. Product yields were determined based on calibration curves established for authentic samples.

Example 5

In vivo Comparison of C. nootkatensis Valencene Synthase (Invention) and Citrus Valencene Synthase (Reference)

R. sphaeroides strains Rs265-9c (blank strain, no plasmid), Rs265-9c/pBBR-K-PcrtE-mbp-valF (reference strain), Rs265-9c/pBBR-K-mev-op-4-89-PcrtE-mbp-valF (reference strain also expressing the mutated mevalonate operon mev from Paracoccus zeaxanthinifaciens), and Rs265-9c/pBBR-K-PcrtE-mbp-valC-opt, Rs265-9c/pBBR-K-PcrtE-mbp-valC-opt-short, Rs265-9c/pBBR-K-mev-op-4-89-PcrtE-mbp-valC-opt, and Rs265-9c/pBBR-K-mev-op-4-89-PcrtE-mbp-valC-opt-short (four strains expressing a nucleic acid sequence encoding a valencene synthase according to the invention), were grown under standard shake flask cultivation condition as described above. Several clones of each transformed R. sphaeroides strain were tested for valencene production and each shake-flask experiment was run in duplicate, unless stated otherwise. The valencene titre is reported in mg/L n-dodecane, wherein the organic phase n-dodecane constituted 10% (v/v) of the whole broth.

The results of these in vivo tests are given in Table 5.

TABLE 5

In vivo formation of valencene and germacrene A in shake flask experiments employing R. sphaeroides containing plasmids pBBR-K-PcrtE-mbp-valF, pBBR-K-PcrtE-mbp-valC-opt, pBBR-K-mev-op-4-89-PcrtE-mbp-valF, or pBBR-K-mev-op-4-89-PcrtE-mbp-valC-opt, and R. sphaeroides without plasmid.

| | Rhodobacter sphaeroides strain | Valencene in n-dodecane (mg/L) | | Germacrene A in n-dodecane (mg/L)$^a$ | | V/G ratio$^b$ |
|---|---|---|---|---|---|---|
| | | Average Titre | Std Dev | Average Titre | Std Dev | |
| 1 | Rs265-9c/pBBR-K-PcrtE-mbp-valF$^c$ | 25 | 1 | 38 | 2 | 0.67 |
| 2 | Rs265-9c/pBBR-K-PcrtE-mbp-valC-opt$^d$ | 575 | 35 | 176 | 10 | 3.3 |
| 3 | Rs265-9c/pBBR-K-mev-op-4-89-PcrtE-mbp-valF$^e$ | 249 | 13 | 259 | 28 | 0.96 |
| 4 | Rs265-9c/pBBR-K-mev-op-4-89-PcrtE-mbp-valC-opt$^d$ | 3519 | 368 | 983 | 111 | 3.6 |
| 5 | Rs265-9c | 0.0 | 0.0 | 0.6 | 0.1 | 0 |

$^a$Quantified as beta-elemene upon Cope thermal rearrangement of substrate germacrene A in the GC injector (300° C.).
$^b$Valencene (V) to germacrene A (G) ratio.
$^c$Valencene production for each strain was tested on seven clones in duplicate.
$^d$Valencene production for each strain was tested on six clones in duplicate.
$^e$Valencene production for each strain was tested on four clones in duplicate.

Whereas cultivation of the empty R. sphaeroides strain Rs265-9c did not result in detectable amounts of valencene (entry 5), the strain transformed with plasmid pBBR-K-PcrtE-mbp-valF expressing ValF from Citrus×paradisi with the E. coli MBP at its N-terminus formed 25 mg/L valencene (entry 1). The strain with the analogous plasmid pBBR-K-PcrtE-mbp-valC-opt expressing ValC from Chamaecyparis nootkatensis with the E. coli MBP at its N-terminus resulted in a valencene titre of 575 mg/L (entry 2), a 23-fold increase compared to the MBP-ValF expressing strain. Also in the presence of the mutated mevalonate operon from Paracoccus zeaxanthinifaciens expression of MBP-ValC led to significantly higher valencene titres than MBP-ValF. While R. sphaeroides containing pBBR-K-mev-op-4-89-PcrtE-mbp-valF produced 249 mg/L valencene (entry 3), 3519 mg/L was formed in case of R. sphaeroides containing pBBR-K-mev-op-4-89-PcrtE-mbp-valC-opt (entry 4), a 14-fold increase. Thus, this example shows that a valencene synthase according to the invention leads to a considerably higher in vivo valencene production than a known valencene synthase from citrus.

The novel valencene synthase ValC also forms much less germacrene-A than the Citrus×paradisi valencene synthase ValF. The valencene to germacrene A (observed as beta-elemene due to thermal rearrangement in the injection port of the GC-MS) ratio in the n-dodecane layer appeared to be 0.67 and 0.96 for R. sphaeroides Rs265-9c with plasmids pBBR-K-PcrtE-mbp-valF and pBBR-K-mev-op-4-89-PcrtE-mbp-valF, respectively, indicating that under these conditions expression of MBP-ValF results in slightly more germacrene-A than valencene (entries 1 & 3). This valencene to germacrene A ratio increased to 3.3 and 3.6 when R. sphaeroides with plasmids pBBR-K-PcrtE-mbp-valC-opt and pBBR-K-mev-op-4-89-PcrtE-mbp-valC-opt was cultivated (entries 2 & 4). Thus, this example shows that a valencene according to the invention is also significantly more specific with respect to formation of valencene compared to germacrene A than the Citrus×paradisi valencene synthase.

Example 6

In vivo Comparison of C. nootkatensis Full-Length Valencene Synthase (ValC) and C. nootkatensis N-Terminally Truncated Valencene Synthase (ValC-Short)

R. sphaeroides strains Rs265-9c (blank strain, no plasmid), Rs265-9c/pBBR-K-PcrtE-valC-opt (strain expressing the full-length valencene synthase gene valC-opt), and Rs265-9c/pBBR-K-PcrtE-valC-opt-short (strain expressing a truncated version of the valencene synthase gene valC-opt-short), as well as the *R. sphaeroides* strains expressing the corresponding valC genes but now translationally fused at their 5'-ends to the 3'-end of the *E. coli* mbp gene (Rs265-9c/pBBR-K-PcrtE-mbp-valC-opt and Rs265-9c/pBBR-K-PcrtE-mbp-valC-opt-short), were grown under the standard shake flask cultivation conditions as described above. Several clones of each of these five strains were tested for valencene production, and each shake-flask experiment was run in duplicate, unless stated otherwise. The valencene titre is reported in mg/L n-dodecane, wherein the organic phase n-dodecane constituted 10% (v/v) of the whole broth.

The results of these in vivo tests are presented in Table 6.

TABLE 6

In vivo formation of valencene in shake flask experiments employing *R. sphaeroides* containing plasmids pBBR-K-PcrtE-mbp-valC-opt, pBBR-K-PcrtE-mbp-valC-opt-short, pBBR-K-PcrtE-valC-opt, and pBBR-K-PcrtE-valC-opt-short, and *R. sphaeroides* without plasmid.

| | | Valencene in n-dodecane (mg/L) | |
|---|---|---|---|
| | *Rhodobacter sphaeroides* strain | Average Titre | Std Dev |
| 1 | Rs265-9c/pBBR-K-PcrtE-mbp-valC-opt[a] | 575 | 35 |
| 2 | Rs265-9c/pBBR-K-PcrtE-mbp-valC-opt-short[b] | 592 | 38 |
| 3 | Rs265-9c/pBBR-K-PcrtE-valC-opt[c] | 299 | 22 |
| 4 | Rs265-9c/pBBR-K-PcrtE-valC-opt-short[a] | 20 | 5 |
| 5 | Rs265-9c | 0.0 | 0.0 |

[a]Valencene production for each strain was tested on six clones in duplicate.
[b]Valencene production for each strain was tested on four clones in duplicate.
[c]Valencene production for each strain was tested on five clones in duplicate.

The results in Table 6 show that cultivation of the *R. sphaeroides* strains expressing the full-length and the N-terminally truncated version of the *C. nootkatensis* valencene synthase with an N-terminal MBP-tag leads to quite similar valencene titres, i.e. 575 and 592 mg/L, respectively (entries 1 & 2). When expressed without N-terminal MBP-tag, however, very different valencene titres are obtained. While cultivation of the *R. sphaeroides* strain containing plasmid pBBR-K-PcrtE-valC-opt, thus forming the un-tagged full-length ValC, resulted in 299 mg/L valencene, which is a factor 1.9 lower than with the corresponding MBP-tagged ValC, only 20 mg/L valencene was obtained by cultivation of strain Rs265-9c/pBBR-K-PcrtE-valC-opt-short expressing the untagged and N-terminally truncated ValC. This is a factor 30 lower than with the equivalent MBP-tagged ValC-short.

Thus, this example proofs that a valencene synthase according to the current invention can be expressed in active form in its native form, so without use of an N-terminal tag-peptide. This example moreover shows that an increased terpenoid titre is obtainable by expressing a valencene synthase according to the current invention with an N-terminal tag-peptide; the effect of such N-terminal tag-peptide is more profound in case of expression of an N-terminally truncated version of a valencene synthase according to the current invention.

Example 7

In vivo Comparison of the Expression of a Valencene Synthase with an N-Terminal Tag-Peptide (Invention) and without Such Tag-Peptide (Reference)

*R. sphaeroides* strains Rs265-9c (blank strain, no plasmid), Rs265-9c/pBBR-K-PcrtE-valFpoR, Rs265-9c/pBBR-K-PcrtE-valFpoR-rev, and Rs265-9c/pBBR-K-mev-op-4-89-PcrtE-valFpoR-rev (three reference strains, no N-terminal tag-peptide), Rs265-9c/pBBR-K-PcrtE-mbp-valFpoR, Rs265-9c/pBBR-K-PcrtE-mbp-valFpoR-rev, and Rs265-9c/pBBR-K-mev-op-4-89-PcrtE-mbp-valFpoR-rev (three strains expressing the *Citrus×paradisi* valencene synthase gene valFpoR translationally fused at its 5'-end to the 3'-end of the *E. coli* mbp gene), Rs265-9c/pBBR-K-PcrtE-nusA-valFpoR, Rs265-9c/pBBR-K-PcrtE-nusA-valFpoR-rev, and Rs265-9c/pBBR-K-mev-op-4-89-PcrtE-nusA-valFpoR-rev (three strains expressing the *Citrus×paradisi* valencene synthase gene valFpoR translationally fused at its 5'-end to the 3'-end of the *E. coli* nusA gene), Rs265-9c/pBBR-K-PcrtE-set-valFpoR, Rs265-9c/pBBR-K-PcrtE-set-valFpoR-rev, and Rs265-9c/pBBR-K-mev-op-4-89-PcrtE-set-valFpoR-rev (three strains expressing the *Citrus×paradisi* valencene synthase gene valFpoR translationally fused at its 5'-end to the 3'-end of the set tag), and Rs265-9c/pBBR-K-PcrtE-trx-valFpoR, Rs265-9c/pBBR-K-PcrtE-trx-valFpoR-rev, and Rs265-9c/pBBR-K-mev-op-4-89-PcrtE-trx-valFpoR-rev (three strains expressing the *Citrus×paradisi* valencene synthase gene valFpoR translationally fused at its 5'-end to the 3'-end of the *E. coli* trx gene) were grown under the standard shake flask cultivation condition as described above. Several clones of each transformed *R. sphaeroides* strain were tested for valencene production, and each shake-flask experiment was run in duplicate, unless stated otherwise. The valencene titre is reported in mg/L n-dodecane, wherein the organic phase n-dodecane constituted 10% (v/v) of the whole broth.

The results of this experiment are given in Tables 7-9.

TABLE 7

In vivo formation of valencene in shake flask experiments employing *R. sphaeroides* containing plasmids pBBR-K-PcrtE-mbp-valFpoR, pBBR-K-PcrtE-nusA-valFpoR, Rs265-9c/pBBR-K-PcrtE-set-valFpoR, pBBR-K-PcrtE-trx-valFpoR, and pBBR-K-PcrtE-valFpoR, and *R. sphaeroides* without plasmid.

| | Valencene in n-dodecane (mg/L) | |
|---|---|---|
| *Rhodobacter sphaeroides* Strain | Average Titre | Standard Deviation |
| Rs265-9c/pBBR-K-PcrtE-mbp-valFpoR[a] | 26.2 | 1.6 |
| Rs265-9c/pBBR-K-PcrtE-nusA-valFpoR[a] | 7.5 | 0.9 |
| Rs265-9c/pBBR-K-PcrtE-set-valFpoR[b] | 3.5 | 0.7 |
| Rs265-9c/pBBR-K-PcrtE-trx-valFpoR[a] | 16.6 | 1.7 |
| Rs265-9c/pBBR-K-PcrtE-valFpoR[a] | 0.5 | 0.6 |
| Rs265-9c[a] | 0.0 | 0.0 |

[a]Valencene production for each strain was tested on three different clones.
[b]Valencene production for each strain was tested on two different clones.

TABLE 8

In vivo formation of valencene in shake flask experiments employing R. sphaeroides containing plasmids pBBR-K-PcrtE-mbp-valFpoR-rev, pBBR-K-PcrtE-nusA-valFpoR-rev, pBBR-K-PcrtE-set-valFpoR-rev, pBBR-K-PcrtE-trx-valFpoR-rev, and pBBR-K-PcrtE-valFpoR-rev, and R. sphaeroides without plasmid.

| Rhodobacter sphaeroides Strain | Valencene in n-dodecane (mg/L) | |
|---|---|---|
| | Average Titre | Standard Deviation |
| Rs265-9c/pBBR-K-PcrtE-mbp-valFpoR-rev[a] | 22.2 | 2.8 |
| Rs265-9c/pBBR-K-PcrtE-nusA-valFpoR-rev[b] | 5.1 | 0.7 |
| Rs265-9c/pBBR-K-PcrtE-set-valFpoR-rev[a] | 3.0 | 0.5 |
| Rs265-9c/pBBR-K-PcrtE-trx-valFpoR-rev[c] | 6.2 | 0.8 |
| Rs265-9c/pBBR-K-PcrtE-valFpoR-rev[c] | 0.2 | 0.1 |
| Rs265-9c | 0.0 | 0.0 |

[a]Valencene production for each strain was tested on two different clones.
[b]Valencene production for each strain was tested on one clone.
[c]Valencene production for each strain was tested on three different clones.

TABLE 9

In vivo formation of valencene in shake flask experiments employing R. sphaeroides containing plasmids pBBR-K-mev-op-4-89-PcrtE-mbp-valFpoR-rev, pBBR-K-mev-op-4-89-PcrtE-nusA-valFpoR-rev, Rs265-9c/pBBR-K-mev-op-4-89-PcrtE-set-valFpoR-rev, pBBR-K-mev-op-4-89-PcrtE-trx-valFpoR-rev, and pBBR-K-mev-op-4-89-PcrtE-valFpoR-rev, and R. sphaeroides without plasmid.

| Rhodobacter sphaeroides Strain | Valencene in n-dodecane (mg/L) | |
|---|---|---|
| | Average Titre | Standard Deviation |
| Rs265-9c/pBBR-K-mev-op-4-89-PcrtE-mbp-valFpoR-rev[a] | 95.9 | 9.0 |
| Rs265-9c/pBBR-K-mev-op-4-89-PcrtE-nusA-valFpoR-rev[b] | 23.9 | 3.0 |
| Rs265-9c/pBBR-K-mev-op-4-89-PcrtE-set-valFpoR-rev[c] | 12.5 | 0.9 |
| Rs265-9c/pBBR-K-mev-op-4-89-PcrtE-trx-valFpoR-rev[c] | 66.9 | 5.8 |
| Rs265-9c/pBBR-K-mev-op-4-89-PcrtE-valFpoR-rev[d] | 0.4 | 0.1 |
| Rs265-9c | 0.0 | 0.0 |

[a]Valencene production for each strain was tested on six different clones.
[b]Valencene production for each strain was tested on four different clones.
[c]Valencene production for each strain was tested on three different clones.
[d]Valencene production for each strain was tested on two different clones.

The data in Tables 7-8 show that the R. sphaeroides strains in which the Citrus×paradisi valencene synthase ValF (with a two amino acid C-terminal extension ValFpoR) is expressed with an N-terminal tag-peptide, produced over 7-fold more valencene than the strains expressing ValFpoR in its native form. This positive effect of expressing ValFpoR with an N-terminal tag-peptide on the valencene production is most pronounced when the E. coli MBP is applied as peptide-tag.

A similar positive effect of a translational fusion of the valFpoR-rev gene at its 5'-end to the 3'-end of a tag-peptide encoding gene on the valencene production is observed with R. sphaeroides strains that co-express a mutated mevalonate operon from Paracoccus zeaxanthinifaciens (Table 9). Also in this case, this positive effect is largest when the E. coli mbp encoding gene is used as such tag-peptide encoding gene.

Thus, this example shows that expression of a terpene synthase enzyme comprising a tag-peptide at its N-terminus according to the invention in an isoprenoid producing organism leads to a higher isoprenoid production than when expressing the terpene synthase without such tag-peptide.

Example 8

In vivo Comparison of the Expression of an Amorphadiene Synthase with an N-Terminal Tag-Peptide (Invention) and without Such Tag-Peptide (Reference)

R. sphaeroides strains Rs265-9c (blank strain, no plasmid), Rs265-9c/pBBR-K-PcrtE-valF and Rs265-9c/pBBR-K-PcrtE-aaas (two reference strains, no N-terminal tag-peptide), Rs265-9c/pBBR-K-PcrtE-mbp-valF (a strain expressing the Citrus×paradisi valencene synthase gene valF translationally fused at its 5'-end to the 3'-end of the E. coli mbp gene) and Rs265-9c/pBBR-K-PcrtE-mbp-aaas (a strain expressing the Artemisia annua amorphadiene synthase gene aaas translationally fused at its 5'-end to the 3'-end of the E. coli mbp gene) were grown under the standard shake flask cultivation conditions as described above. Several clones of each transformed R. sphaeroides strain were tested for valencene or amorphadiene production, and each shake-flask experiment was run in duplicate, unless stated otherwise. The valencene and amorphadiene titre is reported in mg/L n-dodecane, wherein the organic phase n-dodecane constituted 10% (v/v) of the whole broth.

The results of this experiment are given in Table 10.

TABLE 10

In vivo formation of valencene or amorphadiene in shake flask experiments employing R. sphaeroides containing plasmids pBBR-K-PcrtE-mbp-valF, pBBR-K-PcrtE-mbp-aaas, pBBR-K-PcrtE-valF, and pBBR-K-PcrtE-aaas, and R. sphaeroides without plasmid.

| Rhodobacter sphaeroides Strain | Valencene or Amorphadiene in n-dodecane (mg/L) | |
|---|---|---|
| | Average Titre | Standard Deviation |
| Rs265-9c/pBBR-K-PcrtE-mbp-valF[a] | 25.4 | 1.4 |
| Rs265-9c/pBBR-K-PcrtE-mbp-aaas[b] | 666 | 72 |
| Rs265-9c/pBBR-K-PcrtE-valF[c] | 2.0 | 0.1 |
| Rs265-9c/pBBR-K-PcrtE-aaas[d] | 361 | 30 |
| Rs265-9c | 0.0 | 0.0 |

[a]Valencene production was tested on seven different clones.
[b]Amorphadiene production was tested on seven different clones.
[c]Valencene production was tested on one clone.
[d]Amorphadiene production was tested on one clone.

The data in Table 10 show that the R. sphaeroides strains in which the Citrus×paradisi valencene synthase ValF is expressed with an N-terminal MBP-tag, produced over 10-fold more valencene than the strains expressing ValF in its native form and that the R. sphaeroides strains in which the Artemisia annua amorphadiene synthase Aaas is expressed with an N-terminal MBP-tag, produced almost 2-fold more amorphadiene than the strains expressing Aaas in its native form. This positive effect of expressing a sesquiterpene synthase with an N-terminal MBP-tag on sesquiterpene production is thus clearly applicable to enzymes other than valencene synthase such as amorphadiene synthase.

Example 9

In vivo Expression of *C. nootkatensis* Valencene Synthase in Yeast

The full length open reading frame encoding the *C. nootkatensis* valencene synthase (ValC) was amplified from plasmid pAC-65-3 with the primers 65-3ATGDuetFw 5'-tatatggatccATGGCTGAAATGTTTAATGGAAATTCCAGC-3' [SEQ ID NO: 30] (BamHI recognition site underlined), and DuetAS1 5'-GATTATGCGGCCGTGTACAA-3' [SEQ ID NO: 31].

The annealing site of the 65-3ATGDuetFw primer was at the beginning of the native open reading frame of valC (SEQ ID NO:3) and the primer was designed to introduce a start codon and the BamHI site for cloning into the yeast vector. Reverse primer DuetAS was complementary to a region of the pAC-65-3 plasmid downstream of the valC open reading frame. The PCR conditions were as follows: initial denaturation of 45 s at 98° C. was followed by thirty PCR cycles of 10 s at 98° C., 20 s at 58° C. and 2 min at 72° C. which was again followed by a final extension of 5 min at 72° C. The final concentration of PCR reagents was 1× Phusion HF Buffer (Finnzymes), 200 µM dNTPs, 0.5 primers, 3% DMSO and 0.02 U/µL Phusion DNA polymerase (Finnzymes). The obtained PCR fragment was electrophoresed to confirm the desired length of the PCR product (1.9 kb) and was subsequently excised from the agarose gel and purified via standard techniques.

The purified PCR fragment was ligated into vector pGEM-T Easy (Promega) according to the product manual and transformed into *E. coli* XL-1 Blue using standard procedures. Recombinant bacteria were selected on LB plates supplemented with 100 mg/mL ampicillin. The presence of the valC gene in the recombinant *E. coli* clones was confirmed by colony PCR using M13(-20) (5'-TTGTAAAACGACGGCCAGTG-3', SEQ ID NO: 32) and SP6 Chip (5'-GTGACACTATAGAATACTCAAGC-3', SEQ ID NO: 33)) primers and standard protocols. The plasmid pGEM-valC was isolated using QIAprep Spin Miniprep Kit (Qiagen) and the sequence of valC was confirmed by DETT sequencing.

The plasmid pGEM-valC and the yeast expression vector pYES3/CT (Invitrogen) were digested with the restriction enzymes BamHI and NotI. The two required restriction fragments were subsequently excised from an agarose gel for purification. The fragments were then ligated and transformed into *E. coli* XL-1 Blue using standard procedures. By this cloning procedure the valC open reading frame was positioned between the GAL1 promoter that enables high level protein induction in yeast by galactose and the CYC1 terminator. No N- or C-terminal tags were added. Recombinant bacteria were selected on LB plates supplemented with 100 µg/mL ampicillin. The presence of the valC gene in the recombinant *E. coli* colonies was verified by colony PCR using vector primers and standard conditions. The plasmid was isolated using QIAprep Spin Miniprep Kit (Qiagen) and the nucleotide sequence of valC was confirmed by DETT sequencing.

The plasmid was then transformed into yeast strain WAT11 (Urban, P., Mignotte, C., Kazmaier, M., Delorme, F. and Pompon, D. 1997. J. Biol. Chem. 272: 19176-19186) using standard protocols (Gietz, R. D., Woods R. A. 2002. Methods in Enzymology 350: 87-96). The recombinant yeast colonies were selected on solid Synthetic dextrose minimal medium (0.67% Difco yeast nitrogen base medium without amino acids, 2% D-glucose, 40 mg/L adenine sulphate, 20 mg/L L-arginine, 100 mg/L L-aspartic acid, 100 mg/L L-glutamic acid, 20 mg/L L-histidine, 60 mg/L L-leucine, 30 mg/L L-lysine, 20 mg/L L-methionine, 50 mg/L L-phenylalanine, 375 mg/L L-serine, 200 mg/L L-threonine, 30 mg/L L-tyrosine, 150 mg/L L-valine, 20 mg/L uracil, 2% agar) omitting L-tryptophan for auxotrophic selection.

A single yeast colony containing valC was inoculated into 5 mL of liquid Synthetic galactose minimal medium (0.67% Difco yeast nitrogen base medium without amino acids, 2% D-galactose, 40 mg/L adenine sulphate, 20 mg/L L-arginine, 100 mg/L L-aspartic acid, 100 mg/L L-glutamic acid, 20 mg/L L-histidine, 60 mg/L L-leucine, 30 mg/L L-lysine, 20 mg/L L-methionine, 50 mg/L L-phenylalanine, 375 mg/L L-serine, 200 mg/L L-threonine, 30 mg/L L-tyrosine, 150 mg/L L-valine, 20 mg/L uracil) without L-tryptophan and the starter yeast culture was grown overnight at 30° C. Yeast cultures transformed with the empty pYES3/CT vector were used as controls in shake-flask fermentation experiments. After overnight incubation the optical density ($OD_{600}$) of the yeast cultures was measured. The cultures were subsequently diluted to $OD_{600}$ of 0.05 in 50 mL of Synthetic galactose minimal medium and incubated at 200 rpm and 30° C. The cultures were overlaid with 5 mL of n-dodecane when the $OD_{600}$ was in the range from 0.8 to 1, and cultivation was continued for 3 days. After three days of fermentation the n-dodecane layer was separated from the yeast cultures by a glass separation funnel and subsequently centrifuged at 1,200 rpm for 10 min, diluted 3-fold in ethyl acetate, dried using anhydrous $Na_2SO_4$ and then analyzed by GC-MS, which was operated as has been described in the "Valencene synthase activity test" in the general part of the experimental section.

(+)-Valencene was detected at a retention time of 14.051 and was identified by comparison of the spectra and retention time to the authentic standard of (+)-valencene. No compound was detected at this retention time in the yeast cultures transformed with the empty pYES3/CT vector. Germacrene A was formed as a minor side product in these yeast fermentations.

Quantification of the amount of (+)-valencene produced was conducted by determination of the total ion count (TIC) peak area of the (+)-valencene peaks from three independent shake-flask fermentation experiments. Absolute concentration of (+)-valencene was calculated from the peak area by comparison to a standard curve prepared by measuring the dilution series of authentic standards with a known concentration. The produced amount of (+)-valencene was 1.36±0.05 mg/L yeast culture. This example thus demonstrates the applicability of valC to produce (+)-valencene in yeast.

Example 10

Expression of ValC in Plants

The full length open reading frame encoding the valC was excised from plasmid pAC-65-3 using restriction enzymes BamHI and NotI. In parallel, cloning vector pImpactVector 1.5 (HyperText Transfer Protocol://worldwideweb.pri-.wur.nl/UK/products/ImpactVector) was also digested with restriction enzymes BamHI and NotI. Both the required pImpactVector 1.5 and the valC DNA restriction fragments were isolated from an agarose gel, followed by purification of the required DNA fragments, their subsequent ligation and finally transformation into E. coli XL-1 blue using standard procedures. Recombinant bacteria were selected on solid LB medium (1000 mL deionized water, with 10 g Bactotryptone, 5 g Bacto yeast, 5 g NaC1) with 1.5% technical agar, containing 20 µg/mL gentamycin for selection of transformants.

After overnight growth of recombinant colonies in liquid culture (3 mL LB broth with 20 µg/mL gentamycin, 250 rpm, 37° C.), plasmid DNA was isolated using the Qiaprep Spin Miniprep kit (Qiagen). Isolated plasmid material was tested by restriction analysis using the enzymes BamHI and NotI. Finally, the insert of a correct vector, which was named pIV5-ValC, was checked by DETT sequencing with vector primers. Within pIV5-ValC, the ValC DNA is preceeded by a CoxIV mitochondrial targeting sequence (Köhler RH, Zipfel WR, Webb WW, Hanson MR. Plant J. 1997;11:613-21), and positioned between the RbcS1 promotor (Prbcs) and RbcS1 terminator (Trbcs) from *Chrysanthemum morifolium*(HyperText Transfer Protocol://worldwideweb.pri.wur.nl/UK/products/ImpactVector); Outchkourov NS, Peters J, de Jong J, Rademakers W, Jongsma MA. Planta. 2003, 216(6):1003-12).

DNA from the plasmids pIV5-ValC and pBINPLUS (van Engelen F A, Molthoff J W, Conner A J, Nap J P, Pereira A, Stiekema W J. Transgenic Res. 1995 July; 4(4):288-90.) were both digested with AscI and PacI restriction enzymes in the prescribed buffers. Both the required pBINPLUS and valC DNA restriction fragments were isolated from an agarose gel, followed by purification of the required DNA fragments, their subsequent ligation and finally transformation into *E. coli* XL-1 blue using standard procedures. Recombinant bacteria were selected on LB plates containing 50 µg/mL kanamycin. After ON growth of recombinant colonies in liquid culture (3 mL LB broth with 50 µg/mL kanamycin, 250 rpm, 37° C.), plasmid DNA was isolated using the Qiaprep Spin Miniprep kit (Qiagen). Isolated plasmid material was tested by restriction analysis using the enzymes AscI and PacI. A plasmid with a correct insertion of the Prbcs, ValC and Trbcs cassette was called pBIN-ValC.

The pBin-ValC and control plasmid pBINPLUS were transformed to *Agrobacterium tumefaciens* LBA4404. Electro competent cells of *Agrobacterium* were prepared according to standard protocols, and 40 µl of competent cells were mixed with 1 µl of plasmid DNA. The mix was then transferred to a pre-cooled electroporation cuvette and kept on ice until electroporation. For electroporation, the The cuvette was placed in the electroporation holder and electroporated under standard conditions (100 ohm, 250 capacitance, 2.50 Kvolts and 25 cap). Immediately after the electroporation, 1 mL of SOC-medium was added, and the cells were incubated 60 minutes at 37° C. under gentle shaking. Thereafter, bacteria were plated on LB-agar plates with rifampicillin (100 µg/ml) and kanamycin (50 µg/ml). The presence of correct plasmid DNA in the transformed bacteria was confirmed by plasmid isolation, and restriction analysis using BamHI and NotI restriction enzymes.

For transformation of *Nicotiana benthamiana* plants, the *Agrobacterium tumefaciens* LBA4404 strains with pBinValC and control plasmid pBINPLUS were inoculated in a starter-culture 10 mL liquid LB broth with antibiotics with rifampicillin (100 mg/ml) and kanamycin (50 mg/ml) overnight at 28° C. and 250 rpm shaking. Subsequently, 0.25 mL of the startercultures were added to 25 ml liquid LB broth with rifampicillin (100 µg/ml) and kanamycin (50 mg/ml) and incubated overnight at 28° C. and 250 rpm shaking. The next day, the overnight culture was centrifuged for 10 minutes at 8000×g and the supernatant discarded. The pellet was resuspended in 20 mL M300 liquid medium (4.4 g/l Murachige & Skoog (MS) salts with vitamins, 0.5 g/l 2-(N-morpholino) ethanesulfonic acid (MES), 30 g/l sucrose, pH6.0) with acetosyringone (100 µM). All chemicals for preparing the media were from Duchefa. Cells were centrifuged again under the same conditions, the supernatant was discarded and the cells were again resuspended in 20 mL M300 medium with acetosyringone. The resuspension was diluted in 980 ml of M300 medium with acetosyringone.

On the same day, *Nicotiana benthamiana* plants that had been seeded on sterile MS-medium with 0.6% agar six weeks before and raised in a sterile environment (16 hour light per day, 25° C.) were cut into leaf discs (explants) of 5-7 mm, and explants were immediately put in M300 liquid medium to prevent drying. After all explants (120 per construct) were cut, the M300 medium was replaced by diluted *Agrobacterium* suspension in a petridish, and the petridish was sealed and incubated in the dark for three days at room temperature. Subsequently, the explants were washed in M300 medium with ticarcillin (500 mg/L) and laid on solid M300 with benzylaminopurine (1 mg/l), auxin (0.1 mg/L), ticarcillin (500 mg/L), kanamycin (50 µg/L) and microagar (0.6%). In this way, explants were maintained in a growth chamber (16 hour light per day, 25° C.) and transferred to fresh medium every 14 days. After callus-formation had occurred (after +/−4 weeks), calli were cut and transferred to solid M300 with benzylaminopurine (1 mg/l), ticarcillin (500 mg/l), kanamycin (50 µg/l) and microagar (0.6%). When shoots were formed (after 4 to 8 weeks), they were cut from the callus, and transferred to solid M300 with ticarcillin (500 mg/l), kanamycin (50 µg/l) and microagar (0.6%) to stimulate rooting. For each line, 12 rooted plants were transferred to soil and further raised in a greenhouse (16 h light at 28° C. and 8 hours darkness at 25° C.) until they had ±12 leaves. In this stage, experiments for determining production of valencene were started.

Three pBIN-ValC plants and three pBINPLUS plants were further analyzed. For each plant, three freshly cut *N. benthamiana* leaves of 0.4 to 1.0 g were weighed, and cut ends were placed in a 4-mL beaker covered with aluminum foil and containing 3 mL of water. Each beaker with a leaf was placed in a separate 0.5-liter sealed glass container. Leaves were then incubated at 21° C. in a light regime of 16 hours of light and 8 hours of darkness. A vacuum pump was used to draw air through the glass container at approximately 100 mL/min, with the incoming air being purified through steel sorbent cartridges (89 mm×6.4 mm O.D.; Markes) containing 200 mg Tenax TA 20/35. At the outlet, the volatiles emitted by the detached leaves were trapped on a similar cartridge. Volatiles were collected during 24 h. Outlet cartridges were eluted using 3 times 1 mL of pentane:diethyl ether (4:1). Non-concentrated samples were dehydrated using anhydrous $Na_2SO_4$, and analyzed by GC-MS using a gas chromatograph (5890 series II, Hewlett-Packard) equipped with a 30 m×0.25 mm, 0.25 mm film thickness column (5MS, Hewlett-Packard) and a mass-selective detector (model 5972A, Hewlett-Packard). For analysis, 1 µl was injected, and the column temperature was increased from 45° C. to 280° C. in 20 minutes. A range of valencene standard solutions in pentane:ethyl-ether (80:20 v/v) was injected for reference and quantification. Valencene was found to elute at 13.87 minutes, and was identified in the plant headspace by comparison to the mass spectrum and retention time of the standard. The amount of valencene emitted was quantified for each plant by averaging the emitted micrograms of valencene per g leaf per 24 hours. While the pBINPLUS plants did not emit any detectable valencene, the three pBIN-ValC plants emitted (+) valencene at 0.51, 0.63 or 0.48 µg valencene per g leaf per 24 hours, respectively. This demonstrated the ability of ValC to mediate valencene production in plants

The invention claimed is:

1. A nucleic acid comprising a nucleic acid sequence encoding a valencene synthase having at least 95% sequence identity to the amino acid sequence set forth in SEQ ID NO:2, wherein the nucleic acid sequence has at least 95% sequence identity to the nucleic acid sequence set forth in SEQ ID NO:19.

2. An expression vector comprising the nucleic acid according to claim 1.

3. A host cell, which may be an organism per se or part of a multi-cellular organism, said host cell comprising an expression vector according to claim 2, which host cell is selected from the group consisting of bacterial cells, fungal cells and plant cells.

4. The host cell according to claim 3, wherein the host cell is a bacterial cell selected from the group of gram negative bacteria.

5. A method for preparing valencene, said method comprising converting a farnesyl diphosphate to valencene in the presence of a valencene synthase comprising the amino acid sequence having at least 95% sequence identity to the amino acid sequence set forth in SEQ ID NO:2.

6. The method according to claim 5, wherein the valencene is prepared in a host cell, a plant or plant culture or a mushroom or mushroom culture expressing said valencene synthase.

7. A method for preparing nootkatone, wherein valencene prepared in the method according to claim 5 is converted into nootkatone, which conversion may comprise a regiospecific hydroxylation of valencene followed by oxidation thereby forming nootkatone.

8. The method according to claim 7, wherein the nootkatone is prepared in a host cell expressing at least one enzyme catalysing a reaction step for the conversion of valencene to nootkatone.

9. The host cell according to claim 4, wherein the host cell is a bacterial cell selected from the group consisting of *Rhodobacter*, *Paracoccus* and *Escherichia*.

10. The host cell according to claim 9, wherein the host cell is a bacterial cell selected from the group consisting of *Rhodobacter capsulatus*, *Rhodobacter sphaeroides*, *Paracoccus carotinifaciens*, *Paracoccus zeaxanthinifaciens* and *Escherichia coli*.

* * * * *

SEQUENCE LISTING

<160> NUMBER OF SEQ ID NOS: 35

<210> SEQ ID NO 1
<211> LENGTH: 1722
<212> TYPE: DNA
<213> ORGANISM: Callitropsis nootkatensis
<220> FEATURE:
<221> NAME/KEY: CDS
<222> LOCATION: (1)..(1722)

<400> SEQUENCE: 1

| | | | | | | | | | | | | | | | | |
|---|---|---|---|---|---|---|---|---|---|---|---|---|---|---|---|---|
| atg | ccc | gtg | aag | gac | gcc | ctt | cgt | cgg | act | gga | aat | cat | cat | cct | aac | 48 |
| Met | Pro | Val | Lys | Asp | Ala | Leu | Arg | Arg | Thr | Gly | Asn | His | His | Pro | Asn | |
| 1 | | | 5 | | | | | 10 | | | | | 15 | | | |
| ttg | tgg | act | gat | gat | ttc | ata | cag | tcc | ctc | aat | tct | cca | tat | tcg | gat | 96 |
| Leu | Trp | Thr | Asp | Asp | Phe | Ile | Gln | Ser | Leu | Asn | Ser | Pro | Tyr | Ser | Asp | |
| | | | 20 | | | | 25 | | | | | 30 | | | | |
| tct | tca | tac | cat | aaa | cat | agg | gaa | ata | cta | att | gat | gag | att | cgt | gat | 144 |
| Ser | Ser | Tyr | His | Lys | His | Arg | Glu | Ile | Leu | Ile | Asp | Glu | Ile | Arg | Asp | |
| | | 35 | | | | 40 | | | | | 45 | | | | | |
| atg | ttt | tct | aat | gga | gaa | ggc | gat | gag | ttc | ggt | gta | ctt | gaa | aat | att | 192 |
| Met | Phe | Ser | Asn | Gly | Glu | Gly | Asp | Glu | Phe | Gly | Val | Leu | Glu | Asn | Ile | |
| | 50 | | | | | 55 | | | | | 60 | | | | | |
| tgg | ttt | gtt | gat | gtt | gta | caa | cgt | ttg | gga | ata | gat | cga | cat | ttt | caa | 240 |
| Trp | Phe | Val | Asp | Val | Val | Gln | Arg | Leu | Gly | Ile | Asp | Arg | His | Phe | Gln | |
| 65 | | | | | 70 | | | | | 75 | | | | | 80 | |
| gag | gaa | atc | aaa | act | gca | ctt | gat | tat | atc | tac | aag | ttc | tgg | aat | cat | 288 |
| Glu | Glu | Ile | Lys | Thr | Ala | Leu | Asp | Tyr | Ile | Tyr | Lys | Phe | Trp | Asn | His | |
| | | | | 85 | | | | | 90 | | | | | 95 | | |
| gat | agt | att | ttt | ggc | gat | ctc | aac | atg | gtg | gct | cta | gga | ttt | cgg | ata | 336 |
| Asp | Ser | Ile | Phe | Gly | Asp | Leu | Asn | Met | Val | Ala | Leu | Gly | Phe | Arg | Ile | |
| | | | 100 | | | | | 105 | | | | | 110 | | | |
| cta | cga | ctg | aat | aga | tat | gtc | gct | tct | tca | gat | gtt | ttt | aaa | aag | ttc | 384 |
| Leu | Arg | Leu | Asn | Arg | Tyr | Val | Ala | Ser | Ser | Asp | Val | Phe | Lys | Lys | Phe | |
| | | 115 | | | | | 120 | | | | | 125 | | | | |
| aaa | ggt | gaa | gaa | gga | caa | ttc | tct | ggt | ttt | gaa | tct | agc | gat | caa | gat | 432 |
| Lys | Gly | Glu | Glu | Gly | Gln | Phe | Ser | Gly | Phe | Glu | Ser | Ser | Asp | Gln | Asp | |
| | 130 | | | | | 135 | | | | | 140 | | | | | |
| gca | aaa | tta | gaa | atg | atg | tta | aat | tta | tat | aaa | gct | tca | gaa | tta | gat | 480 |
| Ala | Lys | Leu | Glu | Met | Met | Leu | Asn | Leu | Tyr | Lys | Ala | Ser | Glu | Leu | Asp | |
| 145 | | | | | 150 | | | | | 155 | | | | | 160 | |
| ttt | cct | gat | gaa | gat | atc | tta | aaa | gaa | gca | aga | gcg | ttt | gct | tct | atg | 528 |
| Phe | Pro | Asp | Glu | Asp | Ile | Leu | Lys | Glu | Ala | Arg | Ala | Phe | Ala | Ser | Met | |
| | | | | 165 | | | | | 170 | | | | | 175 | | |
| tac | ctg | aaa | cat | gtt | atc | aaa | gaa | tat | ggt | gac | ata | caa | gaa | tca | aaa | 576 |
| Tyr | Leu | Lys | His | Val | Ile | Lys | Glu | Tyr | Gly | Asp | Ile | Gln | Glu | Ser | Lys | |
| | | | 180 | | | | | 185 | | | | | 190 | | | |
| aat | cca | ctt | cta | atg | gag | ata | gag | tac | act | ttt | aaa | tat | cct | tgg | aga | 624 |
| Asn | Pro | Leu | Leu | Met | Glu | Ile | Glu | Tyr | Thr | Phe | Lys | Tyr | Pro | Trp | Arg | |
| | | 195 | | | | | 200 | | | | | 205 | | | | |
| tgt | agg | ctt | cca | agg | ttg | gag | gct | tgg | aac | ttt | att | cat | ata | atg | aga | 672 |
| Cys | Arg | Leu | Pro | Arg | Leu | Glu | Ala | Trp | Asn | Phe | Ile | His | Ile | Met | Arg | |
| | 210 | | | | | 215 | | | | | 220 | | | | | |
| caa | caa | gat | tgc | aat | ata | tca | ctt | gcc | aat | aac | ctt | tat | aaa | att | cca | 720 |
| Gln | Gln | Asp | Cys | Asn | Ile | Ser | Leu | Ala | Asn | Asn | Leu | Tyr | Lys | Ile | Pro | |
| 225 | | | | | 230 | | | | | 235 | | | | | 240 | |
| aaa | ata | tat | atg | aaa | aag | ata | ttg | gaa | cta | gca | ata | ctg | gac | ttc | aat | 768 |
| Lys | Ile | Tyr | Met | Lys | Lys | Ile | Leu | Glu | Leu | Ala | Ile | Leu | Asp | Phe | Asn | |
| | | | | 245 | | | | | 250 | | | | | 255 | | |
| att | ttg | cag | tca | caa | cat | caa | cat | gaa | atg | aaa | tta | ata | tcc | aca | tgg | 816 |
| Ile | Leu | Gln | Ser | Gln | His | Gln | His | Glu | Met | Lys | Leu | Ile | Ser | Thr | Trp | |

```
                  260             265             270
tgg aaa aat tca agt gca att caa ttg gat ttc ttt cgg cat cgt cac      864
Trp Lys Asn Ser Ser Ala Ile Gln Leu Asp Phe Phe Arg His Arg His
        275                 280                 285 ata gaa agt tat ttt tgg tgg gct agt cca tta ttt gaa cct gag ttc      912
Ile Glu Ser Tyr Phe Trp Trp Ala Ser Pro Leu Phe Glu Pro Glu Phe
    290                 295                 300 agt aca tgt aga att aat tgt acc aaa tta tct aca aaa atg ttc ctc      960
Ser Thr Cys Arg Ile Asn Cys Thr Lys Leu Ser Thr Lys Met Phe Leu
305                 310                 315                 320 ctt gac gat att tat gac aca tat ggg act gtt gag gaa ttg aaa cca     1008
Leu Asp Asp Ile Tyr Asp Thr Tyr Gly Thr Val Glu Glu Leu Lys Pro
                325                 330                 335 ttc aca aca aca tta aca aga tgg gat gtt tcc aca gtt gat aat cat     1056
Phe Thr Thr Thr Leu Thr Arg Trp Asp Val Ser Thr Val Asp Asn His
            340                 345                 350 cca gac tac atg aaa att gct ttc aat ttt tca tat gag ata tat aag     1104
Pro Asp Tyr Met Lys Ile Ala Phe Asn Phe Ser Tyr Glu Ile Tyr Lys
        355                 360                 365 gaa att gca agt gaa gcc gaa aga aag cat ggt ccc ttt gtt tac aaa     1152
Glu Ile Ala Ser Glu Ala Glu Arg Lys His Gly Pro Phe Val Tyr Lys
    370                 375                 380 tac ctt caa tct tgc tgg aag agt tat atc gag gct tat atg caa gaa     1200
Tyr Leu Gln Ser Cys Trp Lys Ser Tyr Ile Glu Ala Tyr Met Gln Glu
385                 390                 395                 400 gca gaa tgg ata gct tct aat cat ata cca ggt ttt gat gaa tac ttg     1248
Ala Glu Trp Ile Ala Ser Asn His Ile Pro Gly Phe Asp Glu Tyr Leu
                405                 410                 415 atg aat gga gta aaa agt agc ggc atg cga att cta atg ata cat gca     1296
Met Asn Gly Val Lys Ser Ser Gly Met Arg Ile Leu Met Ile His Ala
            420                 425                 430 cta ata cta atg gat act cct tta tct gat gaa att ttg gag caa ctt     1344
Leu Ile Leu Met Asp Thr Pro Leu Ser Asp Glu Ile Leu Glu Gln Leu
        435                 440                 445 gat atc cca tca tcc aag tcg caa gct ctt cta tca tta att act cga     1392
Asp Ile Pro Ser Ser Lys Ser Gln Ala Leu Leu Ser Leu Ile Thr Arg
    450                 455                 460 cta gtg gat gat gtc aaa gac ttt gag gat gaa caa gct cat ggg gag     1440
Leu Val Asp Asp Val Lys Asp Phe Glu Asp Glu Gln Ala His Gly Glu
465                 470                 475                 480 atg gca tca agt ata gag tgc tac atg aaa gac aac cat ggt tct aca     1488
Met Ala Ser Ser Ile Glu Cys Tyr Met Lys Asp Asn His Gly Ser Thr
                485                 490                 495 agg gaa gat gct ttg aat tat ctc aaa att cgt ata gag agt tgt gtg     1536
Arg Glu Asp Ala Leu Asn Tyr Leu Lys Ile Arg Ile Glu Ser Cys Val
            500                 505                 510 caa gag tta aat aag gag ctt ctc gag cct tca aat atg cat gga tct     1584
Gln Glu Leu Asn Lys Glu Leu Leu Glu Pro Ser Asn Met His Gly Ser
        515                 520                 525 ttt aga aac cta tat ctc aat gtt ggc atg cga gta ata ttt ttt atg     1632
Phe Arg Asn Leu Tyr Leu Asn Val Gly Met Arg Val Ile Phe Phe Met
    530                 535                 540 ctc aat gat ggt gat ctc ttt aca cac tcc aat aga aaa gag ata caa     1680
Leu Asn Asp Gly Asp Leu Phe Thr His Ser Asn Arg Lys Glu Ile Gln
545                 550                 555                 560 gat gca ata aca aaa ttt ttt gtg gaa cca atc att cca tag              1722
Asp Ala Ile Thr Lys Phe Phe Val Glu Pro Ile Ile Pro
                565                 570
```

<210> SEQ ID NO 2
<211> LENGTH: 573
<212> TYPE: PRT
<213> ORGANISM: Callitropsis nootkatensis

<400> SEQUENCE: 2

```
Met Pro Val Lys Asp Ala Leu Arg Arg Thr Gly Asn His His Pro Asn
1               5                   10                  15

Leu Trp Thr Asp Asp Phe Ile Gln Ser Leu Asn Ser Pro Tyr Ser Asp
            20                  25                  30

Ser Ser Tyr His Lys His Arg Glu Ile Leu Ile Asp Glu Ile Arg Asp
        35                  40                  45

Met Phe Ser Asn Gly Glu Gly Asp Glu Phe Gly Val Leu Glu Asn Ile
    50                  55                  60

Trp Phe Val Asp Val Val Gln Arg Leu Gly Ile Asp Arg His Phe Gln
65                  70                  75                  80

Glu Glu Ile Lys Thr Ala Leu Asp Tyr Ile Tyr Lys Phe Trp Asn His
                85                  90                  95

Asp Ser Ile Phe Gly Asp Leu Asn Met Val Ala Leu Gly Phe Arg Ile
            100                 105                 110

Leu Arg Leu Asn Arg Tyr Val Ala Ser Ser Asp Val Phe Lys Lys Phe
        115                 120                 125

Lys Gly Glu Glu Gly Gln Phe Ser Gly Phe Glu Ser Ser Asp Gln Asp
130                 135                 140

Ala Lys Leu Glu Met Met Leu Asn Leu Tyr Lys Ala Ser Glu Leu Asp
145                 150                 155                 160

Phe Pro Asp Glu Asp Ile Leu Lys Glu Ala Arg Ala Phe Ala Ser Met
                165                 170                 175

Tyr Leu Lys His Val Ile Lys Glu Tyr Gly Asp Ile Gln Glu Ser Lys
            180                 185                 190

Asn Pro Leu Leu Met Glu Ile Glu Tyr Thr Phe Lys Tyr Pro Trp Arg
        195                 200                 205

Cys Arg Leu Pro Arg Leu Glu Ala Trp Asn Phe Ile His Ile Met Arg
210                 215                 220

Gln Gln Asp Cys Asn Ile Ser Leu Ala Asn Asn Leu Tyr Lys Ile Pro
225                 230                 235                 240

Lys Ile Tyr Met Lys Lys Ile Leu Glu Leu Ala Ile Leu Asp Phe Asn
                245                 250                 255

Ile Leu Gln Ser Gln His Gln His Glu Met Lys Leu Ile Ser Thr Trp
            260                 265                 270

Trp Lys Asn Ser Ser Ala Ile Gln Leu Asp Phe Phe Arg His Arg His
        275                 280                 285

Ile Glu Ser Tyr Phe Trp Trp Ala Ser Pro Leu Phe Glu Pro Glu Phe
    290                 295                 300

Ser Thr Cys Arg Ile Asn Cys Thr Lys Leu Ser Thr Lys Met Phe Leu
305                 310                 315                 320

Leu Asp Asp Ile Tyr Asp Thr Tyr Gly Thr Val Glu Glu Leu Lys Pro
                325                 330                 335

Phe Thr Thr Thr Leu Thr Arg Trp Asp Val Ser Thr Val Asp Asn His
            340                 345                 350

Pro Asp Tyr Met Lys Ile Ala Phe Asn Phe Ser Tyr Glu Ile Tyr Lys
        355                 360                 365

Glu Ile Ala Ser Glu Ala Glu Arg Lys His Gly Pro Phe Val Tyr Lys
    370                 375                 380
```

```
Tyr Leu Gln Ser Cys Trp Lys Ser Tyr Ile Glu Ala Tyr Met Gln Glu
385                 390                 395                 400

Ala Glu Trp Ile Ala Ser Asn His Ile Pro Gly Phe Asp Glu Tyr Leu
            405                 410                 415

Met Asn Gly Val Lys Ser Ser Gly Met Arg Ile Leu Met Ile His Ala
        420                 425                 430

Leu Ile Leu Met Asp Thr Pro Leu Ser Asp Glu Ile Leu Glu Gln Leu
    435                 440                 445

Asp Ile Pro Ser Ser Lys Ser Gln Ala Leu Leu Ser Leu Ile Thr Arg
450                 455                 460

Leu Val Asp Asp Val Lys Asp Phe Glu Asp Gln Ala His Gly Glu
465                 470                 475                 480

Met Ala Ser Ser Ile Glu Cys Tyr Met Lys Asp Asn His Gly Ser Thr
        485                 490                 495

Arg Glu Asp Ala Leu Asn Tyr Leu Lys Ile Arg Ile Glu Ser Cys Val
            500                 505                 510

Gln Glu Leu Asn Lys Glu Leu Leu Glu Pro Ser Asn Met His Gly Ser
        515                 520                 525

Phe Arg Asn Leu Tyr Leu Asn Val Gly Met Arg Val Ile Phe Phe Met
    530                 535                 540

Leu Asn Asp Gly Asp Leu Phe Thr His Ser Asn Arg Lys Glu Ile Gln
545                 550                 555                 560

Asp Ala Ile Thr Lys Phe Phe Val Glu Pro Ile Ile Pro
                565                 570
```

```
<210> SEQ ID NO 3
<211> LENGTH: 1770
<212> TYPE: DNA
<213> ORGANISM: Callitropsis nootkatensis
<220> FEATURE:
<221> NAME/KEY: CDS
<222> LOCATION: (1)..(1770)

<400> SEQUENCE: 3 atg gct gaa atg ttt aat gga aat tcc agc aat gat gga agt tct tgc      48
Met Ala Glu Met Phe Asn Gly Asn Ser Ser Asn Asp Gly Ser Ser Cys
1               5                   10                  15 atg ccc gtg aag gac gcc ctt cgt cgg act gga aat cat cat cct aac      96
Met Pro Val Lys Asp Ala Leu Arg Arg Thr Gly Asn His His Pro Asn
            20                  25                  30 ttg tgg act gat gat ttc ata cag tcc ctc aat tct cca tat tcg gat     144
Leu Trp Thr Asp Asp Phe Ile Gln Ser Leu Asn Ser Pro Tyr Ser Asp
        35                  40                  45 tct tca tac cat aaa cat agg gaa ata cta att gat gag att cgt gat     192
Ser Ser Tyr His Lys His Arg Glu Ile Leu Ile Asp Glu Ile Arg Asp
    50                  55                  60 atg ttt tct aat gga gaa ggc gat gag ttc ggt gta ctt gaa aat att     240
Met Phe Ser Asn Gly Glu Gly Asp Glu Phe Gly Val Leu Glu Asn Ile
65                  70                  75                  80 tgg ttt gtt gat gtt gta caa cgt ttg gga ata gat cga cat ttt caa     288
Trp Phe Val Asp Val Val Gln Arg Leu Gly Ile Asp Arg His Phe Gln
                85                  90                  95 gag gaa atc aaa act gca ctt gat tat atc tac aag ttc tgg aat cat     336
Glu Glu Ile Lys Thr Ala Leu Asp Tyr Ile Tyr Lys Phe Trp Asn His
            100                 105                 110 gat agt att ttt ggc gat ctc aac atg gtg gct cta gga ttt cgg ata     384
Asp Ser Ile Phe Gly Asp Leu Asn Met Val Ala Leu Gly Phe Arg Ile
        115                 120                 125
```

-continued

```
cta cga ctg aat aga tat gtc gct tct tca gat gtt ttt aaa aag ttc      432
Leu Arg Leu Asn Arg Tyr Val Ala Ser Ser Asp Val Phe Lys Lys Phe
        130                 135                 140 aaa ggt gaa gaa gga caa ttc tct ggt ttt gaa tct agc gat caa gat      480
Lys Gly Glu Glu Gly Gln Phe Ser Gly Phe Glu Ser Ser Asp Gln Asp
145                 150                 155                 160 gca aaa tta gaa atg atg tta aat tta tat aaa gct tca gaa tta gat      528
Ala Lys Leu Glu Met Met Leu Asn Leu Tyr Lys Ala Ser Glu Leu Asp
                165                 170                 175 ttt cct gat gaa gat atc tta aaa gaa gca aga gcg ttt gct tct atg      576
Phe Pro Asp Glu Asp Ile Leu Lys Glu Ala Arg Ala Phe Ala Ser Met
            180                 185                 190 tac ctg aaa cat gtt atc aaa gaa tat ggt gac ata caa gaa tca aaa      624
Tyr Leu Lys His Val Ile Lys Glu Tyr Gly Asp Ile Gln Glu Ser Lys
        195                 200                 205 aat cca ctt cta atg gag ata gag tac act ttt aaa tat cct tgg aga      672
Asn Pro Leu Leu Met Glu Ile Glu Tyr Thr Phe Lys Tyr Pro Trp Arg
210                 215                 220 tgt agg ctt cca agg ttg gag gct tgg aac ttt att cat ata atg aga      720
Cys Arg Leu Pro Arg Leu Glu Ala Trp Asn Phe Ile His Ile Met Arg
225                 230                 235                 240 caa caa gat tgc aat ata tca ctt gcc aat aac ctt tat aaa att cca      768
Gln Gln Asp Cys Asn Ile Ser Leu Ala Asn Asn Leu Tyr Lys Ile Pro
                245                 250                 255 aaa ata tat atg aaa aag ata ttg gaa cta gca ata ctg gac ttc aat      816
Lys Ile Tyr Met Lys Lys Ile Leu Glu Leu Ala Ile Leu Asp Phe Asn
            260                 265                 270 att ttg cag tca caa cat caa cat gaa atg aaa tta ata tcc aca tgg      864
Ile Leu Gln Ser Gln His Gln His Glu Met Lys Leu Ile Ser Thr Trp
        275                 280                 285 tgg aaa aat tca agt gca att caa ttg gat ttc ttt cgg cat cgt cac      912
Trp Lys Asn Ser Ser Ala Ile Gln Leu Asp Phe Phe Arg His Arg His
290                 295                 300 ata gaa agt tat ttt tgg tgg gct agt cca tta ttt gaa cct gag ttc      960
Ile Glu Ser Tyr Phe Trp Trp Ala Ser Pro Leu Phe Glu Pro Glu Phe
305                 310                 315                 320 agt aca tgt aga att aat tgt acc aaa tta tct aca aaa atg ttc ctc     1008
Ser Thr Cys Arg Ile Asn Cys Thr Lys Leu Ser Thr Lys Met Phe Leu
                325                 330                 335 ctt gac gat att tat gac aca tat ggg act gtt gag gaa ttg aaa cca     1056
Leu Asp Asp Ile Tyr Asp Thr Tyr Gly Thr Val Glu Glu Leu Lys Pro
            340                 345                 350 ttc aca aca aca tta aca aga tgg gat gtt tcc aca gtt gat aat cat     1104
Phe Thr Thr Thr Leu Thr Arg Trp Asp Val Ser Thr Val Asp Asn His
        355                 360                 365 cca gac tac atg aaa att gct ttc aat ttt tca tat gag ata tat aag     1152
Pro Asp Tyr Met Lys Ile Ala Phe Asn Phe Ser Tyr Glu Ile Tyr Lys
370                 375                 380 gaa att gca agt gaa gcc gaa aga aag cat ggt ccc ttt gtt tac aaa     1200
Glu Ile Ala Ser Glu Ala Glu Arg Lys His Gly Pro Phe Val Tyr Lys
385                 390                 395                 400 tac ctt caa tct tgc tgg aag agt tat atc gag gct tat atg caa gaa     1248
Tyr Leu Gln Ser Cys Trp Lys Ser Tyr Ile Glu Ala Tyr Met Gln Glu
                405                 410                 415 gca gaa tgg ata gct tct aat cat ata cca ggt ttt gat gaa tac ttg     1296
Ala Glu Trp Ile Ala Ser Asn His Ile Pro Gly Phe Asp Glu Tyr Leu
            420                 425                 430 atg aat gga gta aaa agt agc ggc atg cga att cta atg ata cat gca     1344
Met Asn Gly Val Lys Ser Ser Gly Met Arg Ile Leu Met Ile His Ala
        435                 440                 445
```

```
cta ata cta atg gat act cct tta tct gat gaa att ttg gag caa ctt      1392
Leu Ile Leu Met Asp Thr Pro Leu Ser Asp Glu Ile Leu Glu Gln Leu
    450                 455                 460 gat atc cca tca tcc aag tcg caa gct ctt cta tca tta att act cga      1440
Asp Ile Pro Ser Ser Lys Ser Gln Ala Leu Leu Ser Leu Ile Thr Arg
465                 470                 475                 480 cta gtg gat gat gtc aaa gac ttt gag gat gaa caa gct cat ggg gag      1488
Leu Val Asp Asp Val Lys Asp Phe Glu Asp Glu Gln Ala His Gly Glu
                485                 490                 495 atg gca tca agt ata gag tgc tac atg aaa gac aac cat ggt tct aca      1536
Met Ala Ser Ser Ile Glu Cys Tyr Met Lys Asp Asn His Gly Ser Thr
            500                 505                 510 agg gaa gat gct ttg aat tat ctc aaa att cgt ata gag agt tgt gtg      1584
Arg Glu Asp Ala Leu Asn Tyr Leu Lys Ile Arg Ile Glu Ser Cys Val
        515                 520                 525 caa gag tta aat aag gag ctt ctc gag cct tca aat atg cat gga tct      1632
Gln Glu Leu Asn Lys Glu Leu Leu Glu Pro Ser Asn Met His Gly Ser
    530                 535                 540 ttt aga aac cta tat ctc aat gtt ggc atg cga gta ata ttt ttt atg      1680
Phe Arg Asn Leu Tyr Leu Asn Val Gly Met Arg Val Ile Phe Phe Met
545                 550                 555                 560 ctc aat gat ggt gat ctc ttt aca cac tcc aat aga aaa gag ata caa      1728
Leu Asn Asp Gly Asp Leu Phe Thr His Ser Asn Arg Lys Glu Ile Gln
                565                 570                 575 gat gca ata aca aaa ttt ttt gtg gaa cca atc att cca tag              1770
Asp Ala Ile Thr Lys Phe Phe Val Glu Pro Ile Ile Pro
            580                 585

<210> SEQ ID NO 4
<211> LENGTH: 589
<212> TYPE: PRT
<213> ORGANISM: Callitropsis nootkatensis

<400> SEQUENCE: 4

Met Ala Glu Met Phe Asn Gly Asn Ser Ser Asn Asp Gly Ser Ser Cys
1               5                   10                  15

Met Pro Val Lys Asp Ala Leu Arg Arg Thr Gly Asn His His Pro Asn
            20                  25                  30

Leu Trp Thr Asp Asp Phe Ile Gln Ser Leu Asn Ser Pro Tyr Ser Asp
        35                  40                  45

Ser Ser Tyr His Lys His Arg Glu Ile Leu Ile Asp Glu Ile Arg Asp
    50                  55                  60

Met Phe Ser Asn Gly Glu Gly Asp Glu Phe Gly Val Leu Glu Asn Ile
65                  70                  75                  80

Trp Phe Val Asp Val Val Gln Arg Leu Gly Ile Asp Arg His Phe Gln
                85                  90                  95

Glu Glu Ile Lys Thr Ala Leu Asp Tyr Ile Tyr Lys Phe Trp Asn His
            100                 105                 110

Asp Ser Ile Phe Gly Asp Leu Asn Met Val Ala Leu Gly Phe Arg Ile
        115                 120                 125

Leu Arg Leu Asn Arg Tyr Val Ala Ser Asp Val Phe Lys Lys Phe
    130                 135                 140

Lys Gly Glu Glu Gly Gln Phe Ser Gly Phe Glu Ser Ser Asp Gln Asp
145                 150                 155                 160

Ala Lys Leu Glu Met Met Leu Asn Leu Tyr Lys Ala Ser Glu Leu Asp
                165                 170                 175

Phe Pro Asp Glu Asp Ile Leu Lys Glu Ala Arg Ala Phe Ala Ser Met
```

```
            180             185             190
Tyr Leu Lys His Val Ile Lys Glu Tyr Gly Asp Ile Gln Glu Ser Lys
            195                 200                 205
Asn Pro Leu Leu Met Glu Ile Glu Tyr Thr Phe Lys Tyr Pro Trp Arg
        210                 215                 220
Cys Arg Leu Pro Arg Leu Glu Ala Trp Asn Phe Ile His Ile Met Arg
225                 230                 235                 240
Gln Gln Asp Cys Asn Ile Ser Leu Ala Asn Asn Leu Tyr Lys Ile Pro
                245                 250                 255
Lys Ile Tyr Met Lys Lys Ile Leu Glu Leu Ala Ile Leu Asp Phe Asn
            260                 265                 270
Ile Leu Gln Ser Gln His Gln His Glu Met Lys Leu Ile Ser Thr Trp
        275                 280                 285
Trp Lys Asn Ser Ser Ala Ile Gln Leu Asp Phe Arg His Arg His
290                 295                 300
Ile Glu Ser Tyr Phe Trp Trp Ala Ser Pro Leu Phe Glu Pro Glu Phe
305                 310                 315                 320
Ser Thr Cys Arg Ile Asn Cys Thr Lys Leu Ser Thr Lys Met Phe Leu
                325                 330                 335
Leu Asp Asp Ile Tyr Asp Thr Tyr Gly Thr Val Glu Glu Leu Lys Pro
            340                 345                 350
Phe Thr Thr Thr Leu Thr Arg Trp Asp Val Ser Thr Val Asp Asn His
        355                 360                 365
Pro Asp Tyr Met Lys Ile Ala Phe Asn Phe Ser Tyr Glu Ile Tyr Lys
370                 375                 380
Glu Ile Ala Ser Glu Ala Glu Arg Lys His Gly Pro Phe Val Tyr Lys
385                 390                 395                 400
Tyr Leu Gln Ser Cys Trp Lys Ser Tyr Ile Glu Ala Tyr Met Gln Glu
                405                 410                 415
Ala Glu Trp Ile Ala Ser Asn His Ile Pro Gly Phe Asp Glu Tyr Leu
            420                 425                 430
Met Asn Gly Val Lys Ser Ser Gly Met Arg Ile Leu Met Ile His Ala
        435                 440                 445
Leu Ile Leu Met Asp Thr Pro Leu Ser Asp Glu Ile Leu Glu Gln Leu
450                 455                 460
Asp Ile Pro Ser Ser Lys Ser Gln Ala Leu Leu Ser Leu Ile Thr Arg
465                 470                 475                 480
Leu Val Asp Asp Val Lys Asp Phe Glu Asp Glu Gln Ala His Gly Glu
                485                 490                 495
Met Ala Ser Ser Ile Glu Cys Tyr Met Lys Asp Asn His Gly Ser Thr
            500                 505                 510
Arg Glu Asp Ala Leu Asn Tyr Leu Lys Ile Arg Ile Glu Ser Cys Val
        515                 520                 525
Gln Glu Leu Asn Lys Glu Leu Leu Glu Pro Ser Asn Met His Gly Ser
530                 535                 540
Phe Arg Asn Leu Tyr Leu Asn Val Gly Met Arg Val Ile Phe Phe Met
545                 550                 555                 560
Leu Asn Asp Gly Asp Leu Phe Thr His Ser Asn Arg Lys Glu Ile Gln
                565                 570                 575
Asp Ala Ile Thr Lys Phe Phe Val Glu Pro Ile Ile Pro
            580                 585

<210> SEQ ID NO 5
```

```
<211> LENGTH: 39
<212> TYPE: DNA
<213> ORGANISM: Artificial
<220> FEATURE:
<223> OTHER INFORMATION: primer

<400> SEQUENCE: 5
atataggatc cggctgaaat gtttaatgga aattccagc                              39

<210> SEQ ID NO 6
<211> LENGTH: 40
<212> TYPE: DNA
<213> ORGANISM: Artificial
<220> FEATURE:
<223> OTHER INFORMATION: primer

<400> SEQUENCE: 6
atatactgca gctctggatc tatggaatga ttggttccac                             40

<210> SEQ ID NO 7
<211> LENGTH: 1650
<212> TYPE: DNA
<213> ORGANISM: Artificial
<220> FEATURE:
<223> OTHER INFORMATION: codon optimized ValF gene

<400> SEQUENCE: 7
atgtcgagcg cgagaccttt ccgccccacg gccgacttcc atccgtccct ctggcggaac       60
cacttcctca agggggcctc cgatttcaag accgtggacc atacggcgac gcaggaacgg      120
cacgaggccc tcaaggagga ggtccgccgc atgatcaccg acgccgaaga caagccggtc      180
cagaagctcc gcctgatcga cgaggtccag cgcctgggcg tggcgtatca tttcgagaaa      240
gaaatcgagg atgcgatcca gaagctctgc ccgatctata tcgatagcaa tcgcgccgat      300
ctccataccg tgtcgctgca cttccgcctg ctgcggcagc agggcatcaa gatcagctgc      360
gacgtgttcg aaaagttcaa ggacgacgag ggccgcttca gtcgtcgcct gatcaacgac      420
gtgcagggca tgctgtcgct gtacgaggcc gcgtacatgg ccgtgcgcgg cgagcatatc      480
ctggacgaag ccatcgcgtt cacgaccacg catctgaagt cgctggtggc gcaggaccac      540
gtgacgccga agctcgccga gcagatcaac cacgcgctgt atcgccgcct ccgcaagacc      600
ctcccgcgcc tcgaggcccg ctatttcatg agcatgatca actcgacctc ggatcacctg      660
tacaataaga ccctgctcaa cttcgcgaaa ctggacttca atatcctcct cgagctgcac      720
aaggaggagc tcaacgagct gaccaagtgg tggaaggatc tggacttcac caccaagctg      780
ccgtacgccc gcgatcgcct cgtggagctg tatttctggg acctgggcac ctacttcgaa      840
ccccagtacg ccttcgggcg gaagatcatg acccagctca attatatcct cagcatcatc      900
gacgacacct atgacgcgta cggcacgctg gaggagctgt ccctgttcac ggaagccgtc      960
cagcggtgga acatcgaggc cgtcgacatg ctccccgagt acatgaaact gatctaccgg     1020
accctgctgg atgccttcaa cgagatcgag gaggacatgc gaaacaggg ccggtcccac     1080 tgcgtgcgct acgcgaagga agagaaccag aaggtcatcg gcgcctactc ggtccaggcg     1140
aagtggttca gcgagggcta tgtgccgacg atcgaggaat atatgccgat cgcgctcacc     1200
tcgtgcgcgt acacgttcgt gatcaccaat tcgttcctcg gcatgggcga tttcgcgacc     1260
aaggaggtct tcgagtggat cagcaacaat ccgaaggtgg tgaaggcggc ctcggtcatc     1320
tgccggctca tggatgacat gcaggggcat gagttcgaac agaagcgcgg ccacgtcgcg     1380
tccgccatcg agtgctatac caagcagcat ggcgtgtcga aggaggaggc catcaagatg     1440
```

```
ttcgaggagg aagtcgccaa cgcgtggaag gacatcaatg aggagctgat gatgaagccc    1500
accgtcgtgg cccgcccct gctgggcacc atcctgaacc tcgcccgcgc catcgacttc    1560
atctacaagg aggacgatgg gtatacgcat tcctatctga tcaaggacca gatcgcctcg    1620
gtcctcggcg atcatgtccc gttctgataa                                    1650
```

<210> SEQ ID NO 8
<211> LENGTH: 1656
<212> TYPE: DNA
<213> ORGANISM: Artificial
<220> FEATURE:
<223> OTHER INFORMATION: codon optimized ValFpoR
<220> FEATURE:
<221> NAME/KEY: CDS
<222> LOCATION: (1)..(1656)

<400> SEQUENCE: 8

```
atg agc tcg ggc gag acc ttc cgc ccg acc gcc gat ttc cat ccc tcg      48
Met Ser Ser Gly Glu Thr Phe Arg Pro Thr Ala Asp Phe His Pro Ser
1               5                   10                  15 ctc tgg cgc aac cat ttc ctg aag ggc gcc tcc gac ttc aag acc gtc      96
Leu Trp Arg Asn His Phe Leu Lys Gly Ala Ser Asp Phe Lys Thr Val
            20                  25                  30 gat cac acg gcc acc cag gag cgc cac gag gcg ctg aag gaa gag gtg     144
Asp His Thr Ala Thr Gln Glu Arg His Glu Ala Leu Lys Glu Glu Val
        35                  40                  45 cgc cgg atg atc acc gac gcc gag gac aag ccg gtg cag aag ctg cgg     192
Arg Arg Met Ile Thr Asp Ala Glu Asp Lys Pro Val Gln Lys Leu Arg
    50                  55                  60 ctg atc gac gag gtg cag cgt ctc ggc gtg gcc tat cac ttc gag aag     240
Leu Ile Asp Glu Val Gln Arg Leu Gly Val Ala Tyr His Phe Glu Lys
65                  70                  75                  80 gag atc gag gat gcg atc cag aag ctc tgc ccg atc tac atc gac agc     288
Glu Ile Glu Asp Ala Ile Gln Lys Leu Cys Pro Ile Tyr Ile Asp Ser
                85                  90                  95 aac cgc gcc gat ctg cac acg gtc tcg ctg cat ttc cgg ctg ctg cgc     336
Asn Arg Ala Asp Leu His Thr Val Ser Leu His Phe Arg Leu Leu Arg
            100                 105                 110 cag cag ggc atc aag atc tcc tgc gac gtc ttc gag aag ttc aag gac     384
Gln Gln Gly Ile Lys Ile Ser Cys Asp Val Phe Glu Lys Phe Lys Asp
        115                 120                 125 gac gag ggc cgc ttc aag tcc tcg ctg atc aac gac gtg cag ggg atg     432
Asp Glu Gly Arg Phe Lys Ser Ser Leu Ile Asn Asp Val Gln Gly Met
    130                 135                 140 ctg tcg ctc tac gag gcg gcc tac atg gcg gtg cgc ggc gag cat atc     480
Leu Ser Leu Tyr Glu Ala Ala Tyr Met Ala Val Arg Gly Glu His Ile
145                 150                 155                 160 ctc gac gag gcg atc gcc ttc acc acc acc cat ctg aaa tcg ctc gtg     528
Leu Asp Glu Ala Ile Ala Phe Thr Thr Thr His Leu Lys Ser Leu Val
                165                 170                 175 gcg cag gac cat gtc acg ccg aag ctc gcc gag cag atc aac cat gcg     576
Ala Gln Asp His Val Thr Pro Lys Leu Ala Glu Gln Ile Asn His Ala
            180                 185                 190 ctc tac cgc ccg ctg cgc aag acg ctg ccg cgg ctc gag gcg cgc tat     624
Leu Tyr Arg Pro Leu Arg Lys Thr Leu Pro Arg Leu Glu Ala Arg Tyr
        195                 200                 205 ttc atg tcg atg atc aac tcg acc tcg gac cat ctc tac aac aag acg     672
Phe Met Ser Met Ile Asn Ser Thr Ser Asp His Leu Tyr Asn Lys Thr
    210                 215                 220 ctg ctg aac ttc gcc aag ctc gac ttc aac atc ctg ctc gag ctg cac     720
Leu Leu Asn Phe Ala Lys Leu Asp Phe Asn Ile Leu Leu Glu Leu His
```

```
Leu Leu Asn Phe Ala Lys Leu Asp Phe Asn Ile Leu Leu Glu Leu His
225                 230                 235                 240 aag gaa gag ctg aac gag ctg acg aaa tgg tgg aag gat ctc gac ttc      768
Lys Glu Glu Leu Asn Glu Leu Thr Lys Trp Trp Lys Asp Leu Asp Phe
                    245                 250                 255 acc acc aag ctg ccc tat gcg cgc gac cgg ctg gtc gag ctc tat ttc      816
Thr Thr Lys Leu Pro Tyr Ala Arg Asp Arg Leu Val Glu Leu Tyr Phe
                260                 265                 270 tgg gat ctc ggc acc tat ttc gag ccg cag tat gcc ttc ggc cgc aag      864
Trp Asp Leu Gly Thr Tyr Phe Glu Pro Gln Tyr Ala Phe Gly Arg Lys
            275                 280                 285 atc atg acc cag ctg aac tac atc ctc tcg atc atc gac gac acc tac      912
Ile Met Thr Gln Leu Asn Tyr Ile Leu Ser Ile Ile Asp Asp Thr Tyr
        290                 295                 300 gac gcc tac ggc acg ctg gaa gag ctg tcg ctc ttc acc gag gcg gtg      960
Asp Ala Tyr Gly Thr Leu Glu Glu Leu Ser Leu Phe Thr Glu Ala Val
305                 310                 315                 320 cag cgc tgg aac atc gag gcg gtc gac atg ctg ccg gaa tac atg aag     1008
Gln Arg Trp Asn Ile Glu Ala Val Asp Met Leu Pro Glu Tyr Met Lys
                325                 330                 335 ctg atc tac cgc acg ctg ctc gat gcc ttc aac gag atc gag gaa gac     1056
Leu Ile Tyr Arg Thr Leu Leu Asp Ala Phe Asn Glu Ile Glu Glu Asp
                340                 345                 350 atg gcg aaa caa ggg cgc agc cac tgc gtg cgc tat gcc aag gaa gag     1104
Met Ala Lys Gln Gly Arg Ser His Cys Val Arg Tyr Ala Lys Glu Glu
            355                 360                 365 aac cag aag gtc atc ggc gcc tat tcg gtc cag gcg aaa tgg ttc tcg     1152
Asn Gln Lys Val Ile Gly Ala Tyr Ser Val Gln Ala Lys Trp Phe Ser
        370                 375                 380 gaa ggc tat gtc ccc acg atc gag gaa tac atg ccg atc gcg ctg acc     1200
Glu Gly Tyr Val Pro Thr Ile Glu Glu Tyr Met Pro Ile Ala Leu Thr
385                 390                 395                 400 tcc tgc gcc tat acc ttc gtc atc acc aac agc ttc ctc ggc atg ggc     1248
Ser Cys Ala Tyr Thr Phe Val Ile Thr Asn Ser Phe Leu Gly Met Gly
                405                 410                 415 gac ttc gcc acc aag gaa gtc ttc gaa tgg atc tcg aac aac ccg aag     1296
Asp Phe Ala Thr Lys Glu Val Phe Glu Trp Ile Ser Asn Asn Pro Lys
                420                 425                 430 gtc gtc aag gcg gcc tcg gtc atc tgc cgg ctg atg gac gac atg cag     1344
Val Val Lys Ala Ala Ser Val Ile Cys Arg Leu Met Asp Asp Met Gln
            435                 440                 445 ggc cac gag ttc gag cag aag cgc ggc cat gtc gcc tcg gcc atc gaa     1392
Gly His Glu Phe Glu Gln Lys Arg Gly His Val Ala Ser Ala Ile Glu
450                 455                 460 tgc tac acc aag cag cac ggc gtc tcg aag gaa gag gcg atc aag atg     1440
Cys Tyr Thr Lys Gln His Gly Val Ser Lys Glu Glu Ala Ile Lys Met
465                 470                 475                 480 ttc gaa gag gaa gtg gcc aat gcc tgg aag gac atc aac gag gaa ctg     1488
Phe Glu Glu Glu Val Ala Asn Ala Trp Lys Asp Ile Asn Glu Glu Leu
                485                 490                 495 atg atg aag ccc acc gtc gtg gcc cgt ccg ctg ctc ggc acg atc ctg     1536
Met Met Lys Pro Thr Val Val Ala Arg Pro Leu Leu Gly Thr Ile Leu
                500                 505                 510 aac ctc gcc cgc gcc atc gac ttc atc tac aag gaa gac gac ggc tat     1584
Asn Leu Ala Arg Ala Ile Asp Phe Ile Tyr Lys Glu Asp Asp Gly Tyr
            515                 520                 525 acc cat tcc tat ctg atc aag gac cag atc gcc tcg gtc ctc ggc gac     1632
Thr His Ser Tyr Leu Ile Lys Asp Gln Ile Ala Ser Val Leu Gly Asp
        530                 535                 540
```

```
cat gtg cct ttc att aat tga taa                                      1656
His Val Pro Phe Ile Asn
545             550

<210> SEQ ID NO 9
<211> LENGTH: 550
<212> TYPE: PRT
<213> ORGANISM: Artificial
<220> FEATURE:
<223> OTHER INFORMATION: Synthetic Construct

<400> SEQUENCE: 9

Met Ser Ser Gly Glu Thr Phe Arg Pro Thr Ala Asp Phe His Pro Ser
1               5                   10                  15

Leu Trp Arg Asn His Phe Leu Lys Gly Ala Ser Asp Phe Lys Thr Val
            20                  25                  30

Asp His Thr Ala Thr Gln Glu Arg His Glu Ala Leu Lys Glu Glu Val
        35                  40                  45

Arg Arg Met Ile Thr Asp Ala Glu Asp Lys Pro Val Gln Lys Leu Arg
    50                  55                  60

Leu Ile Asp Glu Val Gln Arg Leu Gly Val Ala Tyr His Phe Glu Lys
65                  70                  75                  80

Glu Ile Glu Asp Ala Ile Gln Lys Leu Cys Pro Ile Tyr Ile Asp Ser
                85                  90                  95

Asn Arg Ala Asp Leu His Thr Val Ser Leu His Phe Arg Leu Leu Arg
            100                 105                 110

Gln Gln Gly Ile Lys Ile Ser Cys Asp Val Phe Glu Lys Phe Lys Asp
        115                 120                 125

Asp Glu Gly Arg Phe Lys Ser Ser Leu Ile Asn Asp Val Gln Gly Met
    130                 135                 140

Leu Ser Leu Tyr Glu Ala Ala Tyr Met Ala Val Arg Gly Glu His Ile
145                 150                 155                 160

Leu Asp Glu Ala Ile Ala Phe Thr Thr Thr His Leu Lys Ser Leu Val
                165                 170                 175

Ala Gln Asp His Val Thr Pro Lys Leu Ala Glu Gln Ile Asn His Ala
            180                 185                 190

Leu Tyr Arg Pro Leu Arg Lys Thr Leu Pro Arg Leu Glu Ala Arg Tyr
        195                 200                 205

Phe Met Ser Met Ile Asn Ser Thr Ser Asp His Leu Tyr Asn Lys Thr
    210                 215                 220

Leu Leu Asn Phe Ala Lys Leu Asp Phe Asn Ile Leu Leu Glu Leu His
225                 230                 235                 240

Lys Glu Glu Leu Asn Glu Leu Thr Lys Trp Trp Lys Asp Leu Asp Phe
                245                 250                 255

Thr Thr Lys Leu Pro Tyr Ala Arg Asp Arg Leu Val Glu Leu Tyr Phe
            260                 265                 270

Trp Asp Leu Gly Thr Tyr Phe Glu Pro Gln Tyr Ala Phe Gly Arg Lys
        275                 280                 285

Ile Met Thr Gln Leu Asn Tyr Ile Leu Ser Ile Asp Asp Thr Tyr
    290                 295                 300

Asp Ala Tyr Gly Thr Leu Glu Glu Leu Ser Leu Phe Thr Glu Ala Val
305                 310                 315                 320

Gln Arg Trp Asn Ile Glu Ala Val Asp Met Leu Pro Glu Tyr Met Lys
                325                 330                 335

Leu Ile Tyr Arg Thr Leu Leu Asp Ala Phe Asn Glu Ile Glu Glu Asp
            340                 345                 350
```

```
Met Ala Lys Gln Gly Arg Ser His Cys Val Arg Tyr Ala Lys Glu Glu
        355                 360                 365
Asn Gln Lys Val Ile Gly Ala Tyr Ser Val Gln Ala Lys Trp Phe Ser
    370                 375                 380
Glu Gly Tyr Val Pro Thr Ile Glu Glu Tyr Met Pro Ile Ala Leu Thr
385                 390                 395                 400
Ser Cys Ala Tyr Thr Phe Val Ile Thr Asn Ser Phe Leu Gly Met Gly
                405                 410                 415
Asp Phe Ala Thr Lys Glu Val Phe Glu Trp Ile Ser Asn Asn Pro Lys
            420                 425                 430
Val Val Lys Ala Ala Ser Val Ile Cys Arg Leu Met Asp Asp Met Gln
        435                 440                 445
Gly His Glu Phe Glu Gln Lys Arg Gly His Val Ala Ser Ala Ile Glu
    450                 455                 460
Cys Tyr Thr Lys Gln His Gly Val Ser Lys Glu Ala Ile Lys Met
465                 470                 475                 480
Phe Glu Glu Glu Val Ala Asn Ala Trp Lys Asp Ile Asn Glu Glu Leu
                485                 490                 495
Met Met Lys Pro Thr Val Val Ala Arg Pro Leu Leu Gly Thr Ile Leu
            500                 505                 510
Asn Leu Ala Arg Ala Ile Asp Phe Ile Tyr Lys Glu Asp Asp Gly Tyr
        515                 520                 525
Thr His Ser Tyr Leu Ile Lys Asp Gln Ile Ala Ser Val Leu Gly Asp
    530                 535                 540
His Val Pro Phe Ile Asn
545                 550
```

<210> SEQ ID NO 10
<211> LENGTH: 2778
<212> TYPE: DNA
<213> ORGANISM: Artificial
<220> FEATURE:
<223> OTHER INFORMATION: synthetic fusion gene MBP-ValFpoR
<220> FEATURE:
<221> NAME/KEY: CDS
<222> LOCATION: (1)..(2778)

<400> SEQUENCE: 10

```
atg aag atc gag gaa ggc aag ctc gtc atc tgg atc aac ggc gac aag      48
Met Lys Ile Glu Glu Gly Lys Leu Val Ile Trp Ile Asn Gly Asp Lys
1               5                   10                  15 ggc tac aac ggc ctc gcc gag gtg ggc aag aag ttc gag aag gac acg      96
Gly Tyr Asn Gly Leu Ala Glu Val Gly Lys Lys Phe Glu Lys Asp Thr
            20                  25                  30 ggc atc aag gtc acc gtc gag cat ccc gac aag ctc gag gag aag ttc     144
Gly Ile Lys Val Thr Val Glu His Pro Asp Lys Leu Glu Glu Lys Phe
        35                  40                  45 ccg cag gtc gcc gcc acc ggc gac ggc ccc gac atc atc ttc tgg gcc     192
Pro Gln Val Ala Ala Thr Gly Asp Gly Pro Asp Ile Ile Phe Trp Ala
    50                  55                  60 cac gac cgc ttc ggc ggc tat gcg cag tcg ggc ctg ctc gcc gag atc     240
His Asp Arg Phe Gly Gly Tyr Ala Gln Ser Gly Leu Leu Ala Glu Ile
65                  70                  75                  80 acg ccc gac aag gcc ttc cag gac aag ctc tat ccc ttc acc tgg gat     288
Thr Pro Asp Lys Ala Phe Gln Asp Lys Leu Tyr Pro Phe Thr Trp Asp
                85                  90                  95 gcg gtg cgc tac aac ggc aag ctg atc gcc tat ccg atc gcc gtc gag     336
Ala Val Arg Tyr Asn Gly Lys Leu Ile Ala Tyr Pro Ile Ala Val Glu
```

-continued

```
              100                 105                 110
gcg ctg tcg ctg atc tac aac aag gat ctg ctg ccg aac ccg ccg aag     384
Ala Leu Ser Leu Ile Tyr Asn Lys Asp Leu Leu Pro Asn Pro Pro Lys
            115                 120                 125 acc tgg gaa gag atc ccg gcg ctc gac aag gaa ctg aag gcc aag ggc     432
Thr Trp Glu Glu Ile Pro Ala Leu Asp Lys Glu Leu Lys Ala Lys Gly
130                 135                 140 aag tcc gcg ctg atg ttc aac ctg cag gag ccc tat ttc acc tgg ccg     480
Lys Ser Ala Leu Met Phe Asn Leu Gln Glu Pro Tyr Phe Thr Trp Pro
145                 150                 155                 160 ctg atc gcc gcc gac ggc ggc tat gcc ttc aaa tac gag aac ggc aaa     528
Leu Ile Ala Ala Asp Gly Gly Tyr Ala Phe Lys Tyr Glu Asn Gly Lys
                    165                 170                 175 tac gac atc aag gac gtg ggc gtc gac aat gcg ggc gcc aag gcc ggg     576
Tyr Asp Ile Lys Asp Val Gly Val Asp Asn Ala Gly Ala Lys Ala Gly
            180                 185                 190 ctg acc ttc ctc gtc gat ctg atc aag aac aag cac atg aat gcc gac     624
Leu Thr Phe Leu Val Asp Leu Ile Lys Asn Lys His Met Asn Ala Asp
        195                 200                 205 acc gac tat tcc atc gcc gag gcg gcc ttc aac aag ggc gag acc gcc     672
Thr Asp Tyr Ser Ile Ala Glu Ala Ala Phe Asn Lys Gly Glu Thr Ala
    210                 215                 220 atg acg atc aac ggg ccg tgg gcc tgg tcg aac atc gac acc tcg aag     720
Met Thr Ile Asn Gly Pro Trp Ala Trp Ser Asn Ile Asp Thr Ser Lys
225                 230                 235                 240 gtc aat tac ggc gtc acg gtg ctg ccg acc ttc aag ggc cag ccc tcg     768
Val Asn Tyr Gly Val Thr Val Leu Pro Thr Phe Lys Gly Gln Pro Ser
                245                 250                 255 aaa ccc ttc gtc ggc gtg ctg tcg gcg ggc atc aac gcg gcc tcg ccg     816
Lys Pro Phe Val Gly Val Leu Ser Ala Gly Ile Asn Ala Ala Ser Pro
            260                 265                 270 aac aag gaa ctc gcc aag gag ttc ctc gag aac tac ctg ctg acc gac     864
Asn Lys Glu Leu Ala Lys Glu Phe Leu Glu Asn Tyr Leu Leu Thr Asp
        275                 280                 285 gag ggg ctc gag gcg gtg aac aag gac aag ccg ctc ggc gcg gtg gcg     912
Glu Gly Leu Glu Ala Val Asn Lys Asp Lys Pro Leu Gly Ala Val Ala
    290                 295                 300 ctg aaa tcc tac gag gaa gag ctc gtc aag gac ccg cgg atc gcc gcc     960
Leu Lys Ser Tyr Glu Glu Glu Leu Val Lys Asp Pro Arg Ile Ala Ala
305                 310                 315                 320 acg atg gag aat gcg cag aag ggc gag atc atg ccg aac atc ccg cag    1008
Thr Met Glu Asn Ala Gln Lys Gly Glu Ile Met Pro Asn Ile Pro Gln
                325                 330                 335 atg tcg gcc ttc tgg tat gcc gtc cgc acc gcg gtg atc aac gcg gcc    1056
Met Ser Ala Phe Trp Tyr Ala Val Arg Thr Ala Val Ile Asn Ala Ala
            340                 345                 350 tcg ggc cgt cag acc gtc gac gag gcg ctg aag gat gcg cag act ggt    1104
Ser Gly Arg Gln Thr Val Asp Glu Ala Leu Lys Asp Ala Gln Thr Gly
        355                 360                 365 gat gac gac gac aag att aat agc tcg ggc gag acc ttc cgc ccg acc    1152
Asp Asp Asp Asp Lys Ile Asn Ser Ser Gly Glu Thr Phe Arg Pro Thr
    370                 375                 380 gcc gat ttc cat ccc tcg ctc tgg cgc aac cat ttc ctg aag ggc gcc    1200
Ala Asp Phe His Pro Ser Leu Trp Arg Asn His Phe Leu Lys Gly Ala
385                 390                 395                 400 tcc gac ttc aag acc gtc gat cac acg gcc acc cag gag cgc cac gag    1248
Ser Asp Phe Lys Thr Val Asp His Thr Ala Thr Gln Glu Arg His Glu
                405                 410                 415 gcg ctg aag gaa gag gtg cgc cgg atg atc acc gac gcc gag gac aag    1296
```

```
                Ala Leu Lys Glu Glu Val Arg Arg Met Ile Thr Asp Ala Glu Asp Lys
                            420                 425                 430 ccg gtg cag aag ctg cgg ctg atc gac gag gtg cag cgt ctc ggc gtg       1344
Pro Val Gln Lys Leu Arg Leu Ile Asp Glu Val Gln Arg Leu Gly Val
            435                 440                 445 gcc tat cac ttc gag aag gag atc gag gat gcg atc cag aag ctc tgc       1392
Ala Tyr His Phe Glu Lys Glu Ile Glu Asp Ala Ile Gln Lys Leu Cys
        450                 455                 460 ccg atc tac atc gac agc aac cgc gcc gat ctg cac acg gtc tcg ctg       1440
Pro Ile Tyr Ile Asp Ser Asn Arg Ala Asp Leu His Thr Val Ser Leu
465                 470                 475                 480 cat ttc cgg ctg ctg cgc cag cag ggc atc aag atc tcc tgc gac gtc       1488
His Phe Arg Leu Leu Arg Gln Gln Gly Ile Lys Ile Ser Cys Asp Val
                485                 490                 495 ttc gag aag ttc aag gac gac gag ggc cgc ttc aag tcc tcg ctg atc       1536
Phe Glu Lys Phe Lys Asp Asp Glu Gly Arg Phe Lys Ser Ser Leu Ile
            500                 505                 510 aac gac gtg cag ggg atg ctg tcg ctc tac gag gcg gcc tac atg gcg       1584
Asn Asp Val Gln Gly Met Leu Ser Leu Tyr Glu Ala Ala Tyr Met Ala
        515                 520                 525 gtg cgc ggc gag cat atc ctc gac gag gcg atc gcc ttc acc acc acc       1632
Val Arg Gly Glu His Ile Leu Asp Glu Ala Ile Ala Phe Thr Thr Thr
530                 535                 540 cat ctg aaa tcg ctc gtg gcg cag gac cat gtc acg ccg aag ctc gcc       1680
His Leu Lys Ser Leu Val Ala Gln Asp His Val Thr Pro Lys Leu Ala
                545                 550                 555                 560 gag cag atc aac cat gcg ctc tac cgc ccg ctg cgc aag acg ctg ccg       1728
Glu Gln Ile Asn His Ala Leu Tyr Arg Pro Leu Arg Lys Thr Leu Pro
            565                 570                 575 cgg ctc gag gcg cgc tat ttc atg tcg atg atc aac tcg acc tcg gac       1776
Arg Leu Glu Ala Arg Tyr Phe Met Ser Met Ile Asn Ser Thr Ser Asp
        580                 585                 590 cat ctc tac aac aag acg ctg ctg aac ttc gcc aag ctc gac ttc aac       1824
His Leu Tyr Asn Lys Thr Leu Leu Asn Phe Ala Lys Leu Asp Phe Asn
595                 600                 605 atc ctg ctc gag ctg cac aag gaa gag ctg aac gag ctg acg aaa tgg       1872
Ile Leu Leu Glu Leu His Lys Glu Glu Leu Asn Glu Leu Thr Lys Trp
610                 615                 620 tgg aag gat ctc gac ttc acc acc aag ctg ccc tat gcg cgc gac cgg       1920
Trp Lys Asp Leu Asp Phe Thr Thr Lys Leu Pro Tyr Ala Arg Asp Arg
625                 630                 635                 640 ctg gtc gag ctc tat ttc tgg gat ctc ggc acc tat ttc gag ccg cag       1968
Leu Val Glu Leu Tyr Phe Trp Asp Leu Gly Thr Tyr Phe Glu Pro Gln
            645                 650                 655 tat gcc ttc ggc cgc aag atc atg acc cag ctg aac tac atc ctc tcg       2016
Tyr Ala Phe Gly Arg Lys Ile Met Thr Gln Leu Asn Tyr Ile Leu Ser
        660                 665                 670 atc atc gac gac acc tac gac gcc tac ggc acg ctg gaa gag ctg tcg       2064
Ile Ile Asp Asp Thr Tyr Asp Ala Tyr Gly Thr Leu Glu Glu Leu Ser
                675                 680                 685 ctc ttc acc gag gcg gtg cag cgc tgg aac atc gag gcg gtc gac atg       2112
Leu Phe Thr Glu Ala Val Gln Arg Trp Asn Ile Glu Ala Val Asp Met
            690                 695                 700 ctg ccg gaa tac atg aag ctg atc tac cgc acg ctg ctc gat gcc ttc       2160
Leu Pro Glu Tyr Met Lys Leu Ile Tyr Arg Thr Leu Leu Asp Ala Phe
705                 710                 715                 720 aac gag atc gag gaa gac atg gcg aaa caa ggg cgc agc cac tgc gtg       2208
Asn Glu Ile Glu Glu Asp Met Ala Lys Gln Gly Arg Ser His Cys Val
                725                 730                 735
```

| | | | | | | | | | | | | | | | |
|---|---|---|---|---|---|---|---|---|---|---|---|---|---|---|---|
| cgc | tat | gcc | aag | gaa | gag | aac | cag | aag | gtc | atc | ggc | gcc | tat | tcg | gtc | 2256 |
| Arg | Tyr | Ala | Lys | Glu | Glu | Asn | Gln | Lys | Val | Ile | Gly | Ala | Tyr | Ser | Val | |
| | | | 740 | | | | | 745 | | | | | 750 | | | |
| cag | gcg | aaa | tgg | ttc | tcg | gaa | ggc | tat | gtc | ccc | acg | atc | gag | gaa | tac | 2304 |
| Gln | Ala | Lys | Trp | Phe | Ser | Glu | Gly | Tyr | Val | Pro | Thr | Ile | Glu | Glu | Tyr | |
| | | 755 | | | | | 760 | | | | | 765 | | | | |
| atg | ccg | atc | gcg | ctg | acc | tcc | tgc | gcc | tat | acc | ttc | gtc | atc | acc | aac | 2352 |
| Met | Pro | Ile | Ala | Leu | Thr | Ser | Cys | Ala | Tyr | Thr | Phe | Val | Ile | Thr | Asn | |
| | 770 | | | | | 775 | | | | | 780 | | | | | |
| agc | ttc | ctc | ggc | atg | ggc | gac | ttc | gcc | acc | aag | gaa | gtc | ttc | gaa | tgg | 2400 |
| Ser | Phe | Leu | Gly | Met | Gly | Asp | Phe | Ala | Thr | Lys | Glu | Val | Phe | Glu | Trp | |
| 785 | | | | | 790 | | | | | 795 | | | | | 800 | |
| atc | tcg | aac | aac | ccg | aag | gtc | gtc | aag | gcg | gcc | tcg | gtc | atc | tgc | cgg | 2448 |
| Ile | Ser | Asn | Asn | Pro | Lys | Val | Val | Lys | Ala | Ala | Ser | Val | Ile | Cys | Arg | |
| | | | | 805 | | | | | 810 | | | | | 815 | | |
| ctg | atg | gac | gac | atg | cag | ggc | cac | gag | ttc | gag | cag | aag | cgc | ggc | cat | 2496 |
| Leu | Met | Asp | Asp | Met | Gln | Gly | His | Glu | Phe | Glu | Gln | Lys | Arg | Gly | His | |
| | | | 820 | | | | | 825 | | | | | 830 | | | |
| gtc | gcc | tcg | gcc | atc | gaa | tgc | tac | acc | aag | cag | cac | ggc | gtc | tcg | aag | 2544 |
| Val | Ala | Ser | Ala | Ile | Glu | Cys | Tyr | Thr | Lys | Gln | His | Gly | Val | Ser | Lys | |
| | | 835 | | | | | 840 | | | | | 845 | | | | |
| gaa | gag | gcg | atc | aag | atg | ttc | gaa | gag | gaa | gtg | gcc | aat | gcc | tgg | aag | 2592 |
| Glu | Glu | Ala | Ile | Lys | Met | Phe | Glu | Glu | Glu | Val | Ala | Asn | Ala | Trp | Lys | |
| | 850 | | | | | 855 | | | | | 860 | | | | | |
| gac | atc | aac | gag | gaa | ctg | atg | atg | aag | ccc | acc | gtc | gtg | gcc | cgt | ccg | 2640 |
| Asp | Ile | Asn | Glu | Glu | Leu | Met | Met | Lys | Pro | Thr | Val | Val | Ala | Arg | Pro | |
| 865 | | | | | 870 | | | | | 875 | | | | | 880 | |
| ctg | ctc | ggc | acg | atc | ctg | aac | ctc | gcc | cgc | gcc | atc | gac | ttc | atc | tac | 2688 |
| Leu | Leu | Gly | Thr | Ile | Leu | Asn | Leu | Ala | Arg | Ala | Ile | Asp | Phe | Ile | Tyr | |
| | | | | 885 | | | | | 890 | | | | | 895 | | |
| aag | gaa | gac | gac | ggc | tat | acc | cat | tcc | tat | ctg | atc | aag | gac | cag | atc | 2736 |
| Lys | Glu | Asp | Asp | Gly | Tyr | Thr | His | Ser | Tyr | Leu | Ile | Lys | Asp | Gln | Ile | |
| | | | 900 | | | | | 905 | | | | | 910 | | | |
| gcc | tcg | gtc | ctc | ggc | gac | cat | gtg | cct | ttc | att | aat | tga | taa | | | 2778 |
| Ala | Ser | Val | Leu | Gly | Asp | His | Val | Pro | Phe | Ile | Asn | | | | | |
| | | 915 | | | | | 920 | | | | | | | | | |

```
<210> SEQ ID NO 11
<211> LENGTH: 924
<212> TYPE: PRT
<213> ORGANISM: Artificial
<220> FEATURE:
<223> OTHER INFORMATION: Synthetic Construct

<400> SEQUENCE: 11
```

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

```
Ala Leu Ser Leu Ile Tyr Asn Lys Asp Leu Leu Pro Asn Pro Pro Lys
            115                 120                 125

Thr Trp Glu Glu Ile Pro Ala Leu Asp Lys Glu Leu Lys Ala Lys Gly
130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Leu Val Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Gly
        355                 360                 365

Asp Asp Asp Asp Lys Ile Asn Ser Ser Gly Glu Thr Phe Arg Pro Thr
    370                 375                 380

Ala Asp Phe His Pro Ser Leu Trp Arg Asn His Phe Leu Lys Gly Ala
385                 390                 395                 400

Ser Asp Phe Lys Thr Val Asp His Thr Ala Thr Gln Glu Arg His Glu
                405                 410                 415

Ala Leu Lys Glu Glu Val Arg Arg Met Ile Thr Asp Ala Glu Asp Lys
            420                 425                 430

Pro Val Gln Lys Leu Arg Leu Ile Asp Glu Val Gln Arg Leu Gly Val
        435                 440                 445

Ala Tyr His Phe Glu Lys Glu Ile Glu Asp Ala Ile Gln Lys Leu Cys
    450                 455                 460

Pro Ile Tyr Ile Asp Ser Asn Arg Ala Asp Leu His Thr Val Ser Leu
465                 470                 475                 480

His Phe Arg Leu Leu Arg Gln Gln Gly Ile Lys Ile Ser Cys Asp Val
                485                 490                 495

Phe Glu Lys Phe Lys Asp Asp Glu Gly Arg Phe Lys Ser Ser Leu Ile
            500                 505                 510

Asn Asp Val Gln Gly Met Leu Ser Leu Tyr Glu Ala Ala Tyr Met Ala
        515                 520                 525

Val Arg Gly Glu His Ile Leu Asp Glu Ala Ile Ala Phe Thr Thr Thr
```

```
                530                 535                 540
His Leu Lys Ser Leu Val Ala Gln Asp His Val Thr Pro Lys Leu Ala
545                 550                 555                 560

Glu Gln Ile Asn His Ala Leu Tyr Arg Pro Leu Arg Lys Thr Leu Pro
                565                 570                 575

Arg Leu Glu Ala Arg Tyr Phe Met Ser Met Ile Asn Ser Thr Ser Asp
                580                 585                 590

His Leu Tyr Asn Lys Thr Leu Leu Asn Phe Ala Lys Leu Asp Phe Asn
                595                 600                 605

Ile Leu Leu Glu Leu His Lys Glu Glu Leu Asn Glu Leu Thr Lys Trp
610                 615                 620

Trp Lys Asp Leu Asp Phe Thr Thr Lys Leu Pro Tyr Ala Arg Asp Arg
625                 630                 635                 640

Leu Val Glu Leu Tyr Phe Trp Asp Leu Gly Thr Tyr Phe Glu Pro Gln
                645                 650                 655

Tyr Ala Phe Gly Arg Lys Ile Met Thr Gln Leu Asn Tyr Ile Leu Ser
                660                 665                 670

Ile Ile Asp Asp Thr Tyr Asp Ala Tyr Gly Thr Leu Glu Glu Leu Ser
                675                 680                 685

Leu Phe Thr Glu Ala Val Gln Arg Trp Asn Ile Glu Ala Val Asp Met
690                 695                 700

Leu Pro Glu Tyr Met Lys Leu Ile Tyr Arg Thr Leu Leu Asp Ala Phe
705                 710                 715                 720

Asn Glu Ile Glu Glu Asp Met Ala Lys Gln Gly Arg Ser His Cys Val
                725                 730                 735

Arg Tyr Ala Lys Glu Glu Asn Gln Lys Val Ile Gly Ala Tyr Ser Val
                740                 745                 750

Gln Ala Lys Trp Phe Ser Glu Gly Tyr Val Pro Thr Ile Glu Glu Tyr
                755                 760                 765

Met Pro Ile Ala Leu Thr Ser Cys Ala Tyr Thr Phe Val Ile Thr Asn
770                 775                 780

Ser Phe Leu Gly Met Gly Asp Phe Ala Thr Lys Glu Val Phe Glu Trp
785                 790                 795                 800

Ile Ser Asn Asn Pro Lys Val Val Lys Ala Ala Ser Val Ile Cys Arg
                805                 810                 815

Leu Met Asp Asp Met Gln Gly His Glu Phe Glu Gln Lys Arg Gly His
                820                 825                 830

Val Ala Ser Ala Ile Glu Cys Tyr Thr Lys Gln His Gly Val Ser Lys
                835                 840                 845

Glu Glu Ala Ile Lys Met Phe Glu Glu Val Ala Asn Ala Trp Lys
850                 855                 860

Asp Ile Asn Glu Glu Leu Met Met Lys Pro Thr Val Val Ala Arg Pro
865                 870                 875                 880

Leu Leu Gly Thr Ile Leu Asn Leu Ala Arg Ala Ile Asp Phe Ile Tyr
                885                 890                 895

Lys Glu Asp Asp Gly Tyr Thr His Ser Tyr Leu Ile Lys Asp Gln Ile
                900                 905                 910

Ala Ser Val Leu Gly Asp His Val Pro Phe Ile Asn
                915                 920

<210> SEQ ID NO 12
<211> LENGTH: 3159
<212> TYPE: DNA
<213> ORGANISM: Artificial
```

<220> FEATURE:
<223> OTHER INFORMATION: synthetic fusion gene NusA-ValFpoR
<220> FEATURE:
<221> NAME/KEY: CDS
<222> LOCATION: (1)..(3159)

<400> SEQUENCE: 12

| | | | | | | | | | | | | | | | | |
|---|---|---|---|---|---|---|---|---|---|---|---|---|---|---|---|---|
| atg | aac | aag | gag | atc | ctg | gcc | gtc | gtc | gag | gcg | gtc | tcg | aac | gag | aag | 48 |
| Met | Asn | Lys | Glu | Ile | Leu | Ala | Val | Val | Glu | Ala | Val | Ser | Asn | Glu | Lys | |
| 1 | | | | 5 | | | | | 10 | | | | | 15 | | |
| gcg | ctg | ccg | cgc | gag | aag | atc | ttc | gag | gcg | ctg | gaa | tcc | gcg | ctg | gcc | 96 |
| Ala | Leu | Pro | Arg | Glu | Lys | Ile | Phe | Glu | Ala | Leu | Glu | Ser | Ala | Leu | Ala | |
| | | | 20 | | | | | 25 | | | | | 30 | | | |
| acc | gcc | acc | aag | aag | aaa | tac | gag | cag | gag | atc | gac | gtg | cgc | gtg | cag | 144 |
| Thr | Ala | Thr | Lys | Lys | Lys | Tyr | Glu | Gln | Glu | Ile | Asp | Val | Arg | Val | Gln | |
| | | 35 | | | | | 40 | | | | | 45 | | | | |
| atc | gac | agg | aaa | tcc | ggc | gac | ttc | gac | acc | ttc | cgc | cgc | tgg | ctc | gtc | 192 |
| Ile | Asp | Arg | Lys | Ser | Gly | Asp | Phe | Asp | Thr | Phe | Arg | Arg | Trp | Leu | Val | |
| | 50 | | | | | 55 | | | | | 60 | | | | | |
| gtc | gac | gag | gtc | acg | cag | ccg | acc | aag | gag | atc | acg | ctc | gag | gcg | gcc | 240 |
| Val | Asp | Glu | Val | Thr | Gln | Pro | Thr | Lys | Glu | Ile | Thr | Leu | Glu | Ala | Ala | |
| 65 | | | | | 70 | | | | | 75 | | | | | 80 | |
| cgc | tac | gag | gac | gag | agc | ctg | aac | ctc | ggc | gac | tat | gtc | gag | gat | cag | 288 |
| Arg | Tyr | Glu | Asp | Glu | Ser | Leu | Asn | Leu | Gly | Asp | Tyr | Val | Glu | Asp | Gln | |
| | | | | 85 | | | | | 90 | | | | | 95 | | |
| atc | gag | agc | gtc | acc | ttc | gac | cgg | atc | acc | acg | cag | acc | gcc | aag | cag | 336 |
| Ile | Glu | Ser | Val | Thr | Phe | Asp | Arg | Ile | Thr | Thr | Gln | Thr | Ala | Lys | Gln | |
| | | | 100 | | | | | 105 | | | | | 110 | | | |
| gtc | atc | gtg | cag | aag | gtc | cgc | gag | gcc | gag | cgg | gcg | atg | gtc | gtc | gat | 384 |
| Val | Ile | Val | Gln | Lys | Val | Arg | Glu | Ala | Glu | Arg | Ala | Met | Val | Val | Asp | |
| | | 115 | | | | | 120 | | | | | 125 | | | | |
| cag | ttc | cgc | gag | cac | gag | ggc | gag | atc | atc | acc | ggc | gtg | gtg | aag | aag | 432 |
| Gln | Phe | Arg | Glu | His | Glu | Gly | Glu | Ile | Ile | Thr | Gly | Val | Val | Lys | Lys | |
| | 130 | | | | | 135 | | | | | 140 | | | | | |
| gtc | aac | cgc | gac | aac | atc | tcg | ctc | gat | ctc | ggc | aac | aat | gcc | gag | gcg | 480 |
| Val | Asn | Arg | Asp | Asn | Ile | Ser | Leu | Asp | Leu | Gly | Asn | Asn | Ala | Glu | Ala | |
| 145 | | | | | 150 | | | | | 155 | | | | | 160 | |
| gtg | atc | ctg | cgc | gag | gac | atg | ctg | ccg | cgc | gag | aac | ttc | cgc | ccg | ggc | 528 |
| Val | Ile | Leu | Arg | Glu | Asp | Met | Leu | Pro | Arg | Glu | Asn | Phe | Arg | Pro | Gly | |
| | | | | 165 | | | | | 170 | | | | | 175 | | |
| gac | cgg | gtg | cgc | ggc | gtg | ctc | tat | tcc | gtc | cgt | ccc | gag | gcg | cgc | ggc | 576 |
| Asp | Arg | Val | Arg | Gly | Val | Leu | Tyr | Ser | Val | Arg | Pro | Glu | Ala | Arg | Gly | |
| | | | 180 | | | | | 185 | | | | | 190 | | | |
| gcg | cag | ctc | ttc | gtc | acc | cgc | tcg | aag | ccc | gag | atg | ctg | atc | gag | ctg | 624 |
| Ala | Gln | Leu | Phe | Val | Thr | Arg | Ser | Lys | Pro | Glu | Met | Leu | Ile | Glu | Leu | |
| | | | 195 | | | | | 200 | | | | | 205 | | | |
| ttc | cgc | atc | gag | gtg | ccc | gag | atc | ggc | gag | gaa | gtg | atc | gag | atc | aag | 672 |
| Phe | Arg | Ile | Glu | Val | Pro | Glu | Ile | Gly | Glu | Glu | Val | Ile | Glu | Ile | Lys | |
| | | 210 | | | | | 215 | | | | | 220 | | | | |
| gcc | gcg | gcc | cgc | gac | ccg | ggc | tcg | cgc | gcc | aag | atc | gcc | gtc | aag | acc | 720 |
| Ala | Ala | Ala | Arg | Asp | Pro | Gly | Ser | Arg | Ala | Lys | Ile | Ala | Val | Lys | Thr | |
| 225 | | | | | 230 | | | | | 235 | | | | | 240 | |
| aac | gac | aag | cgg | atc | gac | ccg | gtg | ggc | gcc | tgc | gtg | ggc | atg | cgc | ggc | 768 |
| Asn | Asp | Lys | Arg | Ile | Asp | Pro | Val | Gly | Ala | Cys | Val | Gly | Met | Arg | Gly | |
| | | | | 245 | | | | | 250 | | | | | 255 | | |
| gcg | cgg | gtg | cag | gcc | gtc | tcg | acc | gag | ctc | ggc | ggc | gag | cgg | atc | gac | 816 |
| Ala | Arg | Val | Gln | Ala | Val | Ser | Thr | Glu | Leu | Gly | Gly | Glu | Arg | Ile | Asp | |
| | | | 260 | | | | | 265 | | | | | 270 | | | |
| atc | gtg | ctc | tgg | gac | gac | aat | ccg | gcg | cag | ttc | gtc | atc | aat | gcc | atg | 864 |
| Ile | Val | Leu | Trp | Asp | Asp | Asn | Pro | Ala | Gln | Phe | Val | Ile | Asn | Ala | Met | |
| | | 275 | | | | | 280 | | | | | 285 | | | | |

```
gcg ccc gcc gac gtg gcc tcg atc gtc gtc gac gag gac aag cac acg    912
Ala Pro Ala Asp Val Ala Ser Ile Val Val Asp Glu Asp Lys His Thr
    290                 295                 300 atg gac atc gcc gtc gag gcg ggc aac ctc gcg cag gcc atc ggc cgc    960
Met Asp Ile Ala Val Glu Ala Gly Asn Leu Ala Gln Ala Ile Gly Arg
305                 310                 315                 320 aac ggg cag aac gtg cgg ctg gcc tcg cag ctc tcg ggc tgg gag ctg   1008
Asn Gly Gln Asn Val Arg Leu Ala Ser Gln Leu Ser Gly Trp Glu Leu
                325                 330                 335 aac gtg atg acc gtc gac gat ctg cag gcc aag cac cag gcc gag gcc   1056
Asn Val Met Thr Val Asp Asp Leu Gln Ala Lys His Gln Ala Glu Ala
            340                 345                 350 cat gcg gcc atc gac acc ttc acc aaa tat ctc gac atc gac gag gat   1104
His Ala Ala Ile Asp Thr Phe Thr Lys Tyr Leu Asp Ile Asp Glu Asp
        355                 360                 365 ttc gcc acg gtt ctc gtc gaa gag ggc ttc tcg acg ctg gaa gag ctg   1152
Phe Ala Thr Val Leu Val Glu Glu Gly Phe Ser Thr Leu Glu Glu Leu
    370                 375                 380 gcc tat gtg ccg atg aag gaa ctg ctc gag atc gag ggg ctc gac gag   1200
Ala Tyr Val Pro Met Lys Glu Leu Leu Glu Ile Glu Gly Leu Asp Glu
385                 390                 395                 400 ccg acc gtc gag gcg ctg cgc gag cgc gcc aag aac gcg ctg gcc acc   1248
Pro Thr Val Glu Ala Leu Arg Glu Arg Ala Lys Asn Ala Leu Ala Thr
                405                 410                 415 atc gcg cag gcg cag gaa gag agc ctc ggc gac aac aag ccc gcc gac   1296
Ile Ala Gln Ala Gln Glu Glu Ser Leu Gly Asp Asn Lys Pro Ala Asp
            420                 425                 430 gat ctg ctg aac ctc gag ggc gtc gac cgc gac ctg gcc ttc aag ctg   1344
Asp Leu Leu Asn Leu Glu Gly Val Asp Arg Asp Leu Ala Phe Lys Leu
        435                 440                 445 gcc gcg cgc ggc gtc tgc acg ctc gag gat ctg gcc gag cag ggc atc   1392
Ala Ala Arg Gly Val Cys Thr Leu Glu Asp Leu Ala Glu Gln Gly Ile
    450                 455                 460 gac gat ctg gcc gac atc gag ggg ctg acc gac gag aag gcg ggc gcg   1440
Asp Asp Leu Ala Asp Ile Glu Gly Leu Thr Asp Glu Lys Ala Gly Ala
465                 470                 475                 480 ctg atc atg gcc gcc cgc aac atc tgc tgg ttc ggc gac gaa ggt gat   1488
Leu Ile Met Ala Ala Arg Asn Ile Cys Trp Phe Gly Asp Glu Gly Asp
                485                 490                 495 gac gac gac aag att aat agc tcg ggc gag acc ttc cgc ccg acc gcc   1536
Asp Asp Asp Lys Ile Asn Ser Ser Gly Glu Thr Phe Arg Pro Thr Ala
            500                 505                 510 gat ttc cat ccc tcg ctc tgg cgc aac cat ttc ctg aag ggc gcc tcc   1584
Asp Phe His Pro Ser Leu Trp Arg Asn His Phe Leu Lys Gly Ala Ser
        515                 520                 525 gac ttc aag acc gtc gat cac acg gcc acc cag gag cgc cac gag gcg   1632
Asp Phe Lys Thr Val Asp His Thr Ala Thr Gln Glu Arg His Glu Ala
    530                 535                 540 ctg aag gaa gag gtg cgc cgg atg atc acc gac gcc gag gac aag ccg   1680
Leu Lys Glu Glu Val Arg Arg Met Ile Thr Asp Ala Glu Asp Lys Pro
545                 550                 555                 560 gtg cag aag ctg cgg ctg atc gac gag gtg cag cgt ctc ggc gtg gcc   1728
Val Gln Lys Leu Arg Leu Ile Asp Glu Val Gln Arg Leu Gly Val Ala
                565                 570                 575 tat cac ttc gag aag gag atc gag gat gcg atc cag aag ctc tgc ccg   1776
Tyr His Phe Glu Lys Glu Ile Glu Asp Ala Ile Gln Lys Leu Cys Pro
            580                 585                 590 atc tac atc gac agc aac cgc gcc gat ctg cac acg gtc tcg ctg cat   1824
Ile Tyr Ile Asp Ser Asn Arg Ala Asp Leu His Thr Val Ser Leu His
```

|  |  |
|---|---|
| ttc cgg ctg ctg cgc cag cag ggc atc aag atc tcc tgc gac gtc ttc<br>Phe Arg Leu Leu Arg Gln Gln Gly Ile Lys Ile Ser Cys Asp Val Phe<br>610                               615                         620 | 1872 |
| gag aag ttc aag gac gac gag ggc cgc ttc aag tcc tcg ctg atc aac<br>Glu Lys Phe Lys Asp Asp Glu Gly Arg Phe Lys Ser Ser Leu Ile Asn<br>625                         630                       635                   640 | 1920 |
| gac gtg cag ggg atg ctg tcg ctc tac gag gcg gcc tac atg gcg gtg<br>Asp Val Gln Gly Met Leu Ser Leu Tyr Glu Ala Ala Tyr Met Ala Val<br>                         645                       650                   655 | 1968 |
| cgc ggc gag cat atc ctc gac gag gcg atc gcc ttc acc acc acc cat<br>Arg Gly Glu His Ile Leu Asp Glu Ala Ile Ala Phe Thr Thr Thr His<br>            660                       665                       670 | 2016 |
| ctg aaa tcg ctc gtg gcg cag gac cat gtc acg ccg aag ctc gcc gag<br>Leu Lys Ser Leu Val Ala Gln Asp His Val Thr Pro Lys Leu Ala Glu<br>675                         680                       685 | 2064 |
| cag atc aac cat gcg ctc tac cgc ccg ctg cgc aag acg ctg ccg cgg<br>Gln Ile Asn His Ala Leu Tyr Arg Pro Leu Arg Lys Thr Leu Pro Arg<br>690                             695                       700 | 2112 |
| ctc gag gcg cgc tat ttc atg tcg atg atc aac tcg acc tcg gac cat<br>Leu Glu Ala Arg Tyr Phe Met Ser Met Ile Asn Ser Thr Ser Asp His<br>705                        710                       715                   720 | 2160 |
| ctc tac aac aag acg ctg ctg aac ttc gcc aag ctc gac ttc aac atc<br>Leu Tyr Asn Lys Thr Leu Leu Asn Phe Ala Lys Leu Asp Phe Asn Ile<br>                  725                       730                       735 | 2208 |
| ctg ctc gag ctg cac aag gaa gag ctg aac gag ctg acg aaa tgg tgg<br>Leu Leu Glu Leu His Lys Glu Glu Leu Asn Glu Leu Thr Lys Trp Trp<br>            740                       745                       750 | 2256 |
| aag gat ctc gac ttc acc acc aag ctg ccc tat gcg cgc gac cgg ctg<br>Lys Asp Leu Asp Phe Thr Thr Lys Leu Pro Tyr Ala Arg Asp Arg Leu<br>755                         760                       765 | 2304 |
| gtc gag ctc tat ttc tgg gat ctc ggc acc tat ttc gag ccg cag tat<br>Val Glu Leu Tyr Phe Trp Asp Leu Gly Thr Tyr Phe Glu Pro Gln Tyr<br>770                         775                       780 | 2352 |
| gcc ttc ggc cgc aag atc atg acc cag ctg aac tac atc ctc tcg atc<br>Ala Phe Gly Arg Lys Ile Met Thr Gln Leu Asn Tyr Ile Leu Ser Ile<br>785                         790                       795                   800 | 2400 |
| atc gac gac acc tac gac gcc tac ggc acg ctg gaa gag ctg tcg ctc<br>Ile Asp Asp Thr Tyr Asp Ala Tyr Gly Thr Leu Glu Glu Leu Ser Leu<br>                  805                       810                   815 | 2448 |
| ttc acc gag gcg gtg cag cgc tgg aac atc gag gcg gtc gac atg ctg<br>Phe Thr Glu Ala Val Gln Arg Trp Asn Ile Glu Ala Val Asp Met Leu<br>            820                       825                       830 | 2496 |
| ccg gaa tac atg aag ctg atc tac cgc acg ctg ctc gat gcc ttc aac<br>Pro Glu Tyr Met Lys Leu Ile Tyr Arg Thr Leu Leu Asp Ala Phe Asn<br>835                         840                       845 | 2544 |
| gag atc gag gaa gac atg gcg aaa caa ggg cgc agc cac tgc gtg cgc<br>Glu Ile Glu Glu Asp Met Ala Lys Gln Gly Arg Ser His Cys Val Arg<br>850                         855                       860 | 2592 |
| tat gcc aag gaa gag aac cag aag gtc atc ggc gcc tat tcg gtc cag<br>Tyr Ala Lys Glu Glu Asn Gln Lys Val Ile Gly Ala Tyr Ser Val Gln<br>865                         870                       875                   880 | 2640 |
| gcg aaa tgg ttc tcg gaa ggc tat gtc ccc acg atc gag gaa tac atg<br>Ala Lys Trp Phe Ser Glu Gly Tyr Val Pro Thr Ile Glu Glu Tyr Met<br>                  885                       890                   895 | 2688 |
| ccg atc gcg ctg acc tcc tgc gcc tat acc ttc gtc atc acc aac agc<br>Pro Ile Ala Leu Thr Ser Cys Ala Tyr Thr Phe Val Ile Thr Asn Ser<br>            900                       905                       910 | 2736 |
| ttc ctc ggc atg ggc gac ttc gcc acc aag gaa gtc ttc gaa tgg atc | 2784 |

```
                Phe Leu Gly Met Gly Asp Phe Ala Thr Lys Glu Val Phe Glu Trp Ile
                                915                 920                 925 tcg aac aac ccg aag gtc gtc aag gcg gcc tcg gtc atc tgc cgg ctg             2832
Ser Asn Asn Pro Lys Val Val Lys Ala Ala Ser Val Ile Cys Arg Leu
    930                 935                 940 atg gac gac atg cag ggc cac gag ttc gag cag aag cgc ggc cat gtc             2880
Met Asp Asp Met Gln Gly His Glu Phe Glu Gln Lys Arg Gly His Val
945                 950                 955                 960 gcc tcg gcc atc gaa tgc tac acc aag cag cac ggc gtc tcg aag gaa             2928
Ala Ser Ala Ile Glu Cys Tyr Thr Lys Gln His Gly Val Ser Lys Glu
                965                 970                 975 gag gcg atc aag atg ttc gaa gag gaa gtg gcc aat gcc tgg aag gac             2976
Glu Ala Ile Lys Met Phe Glu Glu Glu Val Ala Asn Ala Trp Lys Asp
            980                 985                 990 atc aac gag gaa ctg atg atg aag  ccc acc gtc gtg gcc  cgt ccg ctg           3024
Ile Asn Glu Glu Leu Met Met Lys  Pro Thr Val Val Ala  Arg Pro Leu
                995                 1000                1005 ctc ggc  acg atc ctg aac ctc  gcc cgc gcc atc gac  ttc atc tac              3069
Leu Gly  Thr Ile Leu Asn Leu  Ala Arg Ala Ile Asp  Phe Ile Tyr
         1010                 1015                 1020 aag gaa  gac gac ggc tat acc  cat tcc tat ctg atc  aag gac cag              3114
Lys Glu  Asp Asp Gly Tyr Thr  His Ser Tyr Leu Ile  Lys Asp Gln
1025                 1030                 1035 atc gcc  tcg gtc ctc ggc gac  cat gtg cct ttc att  aat tga taa              3159
Ile Ala  Ser Val Leu Gly Asp  His Val Pro Phe Ile  Asn
         1040                 1045                 1050

<210> SEQ ID NO 13
<211> LENGTH: 1051
<212> TYPE: PRT
<213> ORGANISM: Artificial
<220> FEATURE:
<223> OTHER INFORMATION: Synthetic Construct

<400> SEQUENCE: 13

Met Asn Lys Glu Ile Leu Ala Val Val Glu Ala Val Ser Asn Glu Lys
1               5                   10                  15

Ala Leu Pro Arg Glu Lys Ile Phe Glu Ala Leu Glu Ser Ala Leu Ala
            20                  25                  30

Thr Ala Thr Lys Lys Lys Tyr Glu Gln Glu Ile Asp Val Arg Val Gln
        35                  40                  45

Ile Asp Arg Lys Ser Gly Asp Phe Asp Thr Phe Arg Arg Trp Leu Val
    50                  55                  60

Val Asp Glu Val Thr Gln Pro Thr Lys Glu Ile Thr Leu Glu Ala Ala
65                  70                  75                  80

Arg Tyr Glu Asp Glu Ser Leu Asn Leu Gly Asp Tyr Val Glu Asp Gln
            85                  90                  95

Ile Glu Ser Val Thr Phe Asp Arg Ile Thr Thr Gln Thr Ala Lys Gln
            100                 105                 110

Val Ile Val Gln Lys Val Arg Glu Ala Glu Arg Ala Met Val Val Asp
        115                 120                 125

Gln Phe Arg Glu His Glu Gly Glu Ile Ile Thr Gly Val Val Lys Lys
    130                 135                 140

Val Asn Arg Asp Asn Ile Ser Leu Asp Leu Gly Asn Asn Ala Glu Ala
145                 150                 155                 160

Val Ile Leu Arg Glu Asp Met Leu Pro Arg Glu Asn Phe Arg Pro Gly
            165                 170                 175

Asp Arg Val Arg Gly Val Leu Tyr Ser Val Arg Pro Glu Ala Arg Gly
```

```
                180             185             190
Ala Gln Leu Phe Val Thr Arg Ser Lys Pro Glu Met Leu Ile Glu Leu
            195                 200                 205
Phe Arg Ile Glu Val Pro Glu Ile Gly Glu Glu Val Ile Glu Ile Lys
210                 215                 220
Ala Ala Ala Arg Asp Pro Gly Ser Arg Ala Lys Ile Ala Val Lys Thr
225                 230                 235                 240
Asn Asp Lys Arg Ile Asp Pro Val Gly Ala Cys Val Gly Met Arg Gly
                245                 250                 255
Ala Arg Val Gln Ala Val Ser Thr Glu Leu Gly Gly Glu Arg Ile Asp
            260                 265                 270
Ile Val Leu Trp Asp Asp Asn Pro Ala Gln Phe Val Ile Asn Ala Met
            275                 280                 285
Ala Pro Ala Asp Val Ala Ser Ile Val Val Asp Glu Asp Lys His Thr
            290                 295                 300
Met Asp Ile Ala Val Glu Ala Gly Asn Leu Ala Gln Ala Ile Gly Arg
305                 310                 315                 320
Asn Gly Gln Asn Val Arg Leu Ala Ser Gln Leu Ser Gly Trp Glu Leu
                325                 330                 335
Asn Val Met Thr Val Asp Asp Leu Gln Ala Lys His Gln Ala Glu Ala
            340                 345                 350
His Ala Ala Ile Asp Thr Phe Thr Lys Tyr Leu Asp Ile Asp Glu Asp
            355                 360                 365
Phe Ala Thr Val Leu Val Glu Glu Gly Phe Ser Thr Leu Glu Glu Leu
            370                 375                 380
Ala Tyr Val Pro Met Lys Glu Leu Leu Glu Ile Glu Gly Leu Asp Glu
385                 390                 395                 400
Pro Thr Val Glu Ala Leu Arg Glu Arg Ala Lys Asn Ala Leu Ala Thr
                405                 410                 415
Ile Ala Gln Ala Gln Glu Glu Ser Leu Gly Asp Asn Lys Pro Ala Asp
            420                 425                 430
Asp Leu Leu Asn Leu Glu Gly Val Asp Arg Asp Leu Ala Phe Lys Leu
            435                 440                 445
Ala Ala Arg Gly Val Cys Thr Leu Glu Asp Leu Ala Glu Gln Gly Ile
            450                 455                 460
Asp Asp Leu Ala Asp Ile Glu Gly Leu Thr Asp Glu Lys Ala Gly Ala
465                 470                 475                 480
Leu Ile Met Ala Ala Arg Asn Ile Cys Trp Phe Gly Asp Glu Gly Asp
                485                 490                 495
Asp Asp Asp Lys Ile Asn Ser Ser Gly Glu Thr Phe Arg Pro Thr Ala
            500                 505                 510
Asp Phe His Pro Ser Leu Trp Arg Asn His Phe Leu Lys Gly Ala Ser
            515                 520                 525
Asp Phe Lys Thr Val Asp His Thr Ala Thr Gln Glu Arg His Glu Ala
            530                 535                 540
Leu Lys Glu Glu Val Arg Arg Met Ile Thr Asp Ala Glu Asp Lys Pro
545                 550                 555                 560
Val Gln Lys Leu Arg Leu Ile Asp Glu Val Gln Arg Leu Gly Val Ala
                565                 570                 575
Tyr His Phe Glu Lys Glu Ile Glu Asp Ala Ile Gln Lys Leu Cys Pro
            580                 585                 590
Ile Tyr Ile Asp Ser Asn Arg Ala Asp Leu His Thr Val Ser Leu His
            595                 600                 605
```

-continued

Phe Arg Leu Leu Arg Gln Gln Gly Ile Lys Ile Ser Cys Asp Val Phe
610                 615                 620

Glu Lys Phe Lys Asp Asp Glu Gly Arg Phe Lys Ser Ser Leu Ile Asn
625                 630                 635                 640

Asp Val Gln Gly Met Leu Ser Leu Tyr Glu Ala Ala Tyr Met Ala Val
            645                 650                 655

Arg Gly Glu His Ile Leu Asp Glu Ala Ile Ala Phe Thr Thr Thr His
            660                 665                 670

Leu Lys Ser Leu Val Ala Gln Asp His Val Thr Pro Lys Leu Ala Glu
            675                 680                 685

Gln Ile Asn His Ala Leu Tyr Arg Pro Leu Arg Lys Thr Leu Pro Arg
690                 695                 700

Leu Glu Ala Arg Tyr Phe Met Ser Met Ile Asn Ser Thr Ser Asp His
705                 710                 715                 720

Leu Tyr Asn Lys Thr Leu Leu Asn Phe Ala Lys Leu Asp Phe Asn Ile
            725                 730                 735

Leu Leu Glu Leu His Lys Glu Glu Leu Asn Glu Leu Thr Lys Trp Trp
            740                 745                 750

Lys Asp Leu Asp Phe Thr Thr Lys Leu Pro Tyr Ala Arg Asp Arg Leu
            755                 760                 765

Val Glu Leu Tyr Phe Trp Asp Leu Gly Thr Tyr Phe Glu Pro Gln Tyr
770                 775                 780

Ala Phe Gly Arg Lys Ile Met Thr Gln Leu Asn Tyr Ile Leu Ser Ile
785                 790                 795                 800

Ile Asp Asp Thr Tyr Asp Ala Tyr Gly Thr Leu Glu Glu Leu Ser Leu
            805                 810                 815

Phe Thr Glu Ala Val Gln Arg Trp Asn Ile Glu Ala Val Asp Met Leu
            820                 825                 830

Pro Glu Tyr Met Lys Leu Ile Tyr Arg Thr Leu Leu Asp Ala Phe Asn
            835                 840                 845

Glu Ile Glu Glu Asp Met Ala Lys Gln Gly Arg Ser His Cys Val Arg
850                 855                 860

Tyr Ala Lys Glu Glu Asn Gln Lys Val Ile Gly Ala Tyr Ser Val Gln
865                 870                 875                 880

Ala Lys Trp Phe Ser Glu Gly Tyr Val Pro Thr Ile Glu Glu Tyr Met
            885                 890                 895

Pro Ile Ala Leu Thr Ser Cys Ala Tyr Thr Phe Val Ile Thr Asn Ser
            900                 905                 910

Phe Leu Gly Met Gly Asp Phe Ala Thr Lys Glu Val Phe Glu Trp Ile
            915                 920                 925

Ser Asn Asn Pro Lys Val Val Lys Ala Ala Ser Val Ile Cys Arg Leu
930                 935                 940

Met Asp Asp Met Gln Gly His Glu Phe Glu Gln Lys Arg Gly His Val
945                 950                 955                 960

Ala Ser Ala Ile Glu Cys Tyr Thr Lys Gln His Gly Val Ser Lys Glu
            965                 970                 975

Glu Ala Ile Lys Met Phe Glu Glu Val Ala Asn Ala Trp Lys Asp
            980                 985                 990

Ile Asn Glu Glu Leu Met Met Lys Pro Thr Val Val Ala Arg Pro Leu
            995                1000                1005

Leu Gly Thr Ile Leu Asn Leu Ala Arg Ala Ile Asp Phe Ile Tyr
         1010                1015                1020

-continued

```
Lys Glu Asp Asp Gly Tyr Thr His Ser Tyr Leu Ile Lys Asp Gln
    1025                1030                1035

Ile Ala Ser Val Leu Gly Asp His Val Pro Phe Ile Asn
    1040                1045                1050

<210> SEQ ID NO 14
<211> LENGTH: 2007
<212> TYPE: DNA
<213> ORGANISM: Artificial
<220> FEATURE:
<223> OTHER INFORMATION: synthetic fusion gene Trx-ValFpoR
<220> FEATURE:
<221> NAME/KEY: CDS
<222> LOCATION: (1)..(2007)

<400> SEQUENCE: 14 atg tcg gac aag atc atc cac ctg acc gac gac agc ttc gac acc gac     48
Met Ser Asp Lys Ile Ile His Leu Thr Asp Asp Ser Phe Asp Thr Asp
1               5                   10                  15 gtg ctg aag gcc gac ggc gcc atc ctc gtc gat ttc tgg gcc gaa tgg     96
Val Leu Lys Ala Asp Gly Ala Ile Leu Val Asp Phe Trp Ala Glu Trp
            20                  25                  30 tgc ggc ccc tgc aag atg atc gcg ccg atc ctc gac gag atc gcc gac    144
Cys Gly Pro Cys Lys Met Ile Ala Pro Ile Leu Asp Glu Ile Ala Asp
        35                  40                  45 gaa tat cag ggc aag ctg acc gtc gcc aag ctg aac atc gac cag aac    192
Glu Tyr Gln Gly Lys Leu Thr Val Ala Lys Leu Asn Ile Asp Gln Asn
    50                  55                  60 ccg ggc acg gcg ccg aaa tac ggc atc cgc ggc atc ccg acg ctg ctg    240
Pro Gly Thr Ala Pro Lys Tyr Gly Ile Arg Gly Ile Pro Thr Leu Leu
65                  70                  75                  80 ctc ttc aag aac ggc gag gtg gcg gcc acc aag gtc ggc gcg ctg tcg    288
Leu Phe Lys Asn Gly Glu Val Ala Ala Thr Lys Val Gly Ala Leu Ser
                85                  90                  95 aag ggc cag ctg aag gag ttc ctc gat gcg aac ctc gcc ggt ggt gat    336
Lys Gly Gln Leu Lys Glu Phe Leu Asp Ala Asn Leu Ala Gly Gly Asp
            100                 105                 110 gac gac gac aag att aat agc tcg ggc gag acc ttc cgc ccg acc gcc    384
Asp Asp Asp Lys Ile Asn Ser Ser Gly Glu Thr Phe Arg Pro Thr Ala
        115                 120                 125 gat ttc cat ccc tcg ctc tgg cgc aac cat ttc ctg aag ggc gcc tcc    432
Asp Phe His Pro Ser Leu Trp Arg Asn His Phe Leu Lys Gly Ala Ser
    130                 135                 140 gac ttc aag acc gtc gat cac acg gcc acc cag gag cgc cac gag gcg    480
Asp Phe Lys Thr Val Asp His Thr Ala Thr Gln Glu Arg His Glu Ala
145                 150                 155                 160 ctg aag gaa gag gtg cgc cgg atg atc acc gac gcc gag gac aag ccg    528
Leu Lys Glu Glu Val Arg Arg Met Ile Thr Asp Ala Glu Asp Lys Pro
                165                 170                 175 gtg cag aag ctg cgg ctg atc gac gag gtg cag cgt ctc ggc gtg gcc    576
Val Gln Lys Leu Arg Leu Ile Asp Glu Val Gln Arg Leu Gly Val Ala
            180                 185                 190 tat cac ttc gag aag gag atc gag gat gcg atc cag aag ctc tgc ccg    624
Tyr His Phe Glu Lys Glu Ile Glu Asp Ala Ile Gln Lys Leu Cys Pro
        195                 200                 205 atc tac atc gac agc aac cgc gcc gat ctg cac acg gtc tcg ctg cat    672
Ile Tyr Ile Asp Ser Asn Arg Ala Asp Leu His Thr Val Ser Leu His
    210                 215                 220 ttc cgg ctg ctg cgc cag cag ggc atc aag atc tcc tgc gac gtc ttc    720
Phe Arg Leu Leu Arg Gln Gln Gly Ile Lys Ile Ser Cys Asp Val Phe
225                 230                 235                 240
```

```
gag aag ttc aag gac gac gag ggc cgc ttc aag tcc tcg ctg atc aac         768
Glu Lys Phe Lys Asp Asp Glu Gly Arg Phe Lys Ser Ser Leu Ile Asn
                245                 250                 255 gac gtg cag ggg atg ctg tcg ctc tac gag gcg gcc tac atg gcg gtg         816
Asp Val Gln Gly Met Leu Ser Leu Tyr Glu Ala Ala Tyr Met Ala Val
            260                 265                 270 cgc ggc gag cat atc ctc gac gag gcg atc gcc ttc acc acc acc cat         864
Arg Gly Glu His Ile Leu Asp Glu Ala Ile Ala Phe Thr Thr Thr His
        275                 280                 285 ctg aaa tcg ctc gtg gcg cag gac cat gtc acg ccg aag ctc gcc gag         912
Leu Lys Ser Leu Val Ala Gln Asp His Val Thr Pro Lys Leu Ala Glu
    290                 295                 300 cag atc aac cat gcg ctc tac cgc ccg ctg cgc aag acg ctg ccg cgg         960
Gln Ile Asn His Ala Leu Tyr Arg Pro Leu Arg Lys Thr Leu Pro Arg
305                 310                 315                 320 ctc gag gcg cgc tat ttc atg tcg atg atc aac tcg acc tcg gac cat        1008
Leu Glu Ala Arg Tyr Phe Met Ser Met Ile Asn Ser Thr Ser Asp His
                325                 330                 335 ctc tac aac aag acg ctg ctg aac ttc gcc aag ctc gac ttc aac atc        1056
Leu Tyr Asn Lys Thr Leu Leu Asn Phe Ala Lys Leu Asp Phe Asn Ile
            340                 345                 350 ctg ctc gag ctg cac aag gaa gag ctg aac gag ctg acg aaa tgg tgg        1104
Leu Leu Glu Leu His Lys Glu Glu Leu Asn Glu Leu Thr Lys Trp Trp
        355                 360                 365 aag gat ctc gac ttc acc acc aag ctg ccc tat gcg cgc gac cgg ctg        1152
Lys Asp Leu Asp Phe Thr Thr Lys Leu Pro Tyr Ala Arg Asp Arg Leu
    370                 375                 380 gtc gag ctc tat ttc tgg gat ctc ggc acc tat ttc gag ccg cag tat        1200
Val Glu Leu Tyr Phe Trp Asp Leu Gly Thr Tyr Phe Glu Pro Gln Tyr
385                 390                 395                 400 gcc ttc ggc cgc aag atc atg acc cag ctg aac tac atc ctc tcg atc        1248
Ala Phe Gly Arg Lys Ile Met Thr Gln Leu Asn Tyr Ile Leu Ser Ile
                405                 410                 415 atc gac gac acc tac gac gcc tac ggc acg ctg gaa gag ctg tcg ctc        1296
Ile Asp Asp Thr Tyr Asp Ala Tyr Gly Thr Leu Glu Glu Leu Ser Leu
            420                 425                 430 ttc acc gag gcg gtg cag cgc tgg aac atc gag gcg gtc gac atg ctg        1344
Phe Thr Glu Ala Val Gln Arg Trp Asn Ile Glu Ala Val Asp Met Leu
        435                 440                 445 ccg gaa tac atg aag ctg atc tac cgc acg ctg ctc gat gcc ttc aac        1392
Pro Glu Tyr Met Lys Leu Ile Tyr Arg Thr Leu Leu Asp Ala Phe Asn
    450                 455                 460 gag atc gag gaa gac atg gcg aaa caa ggg cgc agc cac tgc gtg cgc        1440
Glu Ile Glu Glu Asp Met Ala Lys Gln Gly Arg Ser His Cys Val Arg
465                 470                 475                 480 tat gcc aag gaa gag aac cag aag gtc atc ggc gcc tat tcg gtc cag        1488
Tyr Ala Lys Glu Glu Asn Gln Lys Val Ile Gly Ala Tyr Ser Val Gln
                485                 490                 495 gcg aaa tgg ttc tcg gaa ggc tat gtc ccc acg atc gag gaa tac atg        1536
Ala Lys Trp Phe Ser Glu Gly Tyr Val Pro Thr Ile Glu Glu Tyr Met
            500                 505                 510 ccg atc gcg ctg acc tcc tgc gcc tat acc ttc gtc atc acc aac agc        1584
Pro Ile Ala Leu Thr Ser Cys Ala Tyr Thr Phe Val Ile Thr Asn Ser
        515                 520                 525 ttc ctc ggc atg ggc gac ttc gcc acc aag gaa gtc ttc gaa tgg atc        1632
Phe Leu Gly Met Gly Asp Phe Ala Thr Lys Glu Val Phe Glu Trp Ile
    530                 535                 540 tcg aac aac ccg aag gtc gtc aag gcg gcc tcg gtc atc tgc cgg ctg        1680
Ser Asn Asn Pro Lys Val Val Lys Ala Ala Ser Val Ile Cys Arg Leu
545                 550                 555                 560
```

```
atg gac gac atg cag ggc cac gag ttc gag cag aag cgc ggc cat gtc      1728
Met Asp Asp Met Gln Gly His Glu Phe Glu Gln Lys Arg Gly His Val
                565                 570                 575 gcc tcg gcc atc gaa tgc tac acc aag cag cac ggc gtc tcg aag gaa      1776
Ala Ser Ala Ile Glu Cys Tyr Thr Lys Gln His Gly Val Ser Lys Glu
            580                 585                 590 gag gcg atc aag atg ttc gaa gag gaa gtg gcc aat gcc tgg aag gac      1824
Glu Ala Ile Lys Met Phe Glu Glu Glu Val Ala Asn Ala Trp Lys Asp
        595                 600                 605 atc aac gag gaa ctg atg atg aag ccc acc gtc gtg gcc cgt ccg ctg      1872
Ile Asn Glu Glu Leu Met Met Lys Pro Thr Val Val Ala Arg Pro Leu
    610                 615                 620 ctc ggc acg atc ctg aac ctc gcc cgc gcc atc gac ttc atc tac aag      1920
Leu Gly Thr Ile Leu Asn Leu Ala Arg Ala Ile Asp Phe Ile Tyr Lys
625                 630                 635                 640 gaa gac gac ggc tat acc cat tcc tat ctg atc aag gac cag atc gcc      1968
Glu Asp Asp Gly Tyr Thr His Ser Tyr Leu Ile Lys Asp Gln Ile Ala
                645                 650                 655 tcg gtc ctc ggc gac cat gtg cct ttc att aat tga taa                  2007
Ser Val Leu Gly Asp His Val Pro Phe Ile Asn
                660                 665
```

<210> SEQ ID NO 15
<211> LENGTH: 667
<212> TYPE: PRT
<213> ORGANISM: Artificial
<220> FEATURE:
<223> OTHER INFORMATION: Synthetic Construct

<400> SEQUENCE: 15

```
Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Cys Lys Met Ile Ala Pro Ile Leu Asp Glu Ile Ala Asp
            35                  40                  45

Glu Tyr Gln Gly Lys Leu Thr Val Ala Lys Leu Asn Ile Asp Gln Asn
        50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Gly Asp
            100                 105                 110

Asp Asp Asp Lys Ile Asn Ser Ser Gly Glu Thr Phe Arg Pro Thr Ala
        115                 120                 125

Asp Phe His Pro Ser Leu Trp Arg Asn His Phe Leu Lys Gly Ala Ser
    130                 135                 140

Asp Phe Lys Thr Val Asp His Thr Ala Thr Gln Glu Arg His Glu Ala
145                 150                 155                 160

Leu Lys Glu Glu Val Arg Arg Met Ile Thr Asp Ala Glu Asp Lys Pro
                165                 170                 175

Val Gln Lys Leu Arg Leu Ile Asp Glu Val Gln Arg Leu Gly Val Ala
            180                 185                 190

Tyr His Phe Glu Lys Glu Ile Glu Asp Ala Ile Gln Lys Leu Cys Pro
        195                 200                 205

Ile Tyr Ile Asp Ser Asn Arg Ala Asp Leu His Thr Val Ser Leu His
```

```
            210                 215                 220
Phe Arg Leu Leu Arg Gln Gln Gly Ile Lys Ile Ser Cys Asp Val Phe
225                 230                 235                 240

Glu Lys Phe Lys Asp Asp Gly Arg Phe Lys Ser Ser Leu Ile Asn
                245                 250                 255

Asp Val Gln Gly Met Leu Ser Leu Tyr Glu Ala Ala Tyr Met Ala Val
                260                 265                 270

Arg Gly Glu His Ile Leu Asp Glu Ala Ile Ala Phe Thr Thr Thr His
                275                 280                 285

Leu Lys Ser Leu Val Ala Gln Asp His Val Thr Pro Lys Leu Ala Glu
                290                 295                 300

Gln Ile Asn His Ala Leu Tyr Arg Pro Leu Arg Lys Thr Leu Pro Arg
305                 310                 315                 320

Leu Glu Ala Arg Tyr Phe Met Ser Met Ile Asn Ser Thr Ser Asp His
                325                 330                 335

Leu Tyr Asn Lys Thr Leu Leu Asn Phe Ala Lys Leu Asp Phe Asn Ile
                340                 345                 350

Leu Leu Glu Leu His Lys Glu Leu Asn Glu Leu Thr Lys Trp Trp
                355                 360                 365

Lys Asp Leu Asp Phe Thr Thr Lys Leu Pro Tyr Ala Arg Asp Arg Leu
370                 375                 380

Val Glu Leu Tyr Phe Trp Asp Leu Gly Thr Tyr Phe Glu Pro Gln Tyr
385                 390                 395                 400

Ala Phe Gly Arg Lys Ile Met Thr Gln Leu Asn Tyr Ile Leu Ser Ile
                405                 410                 415

Ile Asp Asp Thr Tyr Asp Ala Tyr Gly Thr Leu Glu Glu Leu Ser Leu
                420                 425                 430

Phe Thr Glu Ala Val Gln Arg Trp Asn Ile Glu Ala Val Asp Met Leu
                435                 440                 445

Pro Glu Tyr Met Lys Leu Ile Tyr Arg Thr Leu Leu Asp Ala Phe Asn
450                 455                 460

Glu Ile Glu Glu Asp Met Ala Lys Gln Gly Arg Ser His Cys Val Arg
465                 470                 475                 480

Tyr Ala Lys Glu Glu Asn Gln Lys Val Ile Gly Ala Tyr Ser Val Gln
                485                 490                 495

Ala Lys Trp Phe Ser Glu Gly Tyr Val Pro Thr Ile Glu Glu Tyr Met
                500                 505                 510

Pro Ile Ala Leu Thr Ser Cys Ala Tyr Thr Phe Val Ile Thr Asn Ser
                515                 520                 525

Phe Leu Gly Met Gly Asp Phe Ala Thr Lys Glu Val Phe Glu Trp Ile
                530                 535                 540

Ser Asn Asn Pro Lys Val Val Lys Ala Ala Ser Val Ile Cys Arg Leu
545                 550                 555                 560

Met Asp Asp Met Gln Gly His Glu Phe Glu Gln Lys Arg Gly His Val
                565                 570                 575

Ala Ser Ala Ile Glu Cys Tyr Thr Lys Gln His Gly Val Ser Lys Glu
                580                 585                 590

Glu Ala Ile Lys Met Phe Glu Glu Val Ala Asn Ala Trp Lys Asp
                595                 600                 605

Ile Asn Glu Glu Leu Met Met Lys Pro Thr Val Val Ala Arg Pro Leu
                610                 615                 620

Leu Gly Thr Ile Leu Asn Leu Ala Arg Ala Ile Asp Phe Ile Tyr Lys
625                 630                 635                 640
```

Glu Asp Asp Gly Tyr Thr His Ser Tyr Leu Ile Lys Asp Gln Ile Ala
            645                 650                 655

Ser Val Leu Gly Asp His Val Pro Phe Ile Asn
            660                 665

<210> SEQ ID NO 16
<211> LENGTH: 2772
<212> TYPE: DNA
<213> ORGANISM: Artificial
<220> FEATURE:
<223> OTHER INFORMATION: synthetic fusion gene MBP-ValF
<220> FEATURE:
<221> NAME/KEY: CDS
<222> LOCATION: (1)..(2772)

<400> SEQUENCE: 16

```
atg aag atc gag gaa ggc aag ctc gtc atc tgg atc aac ggc gac aag       48
Met Lys Ile Glu Glu Gly Lys Leu Val Ile Trp Ile Asn Gly Asp Lys
1               5                   10                  15 ggc tac aac ggc ctc gcc gag gtg ggc aag aag ttc gag aag gac acg       96
Gly Tyr Asn Gly Leu Ala Glu Val Gly Lys Lys Phe Glu Lys Asp Thr
            20                  25                  30 ggc atc aag gtc acc gtc gag cat ccc gac aag ctc gag gag aag ttc      144
Gly Ile Lys Val Thr Val Glu His Pro Asp Lys Leu Glu Glu Lys Phe
        35                  40                  45 ccg cag gtc gcc gcc acc ggc gac ggc ccc gac atc atc ttc tgg gcc      192
Pro Gln Val Ala Ala Thr Gly Asp Gly Pro Asp Ile Ile Phe Trp Ala
    50                  55                  60 cac gac cgc ttc ggc ggc tat gcg cag tcg ggc ctg ctc gcc gag atc      240
His Asp Arg Phe Gly Gly Tyr Ala Gln Ser Gly Leu Leu Ala Glu Ile
65                  70                  75                  80 acg ccc gac aag gcc ttc cag gac aag ctc tat ccc ttc acc tgg gat      288
Thr Pro Asp Lys Ala Phe Gln Asp Lys Leu Tyr Pro Phe Thr Trp Asp
                85                  90                  95 gcg gtg cgc tac aac ggc aag ctg atc gcc tat ccg atc gcc gtc gag      336
Ala Val Arg Tyr Asn Gly Lys Leu Ile Ala Tyr Pro Ile Ala Val Glu
            100                 105                 110 gcg ctg tcg ctg atc tac aac aag gat ctg ctg ccg aac ccg ccg aag      384
Ala Leu Ser Leu Ile Tyr Asn Lys Asp Leu Leu Pro Asn Pro Pro Lys
        115                 120                 125 acc tgg gaa gag atc ccg gcg ctc gac aag gaa ctg aag gcc aag ggc      432
Thr Trp Glu Glu Ile Pro Ala Leu Asp Lys Glu Leu Lys Ala Lys Gly
    130                 135                 140 aag tcc gcg ctg atg ttc aac ctg cag gag ccc tat ttc acc tgg ccg      480
Lys Ser Ala Leu Met Phe Asn Leu Gln Glu Pro Tyr Phe Thr Trp Pro
145                 150                 155                 160 ctg atc gcc gcc gac ggc ggc tat gcc ttc aaa tac gag aac ggc aaa      528
Leu Ile Ala Ala Asp Gly Gly Tyr Ala Phe Lys Tyr Glu Asn Gly Lys
                165                 170                 175 tac gac atc aag gac gtg ggc gtc gac aat gcg ggc gcc aag gcc ggg      576
Tyr Asp Ile Lys Asp Val Gly Val Asp Asn Ala Gly Ala Lys Ala Gly
            180                 185                 190 ctg acc ttc ctc gtc gat ctg atc aag aac aag cac atg aat gcc gac      624
Leu Thr Phe Leu Val Asp Leu Ile Lys Asn Lys His Met Asn Ala Asp
        195                 200                 205 acc gac tat tcc atc gcc gag gcg gcc ttc aac aag ggc gag acc gcc      672
Thr Asp Tyr Ser Ile Ala Glu Ala Ala Phe Asn Lys Gly Glu Thr Ala
    210                 215                 220 atg acg atc aac ggg ccg tgg gcc tgg tcg aac atc gac acc tcg aag      720
Met Thr Ile Asn Gly Pro Trp Ala Trp Ser Asn Ile Asp Thr Ser Lys
225                 230                 235                 240
```

-continued

| | |
|---|---|
| gtc aat tac ggc gtc acg gtg ctg ccg acc ttc aag ggc cag ccc tcg<br>Val Asn Tyr Gly Val Thr Val Leu Pro Thr Phe Lys Gly Gln Pro Ser<br>                   245                       250                  255 | 768 |
| aaa ccc ttc gtc ggc gtg ctg tcg gcg ggc atc aac gcg gcc tcg ccg<br>Lys Pro Phe Val Gly Val Leu Ser Ala Gly Ile Asn Ala Ala Ser Pro<br>             260                     265                   270 | 816 |
| aac aag gaa ctc gcc aag gag ttc ctc gag aac tac ctg ctg acc gac<br>Asn Lys Glu Leu Ala Lys Glu Phe Leu Glu Asn Tyr Leu Leu Thr Asp<br>275                       280                   285 | 864 |
| gag ggg ctc gag gcg gtg aac aag gac aag ccg ctc ggc gcg gtg gcg<br>Glu Gly Leu Glu Ala Val Asn Lys Asp Lys Pro Leu Gly Ala Val Ala<br>    290                   295                   300 | 912 |
| ctg aaa tcc tac gag gaa gag ctc gtc aag gac ccg cgg atc gcc gcc<br>Leu Lys Ser Tyr Glu Glu Glu Leu Val Lys Asp Pro Arg Ile Ala Ala<br>305                310                 315              320 | 960 |
| acg atg gag aat gcg cag aag ggc gag atc atg ccg aac atc ccg cag<br>Thr Met Glu Asn Ala Gln Lys Gly Glu Ile Met Pro Asn Ile Pro Gln<br>                   325                   330              335 | 1008 |
| atg tcg gcc ttc tgg tat gcc gtc cgc acc gcg gtg atc aac gcg gcc<br>Met Ser Ala Phe Trp Tyr Ala Val Arg Thr Ala Val Ile Asn Ala Ala<br>             340                     345                  350 | 1056 |
| tcg ggc cgt cag acc gtc gac gag gcg ctg aag gat gcg cag act ggt<br>Ser Gly Arg Gln Thr Val Asp Glu Ala Leu Lys Asp Ala Gln Thr Gly<br>       355                   360                 365 | 1104 |
| gat gac gac gac aag att atg tcg agc ggc gag acc ttc cgc ccc acg<br>Asp Asp Asp Asp Lys Ile Met Ser Ser Gly Glu Thr Phe Arg Pro Thr<br>370                375                 380 | 1152 |
| gcc gac ttc cat ccg tcc ctc tgg cgg aac cac ttc ctc aag ggg gcc<br>Ala Asp Phe His Pro Ser Leu Trp Arg Asn His Phe Leu Lys Gly Ala<br>385                390               395              400 | 1200 |
| tcc gat ttc aag acc gtg gac cat acg gcg acg cag gaa cgg cac gag<br>Ser Asp Phe Lys Thr Val Asp His Thr Ala Thr Gln Glu Arg His Glu<br>             405                     410                  415 | 1248 |
| gcc ctc aag gag gag gtc cgc cgc atg atc acc gac gcc gaa gac aag<br>Ala Leu Lys Glu Glu Val Arg Arg Met Ile Thr Asp Ala Glu Asp Lys<br>                 420                     425              430 | 1296 |
| ccg gtc cag aag ctc cgc ctg atc gac gag gtc cag cgc ctg ggc gtg<br>Pro Val Gln Lys Leu Arg Leu Ile Asp Glu Val Gln Arg Leu Gly Val<br>             435                     440                  445 | 1344 |
| gcg tat cat ttc gag aaa gaa atc gag gat gcg atc cag aag ctc tgc<br>Ala Tyr His Phe Glu Lys Glu Ile Glu Asp Ala Ile Gln Lys Leu Cys<br>    450                   455                   460 | 1392 |
| ccg atc tat atc gat agc aat cgc gcc gat ctc cat acc gtg tcg ctg<br>Pro Ile Tyr Ile Asp Ser Asn Arg Ala Asp Leu His Thr Val Ser Leu<br>465                470                 475              480 | 1440 |
| cac ttc cgc ctg ctg cgg cag cag ggc atc aag atc agc tgc gac gtg<br>His Phe Arg Leu Leu Arg Gln Gln Gly Ile Lys Ile Ser Cys Asp Val<br>             485                     490                  495 | 1488 |
| ttc gaa aag ttc aag gac gac gag ggc cgc ttc aag tcg tcg ctg atc<br>Phe Glu Lys Phe Lys Asp Asp Glu Gly Arg Phe Lys Ser Ser Leu Ile<br>                 500                     505              510 | 1536 |
| aac gac gtg cag ggc atg ctg tcg ctg tac gag gcc gcg tac atg gcc<br>Asn Asp Val Gln Gly Met Leu Ser Leu Tyr Glu Ala Ala Tyr Met Ala<br>             515                     520                  525 | 1584 |
| gtg cgc ggc gag cat atc ctg gac gaa gcc atc gcg ttc acg acc acg<br>Val Arg Gly Glu His Ile Leu Asp Glu Ala Ile Ala Phe Thr Thr Thr<br>    530                   535                   540 | 1632 |
| cat ctg aag tcg ctg gtg gcg cag gac cac gtg acg ccg aag ctc gcc<br>His Leu Lys Ser Leu Val Ala Gln Asp His Val Thr Pro Lys Leu Ala | 1680 |

```
                545                 550                 555                 560
gag cag atc aac cac gcg ctg tat cgg ccg ctc cgc aag acc ctc ccg         1728
Glu Gln Ile Asn His Ala Leu Tyr Arg Pro Leu Arg Lys Thr Leu Pro
            565                 570                 575 cgc ctc gag gcc cgc tat ttc atg agc atg atc aac tcg acc tcg gat         1776
Arg Leu Glu Ala Arg Tyr Phe Met Ser Met Ile Asn Ser Thr Ser Asp
        580                 585                 590 cac ctg tac aat aag acc ctg ctc aac ttc gcg aaa ctg gac ttc aat         1824
His Leu Tyr Asn Lys Thr Leu Leu Asn Phe Ala Lys Leu Asp Phe Asn
    595                 600                 605 atc ctc ctc gag ctg cac aag gag gag ctc aac gag ctg acc aag tgg         1872
Ile Leu Leu Glu Leu His Lys Glu Glu Leu Asn Glu Leu Thr Lys Trp
610                 615                 620 tgg aag gat ctg gac ttc acc acc aag ctg ccg tac gcc cgc gat cgc         1920
Trp Lys Asp Leu Asp Phe Thr Thr Lys Leu Pro Tyr Ala Arg Asp Arg
625                 630                 635                 640 ctc gtg gag ctg tat ttc tgg gac ctg ggc acc tac ttc gaa ccc cag         1968
Leu Val Glu Leu Tyr Phe Trp Asp Leu Gly Thr Tyr Phe Glu Pro Gln
            645                 650                 655 tac gcc ttc ggg cgg aag atc atg acc cag ctc aat tat atc ctc agc         2016
Tyr Ala Phe Gly Arg Lys Ile Met Thr Gln Leu Asn Tyr Ile Leu Ser
        660                 665                 670 atc atc gac gac acc tat gac gcg tac ggc acg ctg gag gag ctg tcc         2064
Ile Ile Asp Asp Thr Tyr Asp Ala Tyr Gly Thr Leu Glu Glu Leu Ser
    675                 680                 685 ctg ttc acg gaa gcc gtc cag cgg tgg aac atc gag gcc gtc gac atg         2112
Leu Phe Thr Glu Ala Val Gln Arg Trp Asn Ile Glu Ala Val Asp Met
690                 695                 700 ctc ccc gag tac atg aaa ctg atc tac cgg acc ctg ctg gat gcc ttc         2160
Leu Pro Glu Tyr Met Lys Leu Ile Tyr Arg Thr Leu Leu Asp Ala Phe
705                 710                 715                 720 aac gag atc gag gag gac atg gcg aaa cag ggc cgg tcc cac tgc gtg         2208
Asn Glu Ile Glu Glu Asp Met Ala Lys Gln Gly Arg Ser His Cys Val
            725                 730                 735 cgc tac gcg aag gaa gag aac cag aag gtc atc ggc gcc tac tcg gtc         2256
Arg Tyr Ala Lys Glu Glu Asn Gln Lys Val Ile Gly Ala Tyr Ser Val
        740                 745                 750 cag gcg aag tgg ttc agc gag ggc tat gtg ccg acg atc gag gaa tat         2304
Gln Ala Lys Trp Phe Ser Glu Gly Tyr Val Pro Thr Ile Glu Glu Tyr
    755                 760                 765 atg ccg atc gcg ctc acc tcg tgc gcg tac acg ttc gtg atc acc aat         2352
Met Pro Ile Ala Leu Thr Ser Cys Ala Tyr Thr Phe Val Ile Thr Asn
770                 775                 780 tcg ttc ctc ggc atg ggc gat ttc gcg acc aag gag gtc ttc gag tgg         2400
Ser Phe Leu Gly Met Gly Asp Phe Ala Thr Lys Glu Val Phe Glu Trp
785                 790                 795                 800 atc agc aac aat ccg aag gtg gtg aag gcg gcc tcg gtc atc tgc cgg         2448
Ile Ser Asn Asn Pro Lys Val Val Lys Ala Ala Ser Val Ile Cys Arg
            805                 810                 815 ctc atg gat gac atg cag ggg cat gag ttc gaa cag aag cgc ggc cac         2496
Leu Met Asp Asp Met Gln Gly His Glu Phe Glu Gln Lys Arg Gly His
        820                 825                 830 gtc gcg tcc gcc atc gag tgc tat acc aag cag cat ggc gtg tcg aag         2544
Val Ala Ser Ala Ile Glu Cys Tyr Thr Lys Gln His Gly Val Ser Lys
    835                 840                 845 gag gag gcc atc aag atg ttc gag gag gaa gtc gcc aac gcg tgg aag         2592
Glu Glu Ala Ile Lys Met Phe Glu Glu Glu Val Ala Asn Ala Trp Lys
850                 855                 860 gac atc aat gag gag ctg atg atg aag ccc acc gtc gtg gcc cgc ccc         2640
```

```
                    -continued

Asp Ile Asn Glu Glu Leu Met Met Lys Pro Thr Val Val Ala Arg Pro
865                 870                 875                 880 ctg ctg ggc acc atc ctg aac ctc gcc cgc gcc atc gac ttc atc tac   2688
Leu Leu Gly Thr Ile Leu Asn Leu Ala Arg Ala Ile Asp Phe Ile Tyr
                885                 890                 895 aag gag gac gat ggg tat acg cat tcc tat ctg atc aag gac cag atc   2736
Lys Glu Asp Asp Gly Tyr Thr His Ser Tyr Leu Ile Lys Asp Gln Ile
            900                 905                 910 gcc tcg gtc ctc ggc gat cat gtc ccg ttc tga taa                   2772
Ala Ser Val Leu Gly Asp His Val Pro Phe
        915                 920

<210> SEQ ID NO 17
<211> LENGTH: 922
<212> TYPE: PRT
<213> ORGANISM: Artificial
<220> FEATURE:
<223> OTHER INFORMATION: Synthetic Construct

<400> SEQUENCE: 17

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
                20                  25                  30

Gly Ile Lys Val Thr Val Glu His Pro Asp Lys Leu Glu Glu Lys Phe
            35                  40                  45

Pro Gln Val Ala Ala Thr Gly Asp Gly Pro Asp Ile Ile Phe Trp Ala
        50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
                100                 105                 110

Ala Leu Ser Leu Ile Tyr Asn Lys Asp Leu Leu Pro Asn Pro Pro Lys
            115                 120                 125

Thr Trp Glu Glu Ile Pro Ala Leu Asp Lys Glu Leu Lys Ala Lys Gly
        130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
                180                 185                 190

Leu Thr Phe Leu Val Asp Leu Ile Lys Asn Lys His Met Asn Ala Asp
            195                 200                 205

Thr Asp Tyr Ser Ile Ala Glu Ala Ala Phe Asn Lys Gly Glu Thr Ala
        210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
                260                 265                 270

Asn Lys Glu Leu Ala Lys Glu Phe Leu Glu Asn Tyr Leu Leu Thr Asp
            275                 280                 285
```

```
Glu Gly Leu Glu Ala Val Asn Lys Asp Lys Pro Leu Gly Ala Val Ala
    290                 295                 300

Leu Lys Ser Tyr Glu Glu Leu Val Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
                340                 345                 350

Ser Gly Arg Gln Thr Val Asp Glu Ala Leu Lys Asp Ala Gln Thr Gly
                355                 360                 365

Asp Asp Asp Asp Lys Ile Met Ser Ser Gly Glu Thr Phe Arg Pro Thr
370                 375                 380

Ala Asp Phe His Pro Ser Leu Trp Arg Asn His Phe Leu Lys Gly Ala
385                 390                 395                 400

Ser Asp Phe Lys Thr Val Asp His Thr Ala Thr Gln Glu Arg His Glu
                405                 410                 415

Ala Leu Lys Glu Glu Val Arg Arg Met Ile Thr Asp Ala Glu Asp Lys
                420                 425                 430

Pro Val Gln Lys Leu Arg Leu Ile Asp Glu Val Gln Arg Leu Gly Val
                435                 440                 445

Ala Tyr His Phe Glu Lys Glu Ile Glu Asp Ala Ile Gln Lys Leu Cys
450                 455                 460

Pro Ile Tyr Ile Asp Ser Asn Arg Ala Asp Leu His Thr Val Ser Leu
465                 470                 475                 480

His Phe Arg Leu Leu Arg Gln Gln Gly Ile Lys Ile Ser Cys Asp Val
                485                 490                 495

Phe Glu Lys Phe Lys Asp Asp Glu Gly Arg Phe Lys Ser Ser Leu Ile
                500                 505                 510

Asn Asp Val Gln Gly Met Leu Ser Leu Tyr Glu Ala Ala Tyr Met Ala
                515                 520                 525

Val Arg Gly Glu His Ile Leu Asp Glu Ala Ile Ala Phe Thr Thr Thr
530                 535                 540

His Leu Lys Ser Leu Val Ala Gln Asp His Val Thr Pro Lys Leu Ala
545                 550                 555                 560

Glu Gln Ile Asn His Ala Leu Tyr Arg Pro Leu Arg Lys Thr Leu Pro
                565                 570                 575

Arg Leu Glu Ala Arg Tyr Phe Met Ser Met Ile Asn Ser Thr Ser Asp
                580                 585                 590

His Leu Tyr Asn Lys Thr Leu Leu Asn Phe Ala Lys Leu Asp Phe Asn
                595                 600                 605

Ile Leu Leu Glu Leu His Lys Glu Glu Leu Asn Glu Leu Thr Lys Trp
610                 615                 620

Trp Lys Asp Leu Asp Phe Thr Thr Lys Leu Pro Tyr Ala Arg Asp Arg
625                 630                 635                 640

Leu Val Glu Leu Tyr Phe Trp Asp Leu Gly Thr Tyr Phe Glu Pro Gln
                645                 650                 655

Tyr Ala Phe Gly Arg Lys Ile Met Thr Gln Leu Asn Tyr Ile Leu Ser
                660                 665                 670

Ile Ile Asp Asp Thr Tyr Asp Ala Tyr Gly Thr Leu Glu Glu Leu Ser
                675                 680                 685

Leu Phe Thr Glu Ala Val Gln Arg Trp Asn Ile Glu Ala Val Asp Met
690                 695                 700

Leu Pro Glu Tyr Met Lys Leu Ile Tyr Arg Thr Leu Leu Asp Ala Phe
```

```
                    705                 710                 715                 720
Asn Glu Ile Glu Glu Asp Met Ala Lys Gln Gly Arg Ser His Cys Val
                    725                 730                 735

Arg Tyr Ala Lys Glu Glu Asn Gln Lys Val Ile Gly Ala Tyr Ser Val
                    740                 745                 750

Gln Ala Lys Trp Phe Ser Glu Gly Tyr Val Pro Thr Ile Glu Glu Tyr
                    755                 760                 765

Met Pro Ile Ala Leu Thr Ser Cys Ala Tyr Thr Phe Val Ile Thr Asn
                    770                 775                 780

Ser Phe Leu Gly Met Gly Asp Phe Ala Thr Lys Glu Val Phe Glu Trp
785                 790                 795                 800

Ile Ser Asn Asn Pro Lys Val Val Lys Ala Ala Ser Val Ile Cys Arg
                    805                 810                 815

Leu Met Asp Asp Met Gln Gly His Glu Phe Glu Gln Lys Arg Gly His
                    820                 825                 830

Val Ala Ser Ala Ile Glu Cys Tyr Thr Lys Gln His Gly Val Ser Lys
                    835                 840                 845

Glu Glu Ala Ile Lys Met Phe Glu Glu Val Ala Asn Ala Trp Lys
850                 855                 860

Asp Ile Asn Glu Glu Leu Met Met Lys Pro Thr Val Val Ala Arg Pro
865                 870                 875                 880

Leu Leu Gly Thr Ile Leu Asn Leu Ala Arg Ala Ile Asp Phe Ile Tyr
                    885                 890                 895

Lys Glu Asp Asp Gly Tyr Thr His Ser Tyr Leu Ile Lys Asp Gln Ile
                    900                 905                 910

Ala Ser Val Leu Gly Asp His Val Pro Phe
                    915                 920

<210> SEQ ID NO 18
<211> LENGTH: 1773
<212> TYPE: DNA
<213> ORGANISM: Artificial
<220> FEATURE:
<223> OTHER INFORMATION: codon optimized ValC gene

<400> SEQUENCE: 18
atggccgaaa tgttcaatgg caattccagc aatgatggca gctcctgcat gccggtcaag      60
gacgcgctgc cgcaccgg gaaccaccat ccgaacctct ggaccgacga tttcatccag      120
tcgctgaact cccccctattc ggattcctcg tatcataaac atcgcgagat cctgatcgat      180
gagatccggg acatgttctc caacggcgag ggggatgagt tcggggtcct cgagaacatc      240
tggttcgtcg acgtggtcca gcggctgggc atcgatcggc acttccagga agagatcaag      300
acggccctgg attatatcta aagttctgg aaccatgata gcatcttcgg cgacctcaac      360
atggtggcgc tggggttccg catcctgcgg ctcaatcgct acgtggcgtc gtcggacgtg      420
ttcaagaagt tcaagggcga ggagggccag ttctcggggt tcgagagcag cgatcaggac      480
gccaagctgg agatgatgct gaacctctac aaggcctcgg aactcgactt cccggatgag      540
gacatcctca aggaagcgcg ggccttcgcg tcgatgtatc tcaagcatgt catcaaggag      600 tatgggggaca tccaggaatc gaagaacccc ctgctcatgg agatcgagta cacccttcaag      660 taccctggc gctgccgcct cccgcggctg gaggcgtgga acttcatcca catcatgcgg      720
cagcaggact gcaatatctc gctcgccaac aacctctata gatcccgaa gatctatatg      780 aagaagatcc tggagctggc gatcctcgac ttcaacatcc tccagagcca gcatcagcat      840
```

```
gagatgaaac tgatcagcac gtggtggaag aactcgtccg cgatccagct cgacttcttc      900
cgccaccgcc atatcgagag ctacttctgg tgggccagcc cgctgttcga gcccgagttc      960
tccacctgcc gcatcaactg caccaagctg tccaccaaga tgttcctcct ggacgacatc     1020
tatgacacgt acgggaccgt cgaggaactc aagccgttca cgaccaccct cacgcgctgg     1080
gatgtcagca cggtggacaa tcacccggac tacatgaaga tcgcgttcaa tttctcctac     1140
gagatctaca aggagatcgc gtccgaggcc gagcgcaagc acggcccgtt cgtgtataag     1200
tatctccagt cgtgctggaa gtcgtatatc gaggcgtata tgcaggaggc cgagtggatc     1260
gcctccaacc acatccccgg cttcgacgag tacctgatga atggcgtgaa gagctcgggg     1320
atgcgcatcc tcatgatcca tgcgctgatc ctgatggata cgcccctgtc cgacgagatc     1380
ctcgagcagc tcgacatccc gagcagcaag agccaggccc tgctgtcgct catcacgcgg     1440
ctcgtcgatg atgtgaagga tttcgaggac gagcaggcgc atggggagat ggcctcgtcg     1500
atcgaatgct atatgaagga taatcacggc tccacgcgcg aggacgccct gaactacctg     1560
aaaatccgca tcgagagctg cgtgcaggag ctcaacaagg aactcctcga accgagcaac     1620
atgcatggca gcttccgcaa cctgtacctc aacgtgggca tgcgggtgat cttcttcatg     1680
ctgaacgacg gggacctctt cacccattcg aatcggaagg agatccagga tgcgatcacg     1740
aagttcttcg tggaaccgat catcccgtga taa                                  1773

<210> SEQ ID NO 19
<211> LENGTH: 1725
<212> TYPE: DNA
<213> ORGANISM: Artificial
<220> FEATURE:
<223> OTHER INFORMATION: codon optimized ValC gene short

<400> SEQUENCE: 19
atgccggtca aggacgcgct gcgccgcacc gggaaccacc atccgaacct ctggaccgac       60
gatttcatcc agtcgctgaa ctcccccctat tcggattcct cgtatcataa acatcgcgag      120
atcctgatcg atgagatccg ggacatgttc tccaacggcg aggggggatga gttcggggtc      180 ctcgagaaca tctggttcgt cgacgtggtc cagcggctgg gcatcgatcg gcacttccag      240
gaagagatca agacggccct ggattatatc tataagttct ggaaccatga tagcatcttc      300
ggcgacctca catggtggc gctggggttc gcatcctgc ggctcaatcg ctacgtggcg        360
tcgtcggacg tgttcaagaa gttcaagggc gaggagggcc agttctcggg gttcgagagc      420
agcgatcagg acgccaagct ggagatgatg ctgaacctct acaaggcctc ggaactcgac      480
ttcccggatg aggacatcct caaggaagcg cgggccttcg cgtcgatgta tctcaagcat      540
gtcatcaagg agtatgggga catccaggaa tcgaagaacc ccctgctcat ggagatcgag      600
tacaccttca gtacccctg cgctgccgc ctcccgcggc tggaggcgtg aacttcatc         660 cacatcatgc ggcagcagga ctgcaatatc tcgctcgcca acaacctcta taagatcccg      720
aagatctata tgaagaagat cctggagctg gcgatcctcg acttcaacat cctccagagc      780
cagcatcagc atgagatgaa actgatcagc acgtggtgga agaactcgtc cgcgatccag      840
ctcgacttct tccgccaccg ccatatcgag agctacttct ggtgggccag cccgctgttc      900
gagcccgagt tctccacctg ccgcatcaac tgcaccaagc tgtccaccaa gatgttcctc      960
ctggacgaca tctatgacac gtacgggacc gtcgaggaac tcaagccgtt cacgaccacc     1020
ctcacgcgct gggatgtcag cacggtggac aatcacccgg actacatgaa gatcgcgttc     1080
aatttctcct acgagatcta caaggagatc gcgtccgagg ccgagcgcaa gcacggcccg     1140
```

-continued

```
ttcgtgtata agtatctcca gtcgtgctgg aagtcgtata tcgaggcgta tatgcaggag    1200
gccgagtgga tcgcctccaa ccacatcccc ggcttcgacg agtacctgat gaatggcgtg    1260
aagagctcgg ggatgcgcat cctcatgatc catgcgctga tcctgatgga tacgcccctg    1320
tccgacgaga tcctcgagca gctcgacatc ccgagcagca gagccaggc cctgctgtcg     1380 ctcatcacgc ggctcgtcga tgatgtgaag gatttcgagg acgagcaggc gcatggggag    1440
atggcctcgt cgatcgaatg ctatatgaag gataatcacg gctccacgcg cgaggacgcc    1500
ctgaactacc tgaaaatccg catcgagagc tgcgtgcagg agctcaacaa ggaactcctc    1560
gaaccgagca acatgcatgg cagcttccgc aacctgtacc tcaacgtggg catgcgggtg    1620
atcttcttca tgctgaacga cggggacctc ttcacccatt cgaatcggaa ggagatccag    1680
gatgcgatca cgaagttctt cgtggaaccg atcatcccgt gataa                    1725
```

<210> SEQ ID NO 20
<211> LENGTH: 2895
<212> TYPE: DNA
<213> ORGANISM: Artificial
<220> FEATURE:
<223> OTHER INFORMATION: synthetic fusion gene MBP-ValC
<220> FEATURE:
<221> NAME/KEY: CDS
<222> LOCATION: (1)..(2895)

<400> SEQUENCE: 20

```
atg aag atc gag gaa ggc aag ctc gtc atc tgg atc aac ggc gac aag      48
Met Lys Ile Glu Glu Gly Lys Leu Val Ile Trp Ile Asn Gly Asp Lys
1               5                   10                  15 ggc tac aac ggc ctc gcc gag gtg ggc aag aag ttc gag aag gac acg      96
Gly Tyr Asn Gly Leu Ala Glu Val Gly Lys Lys Phe Glu Lys Asp Thr
                20                  25                  30 ggc atc aag gtc acc gtc gag cat ccc gac aag ctc gag gag aag ttc     144
Gly Ile Lys Val Thr Val Glu His Pro Asp Lys Leu Glu Glu Lys Phe
            35                  40                  45 ccg cag gtc gcc gcc acc ggc gac ggc ccc gac atc atc ttc tgg gcc     192
Pro Gln Val Ala Ala Thr Gly Asp Gly Pro Asp Ile Ile Phe Trp Ala
        50                  55                  60 cac gac cgc ttc ggc ggc tat gcg cag tcg ggc ctg ctc gcc gag atc     240
His Asp Arg Phe Gly Gly Tyr Ala Gln Ser Gly Leu Leu Ala Glu Ile
65                  70                  75                  80 acg ccc gac aag gcc ttc cag gac aag ctc tat ccc ttc acc tgg gat     288
Thr Pro Asp Lys Ala Phe Gln Asp Lys Leu Tyr Pro Phe Thr Trp Asp
                85                  90                  95 gcg gtg cgc tac aac ggc aag ctg atc gcc tat ccg atc gcc gtc gag     336
Ala Val Arg Tyr Asn Gly Lys Leu Ile Ala Tyr Pro Ile Ala Val Glu
                100                 105                 110 gcg ctg tcg ctg atc tac aac aag gat ctg ctg ccg aac ccg ccg aag     384
Ala Leu Ser Leu Ile Tyr Asn Lys Asp Leu Leu Pro Asn Pro Pro Lys
            115                 120                 125 acc tgg gaa gag atc ccg gcg ctc gac aag gaa ctg aag gcc aag ggc     432
Thr Trp Glu Glu Ile Pro Ala Leu Asp Lys Glu Leu Lys Ala Lys Gly
        130                 135                 140 aag tcc gcg ctg atg ttc aac ctg cag gag ccc tat ttc acc tgg ccg     480
Lys Ser Ala Leu Met Phe Asn Leu Gln Glu Pro Tyr Phe Thr Trp Pro
145                 150                 155                 160 ctg atc gcc gcc gac ggc ggc tat gcc ttc aaa tac gag aac ggc aaa     528
Leu Ile Ala Ala Asp Gly Gly Tyr Ala Phe Lys Tyr Glu Asn Gly Lys
                165                 170                 175 tac gac atc aag gac gtg ggc gtc gac aat gcg ggc gcc aag gcc ggg     576
Tyr Asp Ile Lys Asp Val Gly Val Asp Asn Ala Gly Ala Lys Ala Gly
```

```
                 Tyr Asp Ile Lys Asp Val Gly Val Asp Asn Ala Gly Ala Lys Ala Gly
                                 180                 185                 190 ctg acc ttc ctc gtc gat ctg atc aag aac aag cac atg aat gcc gac              624
Leu Thr Phe Leu Val Asp Leu Ile Lys Asn Lys His Met Asn Ala Asp
            195                 200                 205 acc gac tat tcc atc gcc gag gcg gcc ttc aac aag ggc gag acc gcc              672
Thr Asp Tyr Ser Ile Ala Glu Ala Ala Phe Asn Lys Gly Glu Thr Ala
210                 215                 220 atg acg atc aac ggg ccg tgg gcc tgg tcg aac atc gac acc tcg aag              720
Met Thr Ile Asn Gly Pro Trp Ala Trp Ser Asn Ile Asp Thr Ser Lys
225                 230                 235                 240 gtc aat tac ggc gtc acg gtg ctg ccg acc ttc aag ggc cag ccc tcg              768
Val Asn Tyr Gly Val Thr Val Leu Pro Thr Phe Lys Gly Gln Pro Ser
            245                 250                 255 aaa ccc ttc gtc ggc gtg ctg tcg gcg ggc atc aac gcg gcc tcg ccg              816
Lys Pro Phe Val Gly Val Leu Ser Ala Gly Ile Asn Ala Ala Ser Pro
            260                 265                 270 aac aag gaa ctc gcc aag gag ttc ctc gag aac tac ctg ctg acc gac              864
Asn Lys Glu Leu Ala Lys Glu Phe Leu Glu Asn Tyr Leu Leu Thr Asp
            275                 280                 285 gag ggg ctc gag gcg gtg aac aag gac aag ccg ctc ggc gcg gtg gcg              912
Glu Gly Leu Glu Ala Val Asn Lys Asp Lys Pro Leu Gly Ala Val Ala
            290                 295                 300 ctg aaa tcc tac gag gaa gag ctc gtc aag gac ccg cgg atc gcc gcc              960
Leu Lys Ser Tyr Glu Glu Glu Leu Val Lys Asp Pro Arg Ile Ala Ala
305                 310                 315                 320 acg atg gag aat gcg cag aag ggc gag atc atg ccg aac atc ccg cag             1008
Thr Met Glu Asn Ala Gln Lys Gly Glu Ile Met Pro Asn Ile Pro Gln
                325                 330                 335 atg tcg gcc ttc tgg tat gcc gtc cgc acc gcg gtg atc aac gcg gcc             1056
Met Ser Ala Phe Trp Tyr Ala Val Arg Thr Ala Val Ile Asn Ala Ala
            340                 345                 350 tcg ggc cgt cag acc gtc gac gag gcg ctg aag gat gcg cag act ggt             1104
Ser Gly Arg Gln Thr Val Asp Glu Ala Leu Lys Asp Ala Gln Thr Gly
            355                 360                 365 gat gac gac gac aag att atg gcc gaa atg ttc aat ggc aat tcc agc             1152
Asp Asp Asp Asp Lys Ile Met Ala Glu Met Phe Asn Gly Asn Ser Ser
370                 375                 380 aat gat ggc agc tcc tgc atg ccg gtc aag gac gcg ctg cgc cgc acc             1200
Asn Asp Gly Ser Ser Cys Met Pro Val Lys Asp Ala Leu Arg Arg Thr
385                 390                 395                 400 ggg aac cac cat ccg aac ctc tgg acc gac gat ttc atc cag tcg ctg             1248
Gly Asn His His Pro Asn Leu Trp Thr Asp Asp Phe Ile Gln Ser Leu
                405                 410                 415 aac tcc ccc tat tcg gat tcc tcg tat cat aaa cat cgc gag atc ctg             1296
Asn Ser Pro Tyr Ser Asp Ser Ser Tyr His Lys His Arg Glu Ile Leu
            420                 425                 430 atc gat gag atc cgg gac atg ttc tcc aac ggc gag ggg gat gag ttc             1344
Ile Asp Glu Ile Arg Asp Met Phe Ser Asn Gly Glu Gly Asp Glu Phe
            435                 440                 445 ggg gtc ctc gag aac atc tgg ttc gtc gac gtg gtc cag cgg ctg ggc             1392
Gly Val Leu Glu Asn Ile Trp Phe Val Asp Val Val Gln Arg Leu Gly
            450                 455                 460 atc gat cgg cac ttc cag gaa gag atc aag acg gcc ctg gat tat atc             1440
Ile Asp Arg His Phe Gln Glu Glu Ile Lys Thr Ala Leu Asp Tyr Ile
465                 470                 475                 480 tat aag ttc tgg aac cat gat agc atc ttc ggc gac ctc aac atg gtg             1488
Tyr Lys Phe Trp Asn His Asp Ser Ile Phe Gly Asp Leu Asn Met Val
                485                 490                 495
```

```
                                      -continued gcg ctg ggg ttc cgc atc ctg cgg ctc aat cgc tac gtg gcg tcg tcg    1536
Ala Leu Gly Phe Arg Ile Leu Arg Leu Asn Arg Tyr Val Ala Ser Ser
500                 505                 510 gac gtg ttc aag aag ttc aag ggc gag gag ggc cag ttc tcg ggg ttc    1584
Asp Val Phe Lys Lys Phe Lys Gly Glu Glu Gly Gln Phe Ser Gly Phe
        515                 520                 525 gag agc agc gat cag gac gcc aag ctg gag atg atg ctg aac ctc tac    1632
Glu Ser Ser Asp Gln Asp Ala Lys Leu Glu Met Met Leu Asn Leu Tyr
530                 535                 540 aag gcc tcg gaa ctc gac ttc ccg gat gag gac atc ctc aag gaa gcg    1680
Lys Ala Ser Glu Leu Asp Phe Pro Asp Glu Asp Ile Leu Lys Glu Ala
545                 550                 555                 560 cgg gcc ttc gcg tcg atg tat ctc aag cat gtc atc aag gag tat ggg    1728
Arg Ala Phe Ala Ser Met Tyr Leu Lys His Val Ile Lys Glu Tyr Gly
            565                 570                 575 gac atc cag gaa tcg aag aac ccc ctg ctc atg gag atc gag tac acc    1776
Asp Ile Gln Glu Ser Lys Asn Pro Leu Leu Met Glu Ile Glu Tyr Thr
        580                 585                 590 ttc aag tac ccc tgg cgc tgc cgc ctc ccg cgg ctg gag gcg tgg aac    1824
Phe Lys Tyr Pro Trp Arg Cys Arg Leu Pro Arg Leu Glu Ala Trp Asn
595                 600                 605 ttc atc cac atc atg cgg cag cag gac tgc aat atc tcg ctc gcc aac    1872
Phe Ile His Ile Met Arg Gln Gln Asp Cys Asn Ile Ser Leu Ala Asn
610                 615                 620 aac ctc tat aag atc ccg aag atc tat atg aag aag atc ctg gag ctg    1920
Asn Leu Tyr Lys Ile Pro Lys Ile Tyr Met Lys Lys Ile Leu Glu Leu
625                 630                 635                 640 gcg atc ctc gac ttc aac atc ctc cag agc cag cat cag cat gag atg    1968
Ala Ile Leu Asp Phe Asn Ile Leu Gln Ser Gln His Gln His Glu Met
            645                 650                 655 aaa ctg atc agc acg tgg tgg aag aac tcg tcc gcg atc cag ctc gac    2016
Lys Leu Ile Ser Thr Trp Trp Lys Asn Ser Ser Ala Ile Gln Leu Asp
        660                 665                 670 ttc ttc cgc cac cgc cat atc gag agc tac ttc tgg tgg gcc agc ccg    2064
Phe Phe Arg His Arg His Ile Glu Ser Tyr Phe Trp Trp Ala Ser Pro
675                 680                 685 ctg ttc gag ccc gag ttc tcc acc tgc cgc atc aac tgc acc aag ctg    2112
Leu Phe Glu Pro Glu Phe Ser Thr Cys Arg Ile Asn Cys Thr Lys Leu
690                 695                 700 tcc acc aag atg ttc ctc ctg gac gac atc tat gac acg tac ggg acc    2160
Ser Thr Lys Met Phe Leu Leu Asp Asp Ile Tyr Asp Thr Tyr Gly Thr
705                 710                 715                 720 gtc gag gaa ctc aag ccg ttc acg acc acc ctc acg cgc tgg gat gtc    2208
Val Glu Glu Leu Lys Pro Phe Thr Thr Thr Leu Thr Arg Trp Asp Val
            725                 730                 735 agc acg gtg gac aat cac ccg gac tac atg aag atc gcg ttc aat ttc    2256
Ser Thr Val Asp Asn His Pro Asp Tyr Met Lys Ile Ala Phe Asn Phe
        740                 745                 750 tcc tac gag atc tac aag gag atc gcg tcc gag gcc gag cgc aag cac    2304
Ser Tyr Glu Ile Tyr Lys Glu Ile Ala Ser Glu Ala Glu Arg Lys His
755                 760                 765 ggc ccg ttc gtg tat aag tat ctc cag tcg tgc tgg aag tcg tat atc    2352
Gly Pro Phe Val Tyr Lys Tyr Leu Gln Ser Cys Trp Lys Ser Tyr Ile
770                 775                 780 gag gcg tat atg cag gag gcc gag tgg atc gcc tcc aac cac atc ccc    2400
Glu Ala Tyr Met Gln Glu Ala Glu Trp Ile Ala Ser Asn His Ile Pro
785                 790                 795                 800 ggc ttc gac gag tac ctg atg aat ggc gtg aag agc tcg ggg atg cgc    2448
Gly Phe Asp Glu Tyr Leu Met Asn Gly Val Lys Ser Ser Gly Met Arg
            805                 810                 815
```

```
atc ctc atg atc cat gcg ctg atc ctg atg gat acg ccc ctg tcc gac    2496
Ile Leu Met Ile His Ala Leu Ile Leu Met Asp Thr Pro Leu Ser Asp
            820                 825                 830 gag atc ctc gag cag ctc gac atc ccg agc agc aag agc cag gcc ctg    2544
Glu Ile Leu Glu Gln Leu Asp Ile Pro Ser Ser Lys Ser Gln Ala Leu
        835                 840                 845 ctg tcg ctc atc acg cgg ctc gtc gat gat gtg aag gat ttc gag gac    2592
Leu Ser Leu Ile Thr Arg Leu Val Asp Asp Val Lys Asp Phe Glu Asp
    850                 855                 860 gag cag gcg cat ggg gag atg gcc tcg tcg atc gaa tgc tat atg aag    2640
Glu Gln Ala His Gly Glu Met Ala Ser Ser Ile Glu Cys Tyr Met Lys
865                 870                 875                 880 gat aat cac ggc tcc acg cgc gag gac gcc ctg aac tac ctg aaa atc    2688
Asp Asn His Gly Ser Thr Arg Glu Asp Ala Leu Asn Tyr Leu Lys Ile
                885                 890                 895 cgc atc gag agc tgc gtg cag gag ctc aac aag gaa ctc ctc gaa ccg    2736
Arg Ile Glu Ser Cys Val Gln Glu Leu Asn Lys Glu Leu Leu Glu Pro
            900                 905                 910 agc aac atg cat ggc agc ttc cgc aac ctg tac ctc aac gtg ggc atg    2784
Ser Asn Met His Gly Ser Phe Arg Asn Leu Tyr Leu Asn Val Gly Met
        915                 920                 925 cgg gtg atc ttc ttc atg ctg aac gac ggg gac ctc ttc acc cat tcg    2832
Arg Val Ile Phe Phe Met Leu Asn Asp Gly Asp Leu Phe Thr His Ser
    930                 935                 940 aat cgg aag gag atc cag gat gcg atc acg aag ttc ttc gtg gaa ccg    2880
Asn Arg Lys Glu Ile Gln Asp Ala Ile Thr Lys Phe Phe Val Glu Pro
945                 950                 955                 960 atc atc ccg tga taa                                                 2895
Ile Ile Pro <210> SEQ ID NO 21
<211> LENGTH: 963
<212> TYPE: PRT
<213> ORGANISM: Artificial
<220> FEATURE:
<223> OTHER INFORMATION: Synthetic Construct

<400> SEQUENCE: 21

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160
```

```
Leu Ile Ala Ala Asp Gly Gly Tyr Ala Phe Lys Tyr Glu Asn Gly Lys
                165                 170                 175
Tyr Asp Ile Lys Asp Val Gly Val Asp Asn Ala Gly Ala Lys Ala Gly
                180                 185                 190
Leu Thr Phe Leu Val Asp Leu Ile Lys Asn Lys His Met Asn Ala Asp
                195                 200                 205
Thr Asp Tyr Ser Ile Ala Glu Ala Ala Phe Asn Lys Gly Glu Thr Ala
                210                 215                 220
Met Thr Ile Asn Gly Pro Trp Ala Trp Ser Asn Ile Asp Thr Ser Lys
225                 230                 235                 240
Val Asn Tyr Gly Val Thr Val Leu Pro Thr Phe Lys Gly Gln Pro Ser
                245                 250                 255
Lys Pro Phe Val Gly Val Leu Ser Ala Gly Ile Asn Ala Ala Ser Pro
                260                 265                 270
Asn Lys Glu Leu Ala Lys Glu Phe Leu Glu Asn Tyr Leu Leu Thr Asp
                275                 280                 285
Glu Gly Leu Glu Ala Val Asn Lys Asp Lys Pro Leu Gly Ala Val Ala
                290                 295                 300
Leu Lys Ser Tyr Glu Glu Leu Val Lys Asp Pro Arg Ile Ala Ala
305                 310                 315                 320
Thr Met Glu Asn Ala Gln Lys Gly Glu Ile Met Pro Asn Ile Pro Gln
                325                 330                 335
Met Ser Ala Phe Trp Tyr Ala Val Arg Thr Ala Val Ile Asn Ala Ala
                340                 345                 350
Ser Gly Arg Gln Thr Val Asp Glu Ala Leu Lys Asp Ala Gln Thr Gly
                355                 360                 365
Asp Asp Asp Asp Lys Ile Met Ala Glu Met Phe Asn Gly Asn Ser Ser
                370                 375                 380
Asn Asp Gly Ser Ser Cys Met Pro Val Lys Asp Ala Leu Arg Arg Thr
385                 390                 395                 400
Gly Asn His His Pro Asn Leu Trp Thr Asp Asp Phe Ile Gln Ser Leu
                405                 410                 415
Asn Ser Pro Tyr Ser Asp Ser Ser Tyr His Lys His Arg Glu Ile Leu
                420                 425                 430
Ile Asp Glu Ile Arg Asp Met Phe Ser Asn Gly Glu Gly Asp Glu Phe
                435                 440                 445
Gly Val Leu Glu Asn Ile Trp Phe Val Asp Val Val Gln Arg Leu Gly
                450                 455                 460
Ile Asp Arg His Phe Gln Glu Glu Ile Lys Thr Ala Leu Asp Tyr Ile
465                 470                 475                 480
Tyr Lys Phe Trp Asn His Asp Ser Ile Phe Gly Asp Leu Asn Met Val
                485                 490                 495
Ala Leu Gly Phe Arg Ile Leu Arg Leu Asn Arg Tyr Val Ala Ser Ser
                500                 505                 510
Asp Val Phe Lys Lys Phe Lys Gly Glu Glu Gly Gln Phe Ser Gly Phe
                515                 520                 525
Glu Ser Ser Asp Gln Asp Ala Lys Leu Glu Met Met Leu Asn Leu Tyr
                530                 535                 540
Lys Ala Ser Glu Leu Asp Phe Pro Asp Glu Asp Ile Leu Lys Glu Ala
545                 550                 555                 560
Arg Ala Phe Ala Ser Met Tyr Leu Lys His Val Ile Lys Glu Tyr Gly
                565                 570                 575
```

```
Asp Ile Gln Glu Ser Lys Asn Pro Leu Leu Met Glu Ile Glu Tyr Thr
                580                 585                 590
Phe Lys Tyr Pro Trp Arg Cys Arg Leu Pro Arg Leu Glu Ala Trp Asn
            595                 600                 605
Phe Ile His Ile Met Arg Gln Gln Asp Cys Asn Ile Ser Leu Ala Asn
610                 615                 620
Asn Leu Tyr Lys Ile Pro Lys Ile Tyr Met Lys Lys Ile Leu Glu Leu
625                 630                 635                 640
Ala Ile Leu Asp Phe Asn Ile Leu Gln Ser Gln His Gln His Glu Met
                645                 650                 655
Lys Leu Ile Ser Thr Trp Trp Lys Asn Ser Ser Ala Ile Gln Leu Asp
            660                 665                 670
Phe Phe Arg His Arg His Ile Glu Ser Tyr Phe Trp Trp Ala Ser Pro
        675                 680                 685
Leu Phe Glu Pro Glu Phe Ser Thr Cys Arg Ile Asn Cys Thr Lys Leu
    690                 695                 700
Ser Thr Lys Met Phe Leu Leu Asp Asp Ile Tyr Asp Thr Tyr Gly Thr
705                 710                 715                 720
Val Glu Glu Leu Lys Pro Phe Thr Thr Thr Leu Thr Arg Trp Asp Val
                725                 730                 735
Ser Thr Val Asp Asn His Pro Asp Tyr Met Lys Ile Ala Phe Asn Phe
            740                 745                 750
Ser Tyr Glu Ile Tyr Lys Glu Ile Ala Ser Glu Ala Glu Arg Lys His
        755                 760                 765
Gly Pro Phe Val Tyr Lys Tyr Leu Gln Ser Cys Trp Lys Ser Tyr Ile
    770                 775                 780
Glu Ala Tyr Met Gln Glu Ala Glu Trp Ile Ala Ser Asn His Ile Pro
785                 790                 795                 800
Gly Phe Asp Glu Tyr Leu Met Asn Gly Val Lys Ser Ser Gly Met Arg
                805                 810                 815
Ile Leu Met Ile His Ala Leu Ile Leu Met Asp Thr Pro Leu Ser Asp
            820                 825                 830
Glu Ile Leu Glu Gln Leu Asp Ile Pro Ser Ser Lys Ser Gln Ala Leu
        835                 840                 845
Leu Ser Leu Ile Thr Arg Leu Val Asp Asp Val Lys Asp Phe Glu Asp
    850                 855                 860
Glu Gln Ala His Gly Glu Met Ala Ser Ser Ile Glu Cys Tyr Met Lys
865                 870                 875                 880
Asp Asn His Gly Ser Thr Arg Glu Asp Ala Leu Asn Tyr Leu Lys Ile
                885                 890                 895
Arg Ile Glu Ser Cys Val Gln Glu Leu Asn Lys Glu Leu Leu Glu Pro
            900                 905                 910
Ser Asn Met His Gly Ser Phe Arg Asn Leu Tyr Leu Asn Val Gly Met
        915                 920                 925
Arg Val Ile Phe Phe Met Leu Asn Asp Gly Asp Leu Phe Thr His Ser
    930                 935                 940
Asn Arg Lys Glu Ile Gln Asp Ala Ile Thr Lys Phe Phe Val Glu Pro
945                 950                 955                 960
Ile Ile Pro

<210> SEQ ID NO 22
<211> LENGTH: 2847
<212> TYPE: DNA
<213> ORGANISM: Artificial
```

```
<220> FEATURE:
<223> OTHER INFORMATION: synthetic fusion gene MBP - ValC short
<220> FEATURE:
<221> NAME/KEY: CDS
<222> LOCATION: (1)..(2847)

<400> SEQUENCE: 22 atg aag atc gag gaa ggc aag ctc gtc atc tgg atc aac ggc gac aag    48
Met Lys Ile Glu Glu Gly Lys Leu Val Ile Trp Ile Asn Gly Asp Lys
1               5                   10                  15 ggc tac aac ggc ctc gcc gag gtg ggc aag aag ttc gag aag gac acg    96
Gly Tyr Asn Gly Leu Ala Glu Val Gly Lys Lys Phe Glu Lys Asp Thr
                20                  25                  30 ggc atc aag gtc acc gtc gag cat ccc gac aag ctc gag gag aag ttc   144
Gly Ile Lys Val Thr Val Glu His Pro Asp Lys Leu Glu Glu Lys Phe
            35                  40                  45 ccg cag gtc gcc gcc acc ggc gac ggc ccc gac atc atc ttc tgg gcc   192
Pro Gln Val Ala Ala Thr Gly Asp Gly Pro Asp Ile Ile Phe Trp Ala
        50                  55                  60 cac gac cgc ttc ggc ggc tat gcg cag tcg ggc ctg ctc gcc gag atc   240
His Asp Arg Phe Gly Gly Tyr Ala Gln Ser Gly Leu Leu Ala Glu Ile
65                  70                  75                  80 acg ccc gac aag gcc ttc cag gac aag ctc tat ccc ttc acc tgg gat   288
Thr Pro Asp Lys Ala Phe Gln Asp Lys Leu Tyr Pro Phe Thr Trp Asp
                85                  90                  95 gcg gtg cgc tac aac ggc aag ctg atc gcc tat ccg atc gcc gtc gag   336
Ala Val Arg Tyr Asn Gly Lys Leu Ile Ala Tyr Pro Ile Ala Val Glu
                100                 105                 110 gcg ctg tcg ctg atc tac aac aag gat ctg ctg ccg aac ccg ccg aag   384
Ala Leu Ser Leu Ile Tyr Asn Lys Asp Leu Leu Pro Asn Pro Pro Lys
            115                 120                 125 acc tgg gaa gag atc ccg gcg ctc gac aag gaa ctg aag gcc aag ggc   432
Thr Trp Glu Glu Ile Pro Ala Leu Asp Lys Glu Leu Lys Ala Lys Gly
        130                 135                 140 aag tcc gcg ctg atg ttc aac ctg cag gag ccc tat ttc acc tgg ccg   480
Lys Ser Ala Leu Met Phe Asn Leu Gln Glu Pro Tyr Phe Thr Trp Pro
145                 150                 155                 160 ctg atc gcc gcc gac ggc ggc tat gcc ttc aaa tac gag aac ggc aaa   528
Leu Ile Ala Ala Asp Gly Gly Tyr Ala Phe Lys Tyr Glu Asn Gly Lys
                165                 170                 175 tac gac atc aag gac gtg ggc gtc gac aat gcg ggc gcc aag gcc ggg   576
Tyr Asp Ile Lys Asp Val Gly Val Asp Asn Ala Gly Ala Lys Ala Gly
                180                 185                 190 ctg acc ttc ctc gtc gat ctg atc aag aac aag cac atg aat gcc gac   624
Leu Thr Phe Leu Val Asp Leu Ile Lys Asn Lys His Met Asn Ala Asp
            195                 200                 205 acc gac tat tcc atc gcc gag gcg gcc ttc aac aag ggc gag acc gcc   672
Thr Asp Tyr Ser Ile Ala Glu Ala Ala Phe Asn Lys Gly Glu Thr Ala
        210                 215                 220 atg acg atc aac ggg ccg tgg gcc tgg tcg aac atc gac acc tcg aag   720
Met Thr Ile Asn Gly Pro Trp Ala Trp Ser Asn Ile Asp Thr Ser Lys
225                 230                 235                 240 gtc aat tac ggc gtc acg gtg ctg ccg acc ttc aag ggc cag ccc tcg   768
Val Asn Tyr Gly Val Thr Val Leu Pro Thr Phe Lys Gly Gln Pro Ser
                245                 250                 255 aaa ccc ttc gtc ggc gtg ctg tcg gcg ggc atc aac gcg gcc tcg ccg   816
Lys Pro Phe Val Gly Val Leu Ser Ala Gly Ile Asn Ala Ala Ser Pro
                260                 265                 270 aac aag gaa ctc gcc aag gag ttc ctc gag aac tac ctg ctg acc gac   864
Asn Lys Glu Leu Ala Lys Glu Phe Leu Glu Asn Tyr Leu Leu Thr Asp
            275                 280                 285
```

-continued

| | | |
|---|---|---|
| gag ggg ctc gag gcg gtg aac aag gac aag ccg ctc ggc gcg gtg gcg<br>Glu Gly Leu Glu Ala Val Asn Lys Asp Lys Pro Leu Gly Ala Val Ala<br>290                         295                        300 | 912 | |
| ctg aaa tcc tac gag gaa gag ctc gtc aag gac ccg cgg atc gcc gcc<br>Leu Lys Ser Tyr Glu Glu Glu Leu Val Lys Asp Pro Arg Ile Ala Ala<br>305                        310                        315                  320 | 960 | |
| acg atg gag aat gcg cag aag ggc gag atc atg ccg aac atc ccg cag<br>Thr Met Glu Asn Ala Gln Lys Gly Glu Ile Met Pro Asn Ile Pro Gln<br>                        325                        330                        335 | 1008 | |
| atg tcg gcc ttc tgg tat gcc gtc cgc acc gcg gtg atc aac gcg gcc<br>Met Ser Ala Phe Trp Tyr Ala Val Arg Thr Ala Val Ile Asn Ala Ala<br>                        340                        345                        350 | 1056 | |
| tcg ggc cgt cag acc gtc gac gag gcg ctg aag gat gcg cag act ggt<br>Ser Gly Arg Gln Thr Val Asp Glu Ala Leu Lys Asp Ala Gln Thr Gly<br>                355                        360                        365 | 1104 | |
| gat gac gac gac aag att atg ccg gtc aag gac gcg ctg cgc cgc acc<br>Asp Asp Asp Asp Lys Ile Met Pro Val Lys Asp Ala Leu Arg Arg Thr<br>370                          375                        380 | 1152 | |
| ggg aac cac cat ccg aac ctc tgg acc gac gat ttc atc cag tcg ctg<br>Gly Asn His His Pro Asn Leu Trp Thr Asp Asp Phe Ile Gln Ser Leu<br>385                          390                        395                  400 | 1200 | |
| aac tcc ccc tat tcg gat tcc tcg tat cat aaa cat cgc gag atc ctg<br>Asn Ser Pro Tyr Ser Asp Ser Ser Tyr His Lys His Arg Glu Ile Leu<br>                        405                        410                        415 | 1248 | |
| atc gat gag atc cgg gac atg ttc tcc aac ggc gag ggg gat gag ttc<br>Ile Asp Glu Ile Arg Asp Met Phe Ser Asn Gly Glu Gly Asp Glu Phe<br>                      420                        425                        430 | 1296 | |
| ggg gtc ctc gag aac atc tgg ttc gtc gac gtg gtc cag cgg ctg ggc<br>Gly Val Leu Glu Asn Ile Trp Phe Val Asp Val Val Gln Arg Leu Gly<br>                435                        440                        445 | 1344 | |
| atc gat cgg cac ttc cag gaa gag atc aag acg gcc ctg gat tat atc<br>Ile Asp Arg His Phe Gln Glu Glu Ile Lys Thr Ala Leu Asp Tyr Ile<br>450                          455                        460 | 1392 | |
| tat aag ttc tgg aac cat gat agc atc ttc ggc gac ctc aac atg gtg<br>Tyr Lys Phe Trp Asn His Asp Ser Ile Phe Gly Asp Leu Asn Met Val<br>465                          470                        475                  480 | 1440 | |
| gcg ctg ggg ttc cgc atc ctg cgg ctc aat cgc tac gtg gcg tcg tcg<br>Ala Leu Gly Phe Arg Ile Leu Arg Leu Asn Arg Tyr Val Ala Ser Ser<br>                        485                        490                        495 | 1488 | |
| gac gtg ttc aag aag ttc aag ggc gag gag ggc cag ttc tcg ggg ttc<br>Asp Val Phe Lys Lys Phe Lys Gly Glu Glu Gly Gln Phe Ser Gly Phe<br>                      500                        505                        510 | 1536 | |
| gag agc agc gat cag gac gcc aag ctg gag atg atg ctg aac ctc tac<br>Glu Ser Ser Asp Gln Asp Ala Lys Leu Glu Met Met Leu Asn Leu Tyr<br>                515                        520                        525 | 1584 | |
| aag gcc tcg gaa ctc gac ttc ccg gat gag gac atc ctc aag gaa gcg<br>Lys Ala Ser Glu Leu Asp Phe Pro Asp Glu Asp Ile Leu Lys Glu Ala<br>530                          535                        540 | 1632 | |
| cgg gcc ttc gcg tcg atg tat ctc aag cat gtc atc aag gag tat ggg<br>Arg Ala Phe Ala Ser Met Tyr Leu Lys His Val Ile Lys Glu Tyr Gly<br>545                          550                        555                  560 | 1680 | |
| gac atc cag gaa tcg aag aac ccc ctg ctc atg gag atc gag tac acc<br>Asp Ile Gln Glu Ser Lys Asn Pro Leu Leu Met Glu Ile Glu Tyr Thr<br>                        565                        570                        575 | 1728 | |
| ttc aag tac ccc tgg cgc tgc cgc ctc ccg cgg ctg gag gcg tgg aac<br>Phe Lys Tyr Pro Trp Arg Cys Arg Leu Pro Arg Leu Glu Ala Trp Asn<br>                      580                        585                        590 | 1776 | |
| ttc atc cac atc atg cgg cag cag gac tgc aat atc tcg ctc gcc aac<br>Phe Ile His Ile Met Arg Gln Gln Asp Cys Asn Ile Ser Leu Ala Asn | 1824 | |

-continued

```
            595                 600                 605
aac ctc tat aag atc ccg aag atc tat atg aag aag atc ctg gag ctg    1872
Asn Leu Tyr Lys Ile Pro Lys Ile Tyr Met Lys Lys Ile Leu Glu Leu
    610                 615                 620 gcg atc ctc gac ttc aac atc ctc cag agc cag cat cag cat gag atg    1920
Ala Ile Leu Asp Phe Asn Ile Leu Gln Ser Gln His Gln His Glu Met
625                 630                 635                 640 aaa ctg atc agc acg tgg tgg aag aac tcg tcc gcg atc cag ctc gac    1968
Lys Leu Ile Ser Thr Trp Trp Lys Asn Ser Ser Ala Ile Gln Leu Asp
            645                 650                 655 ttc ttc cgc cac cgc cat atc gag agc tac ttc tgg tgg gcc agc ccg    2016
Phe Phe Arg His Arg His Ile Glu Ser Tyr Phe Trp Trp Ala Ser Pro
        660                 665                 670 ctg ttc gag ccc gag ttc tcc acc tgc cgc atc aac tgc acc aag ctg    2064
Leu Phe Glu Pro Glu Phe Ser Thr Cys Arg Ile Asn Cys Thr Lys Leu
    675                 680                 685 tcc acc aag atg ttc ctc ctg gac gac atc tat gac acg tac ggg acc    2112
Ser Thr Lys Met Phe Leu Leu Asp Asp Ile Tyr Asp Thr Tyr Gly Thr
690                 695                 700 gtc gag gaa ctc aag ccg ttc acg acc acc ctc acg cgc tgg gat gtc    2160
Val Glu Glu Leu Lys Pro Phe Thr Thr Thr Leu Thr Arg Trp Asp Val
705                 710                 715                 720 agc acg gtg gac aat cac ccg gac tac atg aag atc gcg ttc aat ttc    2208
Ser Thr Val Asp Asn His Pro Asp Tyr Met Lys Ile Ala Phe Asn Phe
            725                 730                 735 tcc tac gag atc tac aag gag atc gcg tcc gag gcc gag cgc aag cac    2256
Ser Tyr Glu Ile Tyr Lys Glu Ile Ala Ser Glu Ala Glu Arg Lys His
        740                 745                 750 ggc ccg ttc gtg tat aag tat ctc cag tcg tgc tgg aag tcg tat atc    2304
Gly Pro Phe Val Tyr Lys Tyr Leu Gln Ser Cys Trp Lys Ser Tyr Ile
    755                 760                 765 gag gcg tat atg cag gag gcc gag tgg atc gcc tcc aac cac atc ccc    2352
Glu Ala Tyr Met Gln Glu Ala Glu Trp Ile Ala Ser Asn His Ile Pro
770                 775                 780 ggc ttc gac gag tac ctg atg aat ggc gtg aag agc tcg ggg atg cgc    2400
Gly Phe Asp Glu Tyr Leu Met Asn Gly Val Lys Ser Ser Gly Met Arg
785                 790                 795                 800 atc ctc atg atc cat gcg ctg atc ctg atg gat acg ccc ctg tcc gac    2448
Ile Leu Met Ile His Ala Leu Ile Leu Met Asp Thr Pro Leu Ser Asp
            805                 810                 815 gag atc ctc gag cag ctc gac atc ccg agc agc aag agc cag gcc ctg    2496
Glu Ile Leu Glu Gln Leu Asp Ile Pro Ser Ser Lys Ser Gln Ala Leu
        820                 825                 830 ctg tcg ctc atc acg cgg ctc gtc gat gat gtg aag gat ttc gag gac    2544
Leu Ser Leu Ile Thr Arg Leu Val Asp Asp Val Lys Asp Phe Glu Asp
    835                 840                 845 gag cag gcg cat ggg gag atg gcc tcg tcg atc gaa tgc tat atg aag    2592
Glu Gln Ala His Gly Glu Met Ala Ser Ser Ile Glu Cys Tyr Met Lys
850                 855                 860 gat aat cac ggc tcc acg cgc gag gac gcc ctg aac tac ctg aaa atc    2640
Asp Asn His Gly Ser Thr Arg Glu Asp Ala Leu Asn Tyr Leu Lys Ile
865                 870                 875                 880 cgc atc gag agc tgc gtg cag gag ctc aac aag gaa ctc ctc gaa ccg    2688
Arg Ile Glu Ser Cys Val Gln Glu Leu Asn Lys Glu Leu Leu Glu Pro
            885                 890                 895 agc aac atg cat ggc agc ttc cgc aac ctg tac ctc aac gtg ggc atg    2736
Ser Asn Met His Gly Ser Phe Arg Asn Leu Tyr Leu Asn Val Gly Met
        900                 905                 910 cgg gtg atc ttc ttc atg ctg aac gac ggg gac ctc ttc acc cat tcg    2784
```

-continued

```
Arg Val Ile Phe Phe Met Leu Asn Asp Gly Asp Leu Phe Thr His Ser
            915                 920                 925 aat cgg aag gag atc cag gat gcg atc acg aag ttc ttc gtg gaa ccg    2832
Asn Arg Lys Glu Ile Gln Asp Ala Ile Thr Lys Phe Phe Val Glu Pro
            930                 935                 940 atc atc ccg tga taa                                                 2847
Ile Ile Pro
945

<210> SEQ ID NO 23
<211> LENGTH: 947
<212> TYPE: PRT
<213> ORGANISM: Artificial
<220> FEATURE:
<223> OTHER INFORMATION: Synthetic Construct

<400> SEQUENCE: 23

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Glu Leu Val Lys Asp Pro Arg Ile Ala Ala
```

```
                305                 310                 315                 320
Thr Met Glu Asn Ala Gln Lys Gly Glu Ile Met Pro Asn Ile Pro Gln
                    325                 330                 335
Met Ser Ala Phe Trp Tyr Ala Val Arg Thr Ala Val Ile Asn Ala Ala
                    340                 345                 350
Ser Gly Arg Gln Thr Val Asp Glu Ala Leu Lys Asp Ala Gln Thr Gly
                    355                 360                 365
Asp Asp Asp Lys Ile Met Pro Val Lys Asp Ala Leu Arg Arg Thr
                    370                 375                 380
Gly Asn His His Pro Asn Leu Trp Thr Asp Asp Phe Ile Gln Ser Leu
385                 390                 395                 400
Asn Ser Pro Tyr Ser Asp Ser Tyr His Lys His Arg Glu Ile Leu
                    405                 410                 415
Ile Asp Glu Ile Arg Asp Met Phe Ser Asn Gly Glu Gly Asp Glu Phe
                    420                 425                 430
Gly Val Leu Glu Asn Ile Trp Phe Val Asp Val Val Gln Arg Leu Gly
                    435                 440                 445
Ile Asp Arg His Phe Gln Glu Glu Ile Lys Thr Ala Leu Asp Tyr Ile
                    450                 455                 460
Tyr Lys Phe Trp Asn His Asp Ser Ile Phe Gly Asp Leu Asn Met Val
465                 470                 475                 480
Ala Leu Gly Phe Arg Ile Leu Arg Leu Asn Arg Tyr Val Ala Ser Ser
                    485                 490                 495
Asp Val Phe Lys Lys Phe Lys Gly Glu Glu Gly Gln Phe Ser Gly Phe
                    500                 505                 510
Glu Ser Ser Asp Gln Asp Ala Lys Leu Glu Met Met Leu Asn Leu Tyr
                    515                 520                 525
Lys Ala Ser Glu Leu Asp Phe Pro Asp Glu Asp Ile Leu Lys Glu Ala
                    530                 535                 540
Arg Ala Phe Ala Ser Met Tyr Leu Lys His Val Ile Lys Glu Tyr Gly
545                 550                 555                 560
Asp Ile Gln Glu Ser Lys Asn Pro Leu Leu Met Glu Ile Glu Tyr Thr
                    565                 570                 575
Phe Lys Tyr Pro Trp Arg Cys Arg Leu Pro Arg Leu Glu Ala Trp Asn
                    580                 585                 590
Phe Ile His Ile Met Arg Gln Gln Asp Cys Asn Ile Ser Leu Ala Asn
                    595                 600                 605
Asn Leu Tyr Lys Ile Pro Lys Ile Tyr Met Lys Lys Ile Leu Glu Leu
                    610                 615                 620
Ala Ile Leu Asp Phe Asn Ile Leu Gln Ser Gln His Gln His Glu Met
625                 630                 635                 640
Lys Leu Ile Ser Thr Trp Trp Lys Asn Ser Ser Ala Ile Gln Leu Asp
                    645                 650                 655
Phe Phe Arg His Arg His Ile Glu Ser Tyr Phe Trp Trp Ala Ser Pro
                    660                 665                 670
Leu Phe Glu Pro Glu Phe Ser Thr Cys Arg Ile Asn Cys Thr Lys Leu
                    675                 680                 685
Ser Thr Lys Met Phe Leu Leu Asp Asp Ile Tyr Asp Thr Tyr Gly Thr
                    690                 695                 700
Val Glu Glu Leu Lys Pro Phe Thr Thr Thr Leu Thr Arg Trp Asp Val
705                 710                 715                 720
Ser Thr Val Asp Asn His Pro Asp Tyr Met Lys Ile Ala Phe Asn Phe
                    725                 730                 735
```

```
Ser Tyr Glu Ile Tyr Lys Glu Ile Ala Ser Glu Ala Glu Arg Lys His
            740                 745                 750

Gly Pro Phe Val Tyr Lys Tyr Leu Gln Ser Cys Trp Lys Ser Tyr Ile
            755                 760                 765

Glu Ala Tyr Met Gln Glu Ala Glu Trp Ile Ala Ser Asn His Ile Pro
            770                 775                 780

Gly Phe Asp Glu Tyr Leu Met Asn Gly Val Lys Ser Ser Gly Met Arg
785                 790                 795                 800

Ile Leu Met Ile His Ala Leu Ile Leu Met Asp Thr Pro Leu Ser Asp
            805                 810                 815

Glu Ile Leu Glu Gln Leu Asp Ile Pro Ser Ser Lys Ser Gln Ala Leu
            820                 825                 830

Leu Ser Leu Ile Thr Arg Leu Val Asp Asp Val Lys Asp Phe Glu Asp
            835                 840                 845

Glu Gln Ala His Gly Glu Met Ala Ser Ser Ile Glu Cys Tyr Met Lys
            850                 855                 860

Asp Asn His Gly Ser Thr Arg Glu Asp Ala Leu Asn Tyr Leu Lys Ile
865                 870                 875                 880

Arg Ile Glu Ser Cys Val Gln Glu Leu Asn Lys Glu Leu Leu Glu Pro
            885                 890                 895

Ser Asn Met His Gly Ser Phe Arg Asn Leu Tyr Leu Asn Val Gly Met
            900                 905                 910

Arg Val Ile Phe Phe Met Leu Asn Asp Gly Asp Leu Phe Thr His Ser
            915                 920                 925

Asn Arg Lys Glu Ile Gln Asp Ala Ile Thr Lys Phe Phe Val Glu Pro
            930                 935                 940

Ile Ile Pro
945

<210> SEQ ID NO 24
<211> LENGTH: 1800
<212> TYPE: DNA
<213> ORGANISM: Artificial
<220> FEATURE:
<223> OTHER INFORMATION: synthetic gene set-ValFpoR
<220> FEATURE:
<221> NAME/KEY: CDS
<222> LOCATION: (1)..(1800)

<400> SEQUENCE: 24 atg gaa gag gcc tcg gtc acc tcg acc gaa gag acg ctg acg ccc gcg      48
Met Glu Glu Ala Ser Val Thr Ser Thr Glu Glu Thr Leu Thr Pro Ala
1               5                   10                  15 cag gaa gcc gcg cgc acc cgc gcg gcc aac aag gcg cgc aag gaa gcc      96
Gln Glu Ala Ala Arg Thr Arg Ala Ala Asn Lys Ala Arg Lys Glu Ala
                20                  25                  30 gag ctc gcc gcg gcc acc gcc gag cag ggt gat gac gac gac aag att     144
Glu Leu Ala Ala Ala Thr Ala Glu Gln Gly Asp Asp Asp Asp Lys Ile
            35                  40                  45 aat agc tcg ggc gag acc ttc cgc ccg acc gcc gat ttc cat ccc tcg     192
Asn Ser Ser Gly Glu Thr Phe Arg Pro Thr Ala Asp Phe His Pro Ser
    50                  55                  60 ctc tgg cgc aac cat ttc ctg aag ggc gcc tcc gac ttc aag acc gtc     240
Leu Trp Arg Asn His Phe Leu Lys Gly Ala Ser Asp Phe Lys Thr Val
65                  70                  75                  80 gat cac acg gcc acc cag gag cgc cac gag gcg ctg aag gaa gag gtg     288
Asp His Thr Ala Thr Gln Glu Arg His Glu Ala Leu Lys Glu Glu Val
                85                  90                  95
```

```
cgc cgg atg atc acc gac gcc gag gac aag ccg gtg cag aag ctg cgg         336
Arg Arg Met Ile Thr Asp Ala Glu Asp Lys Pro Val Gln Lys Leu Arg
            100                 105                 110 ctg atc gac gag gtg cag cgt ctc ggc gtg gcc tat cac ttc gag aag         384
Leu Ile Asp Glu Val Gln Arg Leu Gly Val Ala Tyr His Phe Glu Lys
        115                 120                 125 gag atc gag gat gcg atc cag aag ctc tgc ccg atc tac atc gac agc         432
Glu Ile Glu Asp Ala Ile Gln Lys Leu Cys Pro Ile Tyr Ile Asp Ser
130                 135                 140 aac cgc gcc gat ctg cac acg gtc tcg ctg cat ttc cgg ctg ctg cgc         480
Asn Arg Ala Asp Leu His Thr Val Ser Leu His Phe Arg Leu Leu Arg
145                 150                 155                 160 cag cag ggc atc aag atc tcc tgc gac gtc ttc gag aag ttc aag gac         528
Gln Gln Gly Ile Lys Ile Ser Cys Asp Val Phe Glu Lys Phe Lys Asp
                165                 170                 175 gac gag ggc cgc ttc aag tcc tcg ctg atc aac gac gtg cag ggg atg         576
Asp Glu Gly Arg Phe Lys Ser Ser Leu Ile Asn Asp Val Gln Gly Met
            180                 185                 190 ctg tcg ctc tac gag gcg gcc tac atg gcg gtg cgc ggc gag cat atc         624
Leu Ser Leu Tyr Glu Ala Ala Tyr Met Ala Val Arg Gly Glu His Ile
        195                 200                 205 ctc gac gag gcg atc gcc ttc acc acc acc cat ctg aaa tcg ctc gtg         672
Leu Asp Glu Ala Ile Ala Phe Thr Thr Thr His Leu Lys Ser Leu Val
210                 215                 220 gcg cag gac cat gtc acg ccg aag ctc gcc gag cag atc aac cat gcg         720
Ala Gln Asp His Val Thr Pro Lys Leu Ala Glu Gln Ile Asn His Ala
225                 230                 235                 240 ctc tac cgc ccg ctg cgc aag acg ctg ccg cgg ctc gag gcg cgc tat         768
Leu Tyr Arg Pro Leu Arg Lys Thr Leu Pro Arg Leu Glu Ala Arg Tyr
                245                 250                 255 ttc atg tcg atg atc aac tcg acc tcg gac cat ctc tac aac aag acg         816
Phe Met Ser Met Ile Asn Ser Thr Ser Asp His Leu Tyr Asn Lys Thr
            260                 265                 270 ctg ctg aac ttc gcc aag ctc gac ttc aac atc ctg ctc gag ctg cac         864
Leu Leu Asn Phe Ala Lys Leu Asp Phe Asn Ile Leu Leu Glu Leu His
        275                 280                 285 aag gaa gag ctg aac gag ctg acg aaa tgg tgg aag gat ctc gac ttc         912
Lys Glu Glu Leu Asn Glu Leu Thr Lys Trp Trp Lys Asp Leu Asp Phe
290                 295                 300 acc acc aag ctg ccc tat gcg cgc gac cgg ctg gtc gag ctc tat ttc         960
Thr Thr Lys Leu Pro Tyr Ala Arg Asp Arg Leu Val Glu Leu Tyr Phe
305                 310                 315                 320 tgg gat ctc ggc acc tat ttc gag ccg cag tat gcc ttc ggc cgc aag        1008
Trp Asp Leu Gly Thr Tyr Phe Glu Pro Gln Tyr Ala Phe Gly Arg Lys
                325                 330                 335 atc atg acc cag ctg aac tac atc ctc tcg atc atc gac gac acc tac        1056
Ile Met Thr Gln Leu Asn Tyr Ile Leu Ser Ile Ile Asp Asp Thr Tyr
            340                 345                 350 gac gcc tac ggc acg ctg gaa gag ctg tcg ctc ttc acc gag gcg gtg        1104
Asp Ala Tyr Gly Thr Leu Glu Glu Leu Ser Leu Phe Thr Glu Ala Val
        355                 360                 365 cag cgc tgg aac atc gag gcg gtc gac atg ctg ccg gaa tac atg aag        1152
Gln Arg Trp Asn Ile Glu Ala Val Asp Met Leu Pro Glu Tyr Met Lys
370                 375                 380 ctg atc tac cgc acg ctg ctc gat gcc ttc aac gag atc gag gaa gac        1200
Leu Ile Tyr Arg Thr Leu Leu Asp Ala Phe Asn Glu Ile Glu Glu Asp
385                 390                 395                 400 atg gcg aaa caa ggg cgc agc cac tgc gtg cgc tat gcc aag gaa gag        1248
Met Ala Lys Gln Gly Arg Ser His Cys Val Arg Tyr Ala Lys Glu Glu
```

```
                       405                   410                   415
aac cag aag gtc atc ggc gcc tat tcg gtc cag gcg aaa tgg ttc tcg         1296
Asn Gln Lys Val Ile Gly Ala Tyr Ser Val Gln Ala Lys Trp Phe Ser
            420                   425                   430 gaa ggc tat gtc ccc acg atc gag gaa tac atg ccg atc gcg ctg acc         1344
Glu Gly Tyr Val Pro Thr Ile Glu Glu Tyr Met Pro Ile Ala Leu Thr
            435                   440                   445 tcc tgc gcc tat acc ttc gtc atc acc aac agc ttc ctc ggc atg ggc         1392
Ser Cys Ala Tyr Thr Phe Val Ile Thr Asn Ser Phe Leu Gly Met Gly
        450                   455                   460 gac ttc gcc acc aag gaa gtc ttc gaa tgg atc tcg aac aac ccg aag         1440
Asp Phe Ala Thr Lys Glu Val Phe Glu Trp Ile Ser Asn Asn Pro Lys
465                   470                   475                   480 gtc gtc aag gcg gcc tcg gtc atc tgc cgg ctg atg gac gac atg cag         1488
Val Val Lys Ala Ala Ser Val Ile Cys Arg Leu Met Asp Asp Met Gln
                485                   490                   495 ggc cac gag ttc gag cag aag cgc ggc cat gtc gcc tcg gcc atc gaa         1536
Gly His Glu Phe Glu Gln Lys Arg Gly His Val Ala Ser Ala Ile Glu
            500                   505                   510 tgc tac acc aag cag cac ggc gtc tcg aag gaa gag gcg atc aag atg         1584
Cys Tyr Thr Lys Gln His Gly Val Ser Lys Glu Glu Ala Ile Lys Met
            515                   520                   525 ttc gaa gag gaa gtg gcc aat gcc tgg aag gac atc aac gag gaa ctg         1632
Phe Glu Glu Glu Val Ala Asn Ala Trp Lys Asp Ile Asn Glu Glu Leu
        530                   535                   540 atg atg aag ccc acc gtc gtg gcc cgt ccg ctg ctc ggc acg atc ctg         1680
Met Met Lys Pro Thr Val Val Ala Arg Pro Leu Leu Gly Thr Ile Leu
545                   550                   555                   560 aac ctc gcc cgc gcc atc gac ttc atc tac aag gaa gac gac ggc tat         1728
Asn Leu Ala Arg Ala Ile Asp Phe Ile Tyr Lys Glu Asp Asp Gly Tyr
                565                   570                   575 acc cat tcc tat ctg atc aag gac cag atc gcc tcg gtc ctc ggc gac         1776
Thr His Ser Tyr Leu Ile Lys Asp Gln Ile Ala Ser Val Leu Gly Asp
            580                   585                   590 cat gtg cct ttc att aat tga taa                                         1800
His Val Pro Phe Ile Asn
            595

<210> SEQ ID NO 25
<211> LENGTH: 598
<212> TYPE: PRT
<213> ORGANISM: Artificial
<220> FEATURE:
<223> OTHER INFORMATION: Synthetic Construct

<400> SEQUENCE: 25

Met Glu Glu Ala Ser Val Thr Ser Thr Glu Glu Thr Leu Thr Pro Ala
1               5                   10                  15

Gln Glu Ala Ala Arg Thr Arg Ala Ala Asn Lys Ala Arg Lys Glu Ala
                20                  25                  30

Glu Leu Ala Ala Ala Thr Ala Glu Gln Gly Asp Asp Asp Lys Ile
            35                  40                  45

Asn Ser Ser Gly Glu Thr Phe Arg Pro Thr Ala Asp Phe His Pro Ser
        50                  55                  60

Leu Trp Arg Asn His Phe Leu Lys Gly Ala Ser Asp Phe Lys Thr Val
65                  70                  75                  80

Asp His Thr Ala Thr Gln Glu Arg His Glu Ala Leu Lys Glu Glu Val
                85                  90                  95

Arg Arg Met Ile Thr Asp Ala Glu Asp Lys Pro Val Gln Lys Leu Arg
```

```
                100             105             110
Leu Ile Asp Glu Val Gln Arg Leu Gly Val Ala Tyr His Phe Glu Lys
            115             120             125
Glu Ile Glu Asp Ala Ile Gln Lys Leu Cys Pro Ile Tyr Ile Asp Ser
            130             135             140
Asn Arg Ala Asp Leu His Thr Val Ser Leu His Phe Arg Leu Leu Arg
145             150             155             160
Gln Gln Gly Ile Lys Ile Ser Cys Asp Val Phe Glu Lys Phe Lys Asp
                165             170             175
Asp Glu Gly Arg Phe Lys Ser Ser Leu Ile Asn Asp Val Gln Gly Met
            180             185             190
Leu Ser Leu Tyr Glu Ala Ala Tyr Met Ala Val Arg Gly Glu His Ile
            195             200             205
Leu Asp Glu Ala Ile Ala Phe Thr Thr Thr His Leu Lys Ser Leu Val
            210             215             220
Ala Gln Asp His Val Thr Pro Lys Leu Ala Glu Gln Ile Asn His Ala
225             230             235             240
Leu Tyr Arg Pro Leu Arg Lys Thr Leu Pro Arg Leu Glu Ala Arg Tyr
                245             250             255
Phe Met Ser Met Ile Asn Ser Thr Ser Asp His Leu Tyr Asn Lys Thr
                260             265             270
Leu Leu Asn Phe Ala Lys Leu Asp Phe Asn Ile Leu Leu Glu Leu His
            275             280             285
Lys Glu Glu Leu Asn Glu Leu Thr Lys Trp Lys Asp Leu Asp Phe
            290             295             300
Thr Thr Lys Leu Pro Tyr Ala Arg Asp Arg Leu Val Glu Leu Tyr Phe
305             310             315             320
Trp Asp Leu Gly Thr Tyr Phe Glu Pro Gln Tyr Ala Phe Gly Arg Lys
                325             330             335
Ile Met Thr Gln Leu Asn Tyr Ile Leu Ser Ile Ile Asp Asp Thr Tyr
            340             345             350
Asp Ala Tyr Gly Thr Leu Glu Glu Leu Ser Leu Phe Thr Glu Ala Val
            355             360             365
Gln Arg Trp Asn Ile Glu Ala Val Asp Met Leu Pro Glu Tyr Met Lys
            370             375             380
Leu Ile Tyr Arg Thr Leu Leu Asp Ala Phe Asn Glu Ile Glu Glu Asp
385             390             395             400
Met Ala Lys Gln Gly Arg Ser His Cys Val Arg Tyr Ala Lys Glu Glu
                405             410             415
Asn Gln Lys Val Ile Gly Ala Tyr Ser Val Gln Ala Lys Trp Phe Ser
            420             425             430
Glu Gly Tyr Val Pro Thr Ile Glu Glu Tyr Met Pro Ile Ala Leu Thr
            435             440             445
Ser Cys Ala Tyr Thr Phe Val Ile Thr Asn Ser Phe Leu Gly Met Gly
            450             455             460
Asp Phe Ala Thr Lys Glu Val Phe Glu Trp Ile Ser Asn Asn Pro Lys
465             470             475             480
Val Val Lys Ala Ala Ser Val Ile Cys Arg Leu Met Asp Asp Met Gln
                485             490             495
Gly His Glu Phe Glu Gln Lys Arg Gly His Val Ala Ser Ala Ile Glu
            500             505             510
Cys Tyr Thr Lys Gln His Gly Val Ser Lys Glu Glu Ala Ile Lys Met
            515             520             525
```

```
Phe Glu Glu Val Ala Asn Ala Trp Lys Asp Ile Asn Glu Glu Leu
    530                 535                 540

Met Met Lys Pro Thr Val Ala Arg Pro Leu Leu Gly Thr Ile Leu
545                 550                 555                 560

Asn Leu Ala Arg Ala Ile Asp Phe Ile Tyr Lys Glu Asp Gly Tyr
                565                 570                 575

Thr His Ser Tyr Leu Ile Lys Asp Gln Ile Ala Ser Val Leu Gly Asp
                580                 585                 590

His Val Pro Phe Ile Asn
            595

<210> SEQ ID NO 26
<211> LENGTH: 1644
<212> TYPE: DNA
<213> ORGANISM: Artificial
<220> FEATURE:
<223> OTHER INFORMATION: synthetic gene aaaS
<220> FEATURE:
<221> NAME/KEY: CDS
<222> LOCATION: (1)..(1644)

<400> SEQUENCE: 26
```

| | | | | | | | | | | | | | | | |
|---|---|---|---|---|---|---|---|---|---|---|---|---|---|---|---|
| atg | gcc | ctg | acc | gag | gaa | aag | ccg | atc | cgc | ccc | atc | gcg | aac | ttc | ccg | 48 |
| Met | Ala | Leu | Thr | Glu | Glu | Lys | Pro | Ile | Arg | Pro | Ile | Ala | Asn | Phe | Pro |
| 1 | | | | 5 | | | | | 10 | | | | | 15 | |

```
ccc agc atc tgg ggc gat cag ttc ctg atc tac gag aag cag gtg gag    96
Pro Ser Ile Trp Gly Asp Gln Phe Leu Ile Tyr Glu Lys Gln Val Glu
             20                  25                  30 cag ggc gtc gag cag atc gtg aac gat ctc aag aag gag gtg cgg cag   144
Gln Gly Val Glu Gln Ile Val Asn Asp Leu Lys Lys Glu Val Arg Gln
         35                  40                  45 ctg ctg aag gag gcc ctc gat atc ccc atg aag cac gcc aac ctc ctg   192
Leu Leu Lys Glu Ala Leu Asp Ile Pro Met Lys His Ala Asn Leu Leu
     50                  55                  60 aag ctg atc gat gaa atc cag cgc ctc ggc atc ccg tat cac ttc gaa   240
Lys Leu Ile Asp Glu Ile Gln Arg Leu Gly Ile Pro Tyr His Phe Glu
 65                  70                  75                  80 cgc gag atc gac cac gcg ctc cag tgc atc tat gag acc tac ggc gac   288
Arg Glu Ile Asp His Ala Leu Gln Cys Ile Tyr Glu Thr Tyr Gly Asp
                 85                  90                  95 aac tgg aac ggc gac cgc tcg tcc ctc tgg ttc cgc ctg atg cgc aag   336
Asn Trp Asn Gly Asp Arg Ser Ser Leu Trp Phe Arg Leu Met Arg Lys
            100                 105                 110 cag ggc tat tac gtg acc tgc gat gtc ttc aac aac tat aag gac aag   384
Gln Gly Tyr Tyr Val Thr Cys Asp Val Phe Asn Asn Tyr Lys Asp Lys
        115                 120                 125 aac ggg gcg ttc aaa cag tcg ctc gcg aac gac gtg gag ggc ctg ctg   432
Asn Gly Ala Phe Lys Gln Ser Leu Ala Asn Asp Val Glu Gly Leu Leu
    130                 135                 140 gag ctg tat gag gcg acg agc atg cgc gtc ccc ggc gag atc atc ctg   480
Glu Leu Tyr Glu Ala Thr Ser Met Arg Val Pro Gly Glu Ile Ile Leu
145                 150                 155                 160 gag gac gcg ctc ggc ttc acg cgc tcg cgc ctc tcc atc atg acg aag   528
Glu Asp Ala Leu Gly Phe Thr Arg Ser Arg Leu Ser Ile Met Thr Lys
                165                 170                 175 gac gcc ttc tcg acg aac ccg gcg ctg ttc acc gag atc cag cgg gcg   576
Asp Ala Phe Ser Thr Asn Pro Ala Leu Phe Thr Glu Ile Gln Arg Ala
            180                 185                 190 ctc aag cag ccg ctg tgg aag cgc ctg ccc cgc atc gag gcg gcg cag   624
Leu Lys Gln Pro Leu Trp Lys Arg Leu Pro Arg Ile Glu Ala Ala Gln
```

```
            195                 200                 205
tac atc ccc ttc tat cag cag cag gat agc cat aac aag acg ctc ctc      672
Tyr Ile Pro Phe Tyr Gln Gln Gln Asp Ser His Asn Lys Thr Leu Leu
    210                 215                 220 aag ctc gcg aag ctc gag ttc aac ctg ctg cag tcg ctc cat aag gag      720
Lys Leu Ala Lys Leu Glu Phe Asn Leu Leu Gln Ser Leu His Lys Glu
225                 230                 235                 240 gag ctg tcg cat gtg tgc aag tgg tgg aag gcg ttc gat atc aaa aag      768
Glu Leu Ser His Val Cys Lys Trp Trp Lys Ala Phe Asp Ile Lys Lys
                245                 250                 255 aac gcc ccc tgc ctc cgg gac cgc atc gtc gag tgc tat ttc tgg ggc      816
Asn Ala Pro Cys Leu Arg Asp Arg Ile Val Glu Cys Tyr Phe Trp Gly
            260                 265                 270 ctg ggc tcg ggc tat gag ccg cag tac tcc cgc gcc cgg gtc ttc ttc      864
Leu Gly Ser Gly Tyr Glu Pro Gln Tyr Ser Arg Ala Arg Val Phe Phe
        275                 280                 285 acc aag gcg gtg gcg gtg atc acg ctc atc gac gat acg tac gac gcc      912
Thr Lys Ala Val Ala Val Ile Thr Leu Ile Asp Asp Thr Tyr Asp Ala
    290                 295                 300 tac ggc acg tac gag gaa ctg aaa atc ttc acc gag gcc gtg gaa cgc      960
Tyr Gly Thr Tyr Glu Glu Leu Lys Ile Phe Thr Glu Ala Val Glu Arg
305                 310                 315                 320 tgg tcg atc acc tgc ctc gat acg ctc ccg gag tat atg aag ccc atc     1008
Trp Ser Ile Thr Cys Leu Asp Thr Leu Pro Glu Tyr Met Lys Pro Ile
                325                 330                 335 tat aag ctc ttc atg gat acc tat acc gag atg gag gag ttc ctc gcg     1056
Tyr Lys Leu Phe Met Asp Thr Tyr Thr Glu Met Glu Glu Phe Leu Ala
            340                 345                 350 aag gag ggg cgc acg gac ctg ttc aac tgc ggc aag gag ttc gtc aag     1104
Lys Glu Gly Arg Thr Asp Leu Phe Asn Cys Gly Lys Glu Phe Val Lys
        355                 360                 365 gag ttc gtg cgc aac ctg atg gtg gag gcg aag tgg gcc aac gag ggg     1152
Glu Phe Val Arg Asn Leu Met Val Glu Ala Lys Trp Ala Asn Glu Gly
    370                 375                 380 cat atc ccc acg acg gag gag cat gac ccc gtg gtg atc atc acc ggc     1200
His Ile Pro Thr Thr Glu Glu His Asp Pro Val Val Ile Ile Thr Gly
385                 390                 395                 400 ggc gcc aac ctg ctc acc acc acc tgc tac ctg ggc atg tcc gac atc     1248
Gly Ala Asn Leu Leu Thr Thr Thr Cys Tyr Leu Gly Met Ser Asp Ile
                405                 410                 415 ttc acg aag gag agc gtg gag tgg gcg gtg tcc gcc ccc ccg ctc ttc     1296
Phe Thr Lys Glu Ser Val Glu Trp Ala Val Ser Ala Pro Pro Leu Phe
            420                 425                 430 cgc tat tcg ggc atc ctg ggc cgg cgg ctc aac gac ctc atg acc cac     1344
Arg Tyr Ser Gly Ile Leu Gly Arg Arg Leu Asn Asp Leu Met Thr His
        435                 440                 445 aaa gcg gag cag gag cgg aag cac tcc tcg agc agc ctg gaa agc tat     1392
Lys Ala Glu Gln Glu Arg Lys His Ser Ser Ser Ser Leu Glu Ser Tyr
    450                 455                 460 atg aag gaa tat aac gtg aac gag gag tac gcc cag acg ctg atc tac     1440
Met Lys Glu Tyr Asn Val Asn Glu Glu Tyr Ala Gln Thr Leu Ile Tyr
465                 470                 475                 480 aag gag gtc gag gat gtg tgg aag gac atc aac cgg gag tat ctc acg     1488
Lys Glu Val Glu Asp Val Trp Lys Asp Ile Asn Arg Glu Tyr Leu Thr
                485                 490                 495 acg aag aac atc ccc cgc ccg ctc ctc atg gcg gtc atc tac ctc tgc     1536
Thr Lys Asn Ile Pro Arg Pro Leu Leu Met Ala Val Ile Tyr Leu Cys
            500                 505                 510 cag ttc ctg gag gtc cag tat gcg ggc aag gat aat ttc acg cgc atg     1584
```

```
Gln Phe Leu Glu Val Gln Tyr Ala Gly Lys Asp Asn Phe Thr Arg Met
            515                 520                 525 ggc gat gag tat aag cac ctg atc aag tcg ctg ctc gtg tac ccc atg      1632
Gly Asp Glu Tyr Lys His Leu Ile Lys Ser Leu Leu Val Tyr Pro Met
        530                 535                 540 tcg atc tga taa                                                       1644
Ser Ile
545

<210> SEQ ID NO 27
<211> LENGTH: 546
<212> TYPE: PRT
<213> ORGANISM: Artificial
<220> FEATURE:
<223> OTHER INFORMATION: Synthetic Construct

<400> SEQUENCE: 27

Met Ala Leu Thr Glu Glu Lys Pro Ile Arg Pro Ile Ala Asn Phe Pro
1               5                   10                  15

Pro Ser Ile Trp Gly Asp Gln Phe Leu Ile Tyr Glu Lys Gln Val Glu
            20                  25                  30

Gln Gly Val Glu Gln Ile Val Asn Asp Leu Lys Lys Glu Val Arg Gln
        35                  40                  45

Leu Leu Lys Glu Ala Leu Asp Ile Pro Met Lys His Ala Asn Leu Leu
50                  55                  60

Lys Leu Ile Asp Glu Ile Gln Arg Leu Gly Ile Pro Tyr His Phe Glu
65                  70                  75                  80

Arg Glu Ile Asp His Ala Leu Gln Cys Ile Tyr Glu Thr Tyr Gly Asp
                85                  90                  95

Asn Trp Asn Gly Asp Arg Ser Ser Leu Trp Phe Arg Leu Met Arg Lys
            100                 105                 110

Gln Gly Tyr Tyr Val Thr Cys Asp Val Phe Asn Asn Tyr Lys Asp Lys
        115                 120                 125

Asn Gly Ala Phe Lys Gln Ser Leu Ala Asn Asp Val Glu Gly Leu Leu
130                 135                 140

Glu Leu Tyr Glu Ala Thr Ser Met Arg Val Pro Gly Glu Ile Ile Leu
145                 150                 155                 160

Glu Asp Ala Leu Gly Phe Thr Arg Ser Arg Leu Ser Ile Met Thr Lys
                165                 170                 175

Asp Ala Phe Ser Thr Asn Pro Ala Leu Phe Thr Glu Ile Gln Arg Ala
            180                 185                 190

Leu Lys Gln Pro Leu Trp Lys Arg Leu Pro Arg Ile Glu Ala Ala Gln
        195                 200                 205

Tyr Ile Pro Phe Tyr Gln Gln Asp Ser His Asn Lys Thr Leu Leu
210                 215                 220

Lys Leu Ala Lys Leu Glu Phe Asn Leu Leu Gln Ser Leu His Lys Glu
225                 230                 235                 240

Glu Leu Ser His Val Cys Lys Trp Trp Lys Ala Phe Asp Ile Lys Lys
                245                 250                 255

Asn Ala Pro Cys Leu Arg Asp Arg Ile Val Glu Cys Tyr Phe Trp Gly
            260                 265                 270

Leu Gly Ser Gly Tyr Glu Pro Gln Tyr Ser Arg Ala Arg Val Phe Phe
        275                 280                 285

Thr Lys Ala Val Ala Val Ile Thr Leu Ile Asp Asp Thr Tyr Asp Ala
290                 295                 300

Tyr Gly Thr Tyr Glu Glu Leu Lys Ile Phe Thr Glu Ala Val Glu Arg
```

-continued

```
                305                 310                 315                 320
        Trp Ser Ile Thr Cys Leu Asp Thr Leu Pro Glu Tyr Met Lys Pro Ile
                        325                 330                 335

Tyr Lys Leu Phe Met Asp Thr Tyr Thr Glu Met Glu Glu Phe Leu Ala
                        340                 345                 350

Lys Glu Gly Arg Thr Asp Leu Phe Asn Cys Gly Lys Glu Phe Val Lys
                        355                 360                 365

Glu Phe Val Arg Asn Leu Met Val Glu Ala Lys Trp Ala Asn Glu Gly
                370                 375                 380

His Ile Pro Thr Thr Glu Glu His Asp Pro Val Val Ile Ile Thr Gly
        385                 390                 395                 400

Gly Ala Asn Leu Leu Thr Thr Thr Cys Tyr Leu Gly Met Ser Asp Ile
                        405                 410                 415

Phe Thr Lys Glu Ser Val Glu Trp Ala Val Ser Ala Pro Pro Leu Phe
                        420                 425                 430

Arg Tyr Ser Gly Ile Leu Gly Arg Arg Leu Asn Asp Leu Met Thr His
                        435                 440                 445

Lys Ala Glu Gln Glu Arg Lys His Ser Ser Ser Leu Glu Ser Tyr
                450                 455                 460

Met Lys Glu Tyr Asn Val Asn Glu Glu Tyr Ala Gln Thr Leu Ile Tyr
        465                 470                 475                 480

Lys Glu Val Glu Asp Val Trp Lys Asp Ile Asn Arg Glu Tyr Leu Thr
                        485                 490                 495

Thr Lys Asn Ile Pro Arg Pro Leu Leu Met Ala Val Ile Tyr Leu Cys
                        500                 505                 510

Gln Phe Leu Glu Val Gln Tyr Ala Gly Lys Asp Asn Phe Thr Arg Met
                        515                 520                 525

Gly Asp Glu Tyr Lys His Leu Ile Lys Ser Leu Leu Val Tyr Pro Met
                530                 535                 540

Ser Ile
        545

<210> SEQ ID NO 28
<211> LENGTH: 2766
<212> TYPE: DNA
<213> ORGANISM: Artificial
<220> FEATURE:
<223> OTHER INFORMATION: synthetic gene mbp-aaaS
<220> FEATURE:
<221> NAME/KEY: CDS
<222> LOCATION: (1)..(2766)

<400> SEQUENCE: 28 atg aag atc gag gaa ggc aag ctc gtc atc tgg atc aac ggc gac aag      48
Met Lys Ile Glu Glu Gly Lys Leu Val Ile Trp Ile Asn Gly Asp Lys
1               5                   10                  15 ggc tac aac ggc ctc gcc gag gtg ggc aag aag ttc gag aag gac acg      96
Gly Tyr Asn Gly Leu Ala Glu Val Gly Lys Lys Phe Glu Lys Asp Thr
            20                  25                  30 ggc atc aag gtc acc gtc gag cat ccc gac aag ctc gag gag aag ttc     144
Gly Ile Lys Val Thr Val Glu His Pro Asp Lys Leu Glu Glu Lys Phe
        35                  40                  45 ccg cag gtc gcc gcc acc ggc gac ggc ccc gac atc atc ttc tgg gcc     192
Pro Gln Val Ala Ala Thr Gly Asp Gly Pro Asp Ile Ile Phe Trp Ala
    50                  55                  60 cac gac cgc ttc ggc ggc tat gcg cag tcg ggc ctg ctc gcc gag atc     240
His Asp Arg Phe Gly Gly Tyr Ala Gln Ser Gly Leu Leu Ala Glu Ile
65                  70                  75                  80
```

| | | |
|---|---|---|
| acg ccc gac aag gcc ttc cag gac aag ctc tat ccc ttc acc tgg gat<br>Thr Pro Asp Lys Ala Phe Gln Asp Lys Leu Tyr Pro Phe Thr Trp Asp<br>                85                    90                  95 | 288 |
| gcg gtg cgc tac aac ggc aag ctg atc gcc tat ccg atc gcc gtc gag<br>Ala Val Arg Tyr Asn Gly Lys Leu Ile Ala Tyr Pro Ile Ala Val Glu<br>              100                 105               110 | 336 |
| gcg ctg tcg ctg atc tac aac aag gat ctg ctg ccg aac ccg ccg aag<br>Ala Leu Ser Leu Ile Tyr Asn Lys Asp Leu Leu Pro Asn Pro Pro Lys<br>           115                 120               125 | 384 |
| acc tgg gaa gag atc ccg gcg ctc gac aag gaa ctg aag gcc aag ggc<br>Thr Trp Glu Glu Ile Pro Ala Leu Asp Lys Glu Leu Lys Ala Lys Gly<br>130                 135               140 | 432 |
| aag tcc gcg ctg atg ttc aac ctg cag gag ccc tat ttc acc tgg ccg<br>Lys Ser Ala Leu Met Phe Asn Leu Gln Glu Pro Tyr Phe Thr Trp Pro<br>145                 150               155               160 | 480 |
| ctg atc gcc gcc gac ggc ggc tat gcc ttc aaa tac gag aac ggc aaa<br>Leu Ile Ala Ala Asp Gly Gly Tyr Ala Phe Lys Tyr Glu Asn Gly Lys<br>              165               170               175 | 528 |
| tac gac atc aag gac gtg ggc gtc gac aat gcg ggc gcc aag gcc ggg<br>Tyr Asp Ile Lys Asp Val Gly Val Asp Asn Ala Gly Ala Lys Ala Gly<br>           180                 185               190 | 576 |
| ctg acc ttc ctc gtc gat ctg atc aag aac aag cac atg aat gcc gac<br>Leu Thr Phe Leu Val Asp Leu Ile Lys Asn Lys His Met Asn Ala Asp<br>              195               200               205 | 624 |
| acc gac tat tcc atc gcc gag gcg gcc ttc aac aag ggc gag acc gcc<br>Thr Asp Tyr Ser Ile Ala Glu Ala Ala Phe Asn Lys Gly Glu Thr Ala<br>210                 215               220 | 672 |
| atg acg atc aac ggg ccg tgg gcc tgg tcg aac atc gac acc tcg aag<br>Met Thr Ile Asn Gly Pro Trp Ala Trp Ser Asn Ile Asp Thr Ser Lys<br>225                 230               235               240 | 720 |
| gtc aat tac ggc gtc acg gtg ctg ccg acc ttc aag ggc cag ccc tcg<br>Val Asn Tyr Gly Val Thr Val Leu Pro Thr Phe Lys Gly Gln Pro Ser<br>              245               250               255 | 768 |
| aaa ccc ttc gtc ggc gtg ctg tcg gcg ggc atc aac gcg gcc tcg ccg<br>Lys Pro Phe Val Gly Val Leu Ser Ala Gly Ile Asn Ala Ala Ser Pro<br>           260                 265               270 | 816 |
| aac aag gaa ctc gcc aag gag ttc ctc gag aac tac ctg ctg acc gac<br>Asn Lys Glu Leu Ala Lys Glu Phe Leu Glu Asn Tyr Leu Leu Thr Asp<br>275                 280               285 | 864 |
| gag ggg ctc gag gcg gtg aac aag gac aag ccg ctc ggc gcg gtg gcg<br>Glu Gly Leu Glu Ala Val Asn Lys Asp Lys Pro Leu Gly Ala Val Ala<br>           290                 295               300 | 912 |
| ctg aaa tcc tac gag gaa gag ctc gtc aag gac ccg cgg atc gcc gcc<br>Leu Lys Ser Tyr Glu Glu Glu Leu Val Lys Asp Pro Arg Ile Ala Ala<br>305                 310               315               320 | 960 |
| acg atg gag aat gcg cag aag ggc gag atc atg ccg aac atc ccg cag<br>Thr Met Glu Asn Ala Gln Lys Gly Glu Ile Met Pro Asn Ile Pro Gln<br>              325               330               335 | 1008 |
| atg tcg gcc ttc tgg tat gcc gtc cgc acc gcg gtg atc aac gcg gcc<br>Met Ser Ala Phe Trp Tyr Ala Val Arg Thr Ala Val Ile Asn Ala Ala<br>           340                 345               350 | 1056 |
| tcg ggc cgt cag acc gtc gac gag gcg ctg aag gat gcg cag act ggt<br>Ser Gly Arg Gln Thr Val Asp Glu Ala Leu Lys Asp Ala Gln Thr Gly<br>              355               360               365 | 1104 |
| gat gac gac gac aag att atg gcc ctg acc gag gaa aag ccg atc cgc<br>Asp Asp Asp Asp Lys Ile Met Ala Leu Thr Glu Glu Lys Pro Ile Arg<br>           370                 375               380 | 1152 |
| ccc atc gcg aac ttc ccg ccc agc atc tgg ggc gat cag ttc ctg atc<br>Pro Ile Ala Asn Phe Pro Pro Ser Ile Trp Gly Asp Gln Phe Leu Ile | 1200 |

```
           385                 390                 395                 400
tac gag aag cag gtg gag cag ggc gtc gag cag atc gtg aac gat ctc    1248
Tyr Glu Lys Gln Val Glu Gln Gly Val Glu Gln Ile Val Asn Asp Leu
                    405                 410                 415 aag aag gag gtg cgg cag ctg ctg aag gag gcc ctc gat atc ccc atg    1296
Lys Lys Glu Val Arg Gln Leu Leu Lys Glu Ala Leu Asp Ile Pro Met
                    420                 425                 430 aag cac gcc aac ctc ctg aag ctg atc gat gaa atc cag cgc ctc ggc    1344
Lys His Ala Asn Leu Leu Lys Leu Ile Asp Glu Ile Gln Arg Leu Gly
                    435                 440                 445 atc ccg tat cac ttc gaa cgc gag atc gac cac gcg ctc cag tgc atc    1392
Ile Pro Tyr His Phe Glu Arg Glu Ile Asp His Ala Leu Gln Cys Ile
                    450                 455                 460 tat gag acc tac ggc gac aac tgg aac ggc gac cgc tcg tcc ctc tgg    1440
Tyr Glu Thr Tyr Gly Asp Asn Trp Asn Gly Asp Arg Ser Ser Leu Trp
465                 470                 475                 480 ttc cgc ctg atg cgc aag cag ggc tat tac gtg acc tgc gat gtc ttc    1488
Phe Arg Leu Met Arg Lys Gln Gly Tyr Tyr Val Thr Cys Asp Val Phe
                    485                 490                 495 aac aac tat aag gac aag aac ggg gcg ttc aaa cag tcg ctc gcg aac    1536
Asn Asn Tyr Lys Asp Lys Asn Gly Ala Phe Lys Gln Ser Leu Ala Asn
                    500                 505                 510 gac gtg gag ggc ctg ctg gag ctg tat gag gcg acg agc atg cgc gtc    1584
Asp Val Glu Gly Leu Leu Glu Leu Tyr Glu Ala Thr Ser Met Arg Val
                    515                 520                 525 ccc ggc gag atc atc ctg gag gac gcg ctc ggc ttc acg cgc tcg cgc    1632
Pro Gly Glu Ile Ile Leu Glu Asp Ala Leu Gly Phe Thr Arg Ser Arg
                    530                 535                 540 ctc tcc atc atg acg aag gac gcc ttc tcg acg aac ccg gcg ctg ttc    1680
Leu Ser Ile Met Thr Lys Asp Ala Phe Ser Thr Asn Pro Ala Leu Phe
545                 550                 555                 560 acc gag atc cag cgg gcg ctc aag cag ccg ctg tgg aag cgc ctg ccc    1728
Thr Glu Ile Gln Arg Ala Leu Lys Gln Pro Leu Trp Lys Arg Leu Pro
                    565                 570                 575 cgc atc gag gcg gcg cag tac atc ccc ttc tat cag cag cag gat agc    1776
Arg Ile Glu Ala Ala Gln Tyr Ile Pro Phe Tyr Gln Gln Gln Asp Ser
                    580                 585                 590 cat aac aag acg ctc ctc aag ctc gcg aag ctc gag ttc aac ctg ctg    1824
His Asn Lys Thr Leu Leu Lys Leu Ala Lys Leu Glu Phe Asn Leu Leu
                    595                 600                 605 cag tcg ctc cat aag gag gag ctg tcg cat gtg tgc aag tgg tgg aag    1872
Gln Ser Leu His Lys Glu Glu Leu Ser His Val Cys Lys Trp Trp Lys
                    610                 615                 620 gcg ttc gat atc aaa aag aac gcc ccc tgc ctc cgg gac cgc atc gtc    1920
Ala Phe Asp Ile Lys Lys Asn Ala Pro Cys Leu Arg Asp Arg Ile Val
625                 630                 635                 640 gag tgc tat ttc tgg ggc ctg ggc tcg ggc tat gag ccg cag tac tcc    1968
Glu Cys Tyr Phe Trp Gly Leu Gly Ser Gly Tyr Glu Pro Gln Tyr Ser
                    645                 650                 655 cgc gcc cgg gtc ttc ttc acc aag gcg gtg gcg gtg atc acg ctc atc    2016
Arg Ala Arg Val Phe Phe Thr Lys Ala Val Ala Val Ile Thr Leu Ile
                    660                 665                 670 gac gat acg tac gac gcc tac ggc acg tac gag gaa ctg aaa atc ttc    2064
Asp Asp Thr Tyr Asp Ala Tyr Gly Thr Tyr Glu Glu Leu Lys Ile Phe
                    675                 680                 685 acc gag gcc gtg gaa cgc tgg tcg atc acc tgc ctc gat acg ctc ccg    2112
Thr Glu Ala Val Glu Arg Trp Ser Ile Thr Cys Leu Asp Thr Leu Pro
                    690                 695                 700 gag tat atg aag ccc atc tat aag ctc ttc atg gat acc tat acc gag    2160
```

```
Glu Tyr Met Lys Pro Ile Tyr Lys Leu Phe Met Asp Thr Tyr Thr Glu
705                 710                 715                 720 atg gag gag ttc ctc gcg aag gag ggg cgc acg gac ctg ttc aac tgc    2208
Met Glu Glu Phe Leu Ala Lys Glu Gly Arg Thr Asp Leu Phe Asn Cys
            725                 730                 735 ggc aag gag ttc gtc aag gag ttc gtg cgc aac ctg atg gtg gag gcg    2256
Gly Lys Glu Phe Val Lys Glu Phe Val Arg Asn Leu Met Val Glu Ala
        740                 745                 750 aag tgg gcc aac gag ggg cat atc ccc acg acg gag gag cat gac ccc    2304
Lys Trp Ala Asn Glu Gly His Ile Pro Thr Thr Glu Glu His Asp Pro
    755                 760                 765 gtg gtg atc atc acc ggc ggc gcc aac ctg ctc acc acc acc tgc tac    2352
Val Val Ile Ile Thr Gly Gly Ala Asn Leu Leu Thr Thr Thr Cys Tyr
770                 775                 780 ctg ggc atg tcc gac atc ttc acg aag gag agc gtg gag tgg gcg gtg    2400
Leu Gly Met Ser Asp Ile Phe Thr Lys Glu Ser Val Glu Trp Ala Val
785                 790                 795                 800 tcc gcc ccc ccg ctc ttc cgc tat tcg ggc atc ctg ggc cgg cgg ctc    2448
Ser Ala Pro Pro Leu Phe Arg Tyr Ser Gly Ile Leu Gly Arg Arg Leu
                805                 810                 815 aac gac ctc atg acc cac aaa gcg gag cag gag cgg aag cac tcc tcg    2496
Asn Asp Leu Met Thr His Lys Ala Glu Gln Glu Arg Lys His Ser Ser
            820                 825                 830 agc agc ctg gaa agc tat atg aag gaa tat aac gtg aac gag gag tac    2544
Ser Ser Leu Glu Ser Tyr Met Lys Glu Tyr Asn Val Asn Glu Glu Tyr
        835                 840                 845 gcc cag acg ctg atc tac aag gag gtc gag gat gtg tgg aag gac atc    2592
Ala Gln Thr Leu Ile Tyr Lys Glu Val Glu Asp Val Trp Lys Asp Ile
    850                 855                 860 aac cgg gag tat ctc acg acg aag aac atc ccc cgc ccg ctc ctc atg    2640
Asn Arg Glu Tyr Leu Thr Thr Lys Asn Ile Pro Arg Pro Leu Leu Met
865                 870                 875                 880 gcg gtc atc tac ctc tgc cag ttc ctg gag gtc cag tat gcg ggc aag    2688
Ala Val Ile Tyr Leu Cys Gln Phe Leu Glu Val Gln Tyr Ala Gly Lys
                885                 890                 895 gat aat ttc acg cgc atg ggc gat gag tat aag cac ctg atc aag tcg    2736
Asp Asn Phe Thr Arg Met Gly Asp Glu Tyr Lys His Leu Ile Lys Ser
            900                 905                 910 ctg ctc gtg tac ccc atg tcg atc tga taa                            2766
Leu Leu Val Tyr Pro Met Ser Ile
        915                 920

<210> SEQ ID NO 29
<211> LENGTH: 920
<212> TYPE: PRT
<213> ORGANISM: Artificial
<220> FEATURE:
<223> OTHER INFORMATION: Synthetic Construct

<400> SEQUENCE: 29

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80
```

-continued

```
Thr Pro Asp Lys Ala Phe Gln Asp Lys Leu Tyr Pro Phe Thr Trp Asp
                85                  90                  95
Ala Val Arg Tyr Asn Gly Lys Leu Ile Ala Tyr Pro Ile Ala Val Glu
            100                 105                 110
Ala Leu Ser Leu Ile Tyr Asn Lys Asp Leu Leu Pro Asn Pro Pro Lys
        115                 120                 125
Thr Trp Glu Glu Ile Pro Ala Leu Asp Lys Glu Leu Lys Ala Lys Gly
    130                 135                 140
Lys Ser Ala Leu Met Phe Asn Leu Gln Glu Pro Tyr Phe Thr Trp Pro
145                 150                 155                 160
Leu Ile Ala Ala Asp Gly Gly Tyr Ala Phe Lys Tyr Glu Asn Gly Lys
                165                 170                 175
Tyr Asp Ile Lys Asp Val Gly Val Asp Asn Ala Gly Ala Lys Ala Gly
            180                 185                 190
Leu Thr Phe Leu Val Asp Leu Ile Lys Asn Lys His Met Asn Ala Asp
        195                 200                 205
Thr Asp Tyr Ser Ile Ala Glu Ala Ala Phe Asn Lys Gly Glu Thr Ala
    210                 215                 220
Met Thr Ile Asn Gly Pro Trp Ala Trp Ser Asn Ile Asp Thr Ser Lys
225                 230                 235                 240
Val Asn Tyr Gly Val Thr Val Leu Pro Thr Phe Lys Gly Gln Pro Ser
                245                 250                 255
Lys Pro Phe Val Gly Val Leu Ser Ala Gly Ile Asn Ala Ala Ser Pro
            260                 265                 270
Asn Lys Glu Leu Ala Lys Glu Phe Leu Glu Asn Tyr Leu Leu Thr Asp
        275                 280                 285
Glu Gly Leu Glu Ala Val Asn Lys Asp Lys Pro Leu Gly Ala Val Ala
    290                 295                 300
Leu Lys Ser Tyr Glu Glu Glu Leu Val Lys Asp Pro Arg Ile Ala Ala
305                 310                 315                 320
Thr Met Glu Asn Ala Gln Lys Gly Glu Ile Met Pro Asn Ile Pro Gln
                325                 330                 335
Met Ser Ala Phe Trp Tyr Ala Val Arg Thr Ala Val Ile Asn Ala Ala
            340                 345                 350
Ser Gly Arg Gln Thr Val Asp Glu Ala Leu Lys Asp Ala Gln Thr Gly
        355                 360                 365
Asp Asp Asp Asp Lys Ile Met Ala Leu Thr Glu Glu Lys Pro Ile Arg
    370                 375                 380
Pro Ile Ala Asn Phe Pro Pro Ser Ile Trp Gly Asp Gln Phe Leu Ile
385                 390                 395                 400
Tyr Glu Lys Gln Val Glu Gln Gly Val Glu Gln Ile Val Asn Asp Leu
                405                 410                 415
Lys Lys Glu Val Arg Gln Leu Leu Lys Glu Ala Leu Asp Ile Pro Met
            420                 425                 430
Lys His Ala Asn Leu Leu Lys Leu Ile Asp Glu Ile Gln Arg Leu Gly
        435                 440                 445
Ile Pro Tyr His Phe Glu Arg Glu Ile Asp His Ala Leu Gln Cys Ile
    450                 455                 460
Tyr Glu Thr Tyr Gly Asp Asn Trp Asn Gly Asp Arg Ser Ser Leu Trp
465                 470                 475                 480
Phe Arg Leu Met Arg Lys Gln Gly Tyr Tyr Val Thr Cys Asp Val Phe
                485                 490                 495
```

```
Asn Asn Tyr Lys Asp Lys Asn Gly Ala Phe Lys Gln Ser Leu Ala Asn
            500                 505                 510
Asp Val Glu Gly Leu Leu Glu Leu Tyr Glu Ala Thr Ser Met Arg Val
        515                 520                 525
Pro Gly Glu Ile Ile Leu Glu Asp Ala Leu Gly Phe Thr Arg Ser Arg
    530                 535                 540
Leu Ser Ile Met Thr Lys Asp Ala Phe Ser Thr Asn Pro Ala Leu Phe
545                 550                 555                 560
Thr Glu Ile Gln Arg Ala Leu Lys Gln Pro Leu Trp Lys Arg Leu Pro
                565                 570                 575
Arg Ile Glu Ala Ala Gln Tyr Ile Pro Phe Tyr Gln Gln Gln Asp Ser
            580                 585                 590
His Asn Lys Thr Leu Leu Lys Leu Ala Lys Leu Glu Phe Asn Leu Leu
        595                 600                 605
Gln Ser Leu His Lys Glu Glu Leu Ser His Val Cys Lys Trp Trp Lys
    610                 615                 620
Ala Phe Asp Ile Lys Lys Asn Ala Pro Cys Leu Arg Asp Arg Ile Val
625                 630                 635                 640
Glu Cys Tyr Phe Trp Gly Leu Gly Ser Gly Tyr Glu Pro Gln Tyr Ser
                645                 650                 655
Arg Ala Arg Val Phe Phe Thr Lys Ala Val Ala Val Ile Thr Leu Ile
            660                 665                 670
Asp Asp Thr Tyr Asp Ala Tyr Gly Thr Tyr Glu Glu Leu Lys Ile Phe
        675                 680                 685
Thr Glu Ala Val Glu Arg Trp Ser Ile Thr Cys Leu Asp Thr Leu Pro
    690                 695                 700
Glu Tyr Met Lys Pro Ile Tyr Lys Leu Phe Met Asp Thr Tyr Thr Glu
705                 710                 715                 720
Met Glu Glu Phe Leu Ala Lys Glu Gly Arg Thr Asp Leu Phe Asn Cys
                725                 730                 735
Gly Lys Glu Phe Val Lys Glu Phe Val Arg Asn Leu Met Val Glu Ala
            740                 745                 750
Lys Trp Ala Asn Glu Gly His Ile Pro Thr Thr Glu Glu His Asp Pro
        755                 760                 765
Val Val Ile Ile Thr Gly Gly Ala Asn Leu Leu Thr Thr Thr Cys Tyr
    770                 775                 780
Leu Gly Met Ser Asp Ile Phe Thr Lys Glu Ser Val Glu Trp Ala Val
785                 790                 795                 800
Ser Ala Pro Pro Leu Phe Arg Tyr Ser Gly Ile Leu Gly Arg Arg Leu
                805                 810                 815
Asn Asp Leu Met Thr His Lys Ala Glu Gln Glu Arg Lys His Ser Ser
            820                 825                 830
Ser Ser Leu Glu Ser Tyr Met Lys Glu Tyr Asn Val Asn Glu Glu Tyr
        835                 840                 845
Ala Gln Thr Leu Ile Tyr Lys Glu Val Glu Asp Val Trp Lys Asp Ile
    850                 855                 860
Asn Arg Glu Tyr Leu Thr Thr Lys Asn Ile Pro Arg Pro Leu Leu Met
865                 870                 875                 880
Ala Val Ile Tyr Leu Cys Gln Phe Leu Glu Val Gln Tyr Ala Gly Lys
                885                 890                 895
Asp Asn Phe Thr Arg Met Gly Asp Glu Tyr Lys His Leu Ile Lys Ser
            900                 905                 910
Leu Leu Val Tyr Pro Met Ser Ile
```

<210> SEQ ID NO 30
<211> LENGTH: 41
<212> TYPE: DNA
<213> ORGANISM: Artificial
<220> FEATURE:
<223> OTHER INFORMATION: primer

<400> SEQUENCE: 30
tatatggatc catggctgaa atgtttaatg gaaattccag c       41

<210> SEQ ID NO 31
<211> LENGTH: 20
<212> TYPE: DNA
<213> ORGANISM: Artificial
<220> FEATURE:
<223> OTHER INFORMATION: primer

<400> SEQUENCE: 31
gattatgcgg ccgtgtacaa       20

<210> SEQ ID NO 32
<211> LENGTH: 20
<212> TYPE: DNA
<213> ORGANISM: Artificial
<220> FEATURE:
<223> OTHER INFORMATION: primer

<400> SEQUENCE: 32
ttgtaaaacg acggccagtg       20

<210> SEQ ID NO 33
<211> LENGTH: 23
<212> TYPE: DNA
<213> ORGANISM: Artificial
<220> FEATURE:
<223> OTHER INFORMATION: primer

<400> SEQUENCE: 33
gtgacactat agaatactca agc       23

<210> SEQ ID NO 34
<211> LENGTH: 40
<212> TYPE: PRT
<213> ORGANISM: Artificial
<220> FEATURE:
<223> OTHER INFORMATION: SET tag

<400> SEQUENCE: 34

Glu Glu Ala Ser Val Thr Ser Thr Glu Glu Thr Leu Thr Pro Ala Gln
1               5                   10                  15

Glu Ala Ala Arg Thr Arg Ala Ala Asn Lys Ala Arg Lys Glu Ala Glu
            20                  25                  30

Leu Ala Ala Ala Thr Ala Glu Gln
        35                  40

<210> SEQ ID NO 35
<211> LENGTH: 41
<212> TYPE: PRT
<213> ORGANISM: Artificial
<220> FEATURE:
<223> OTHER INFORMATION: SET tag (long)

<400> SEQUENCE: 35

-continued

```
Met Glu Glu Ala Ser Val Thr Ser Thr Glu Glu Thr Leu Thr Pro Ala
1               5                   10                  15

Gln Glu Ala Ala Arg Thr Arg Ala Ala Asn Lys Ala Arg Lys Glu Ala
            20              25                  30

Glu Leu Ala Ala Ala Thr Ala Glu Gln
        35              40
```